(12) United States Patent
Childers et al.

(10) Patent No.: US 8,329,030 B2
(45) Date of Patent: Dec. 11, 2012

(54) HEMODIALYSIS SYSTEM WITH CASSETTE AND PINCH CLAMP

(75) Inventors: Robert W. Childers, Trinity, FL (US); Thomas D. Kelly, Highland Park, IL (US); Rodolfo Roger, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/213,737

(22) Filed: Aug. 19, 2011

(65) Prior Publication Data

US 2012/0037550 A1    Feb. 16, 2012

Related U.S. Application Data

(63) Continuation of application No. 12/257,014, filed on Oct. 23, 2008, now Pat. No. 8,114,276.

(60) Provisional application No. 60/982,323, filed on Oct. 24, 2007.

(51) Int. Cl.
*B01D 61/24* (2006.01)

(52) U.S. Cl. ............ 210/175; 210/143; 210/321.6; 210/258; 210/646; 604/5.01; 417/477.1; 417/477.2

(58) Field of Classification Search .......... 210/141, 210/143, 258, 321.6, 321.71, 645–647, 175, 210/184; 604/4.01, 5.01, 6.01, 6.09, 6.11; 417/474, 475, 476, 477.1, 477.2, 477.7, 447.8, 417/477.9

See application file for complete search history.

(56) References Cited

U.S. PATENT DOCUMENTS

| | | | |
|---|---|---|---|
| 250,868 A | 12/1881 | Abbott | |
| 927,476 A | 7/1909 | Barker | |
| 1,505,050 A | 8/1924 | Lauritsen | |
| 2,292,007 A | 8/1942 | Morgan | |
| 2,698,578 A * | 1/1955 | Anderson | ............ 74/583 |
| 3,044,236 A | 7/1962 | Bearden et al. | |
| 3,074,645 A | 1/1963 | Main | |
| 3,095,062 A | 6/1963 | Neely | |

(Continued)

FOREIGN PATENT DOCUMENTS

CH    296007    1/1954

(Continued)

OTHER PUBLICATIONS

U.S. Appl. No. 11/773,742, filed Jul. 5, 2007, Childers et al.

(Continued)

*Primary Examiner* — Joseph Drodge
(74) *Attorney, Agent, or Firm* — K&L Gates LLP

(57) ABSTRACT

A hemodialysis system includes (i) blood tubing; (ii) a peristaltic blood pump contacting the blood tubing to pump blood through the blood tubing; (iii) a dialyzer in fluid communication with the blood tubing; (iv) first and second peristaltic dialysate pumps; (v) a dialysate heater; (vi) a plurality of pinch valves; and (vii) a cassette including a rigid structure, a heating portion, first and second dialysate pumping tubes, and a plurality of incoming tubes, the rigid structure when the cassette is mounted for operation orienting (a) the heating portion adjacent to the dialysate heater so that dialysate can be heated by the dialysate heater, (b) the first and second dialysate pumping tubes adjacent to the first and second peristaltic dialysate pumps, and (c) the plurality of incoming tubes adjacent to the plurality of pinch valves to enable the tubes to be individually closed by the pinch valves.

18 Claims, 48 Drawing Sheets

U.S. PATENT DOCUMENTS

| | | | |
|---|---|---|---|
| 3,229,445 A | 1/1966 | Kraft | |
| 3,287,885 A | 11/1966 | Sommer | |
| 3,295,297 A | 1/1967 | Collins | |
| 3,342,019 A | 9/1967 | Smythe | |
| 3,412,760 A | 11/1968 | Franck | |
| 3,527,572 A | 9/1970 | Urkiewicz | |
| 3,581,464 A | 6/1971 | Bhuta et al. | |
| 3,598,727 A | 8/1971 | Wilock | |
| 3,677,710 A | 7/1972 | Hirsch | |
| 3,744,492 A | 7/1973 | Leibinsohn | |
| 3,756,234 A | 9/1973 | Kopp | |
| 3,769,207 A | 10/1973 | Baer | |
| 3,771,288 A | 11/1973 | Wisman et al. | |
| 3,795,088 A | 3/1974 | Esmond | |
| 3,827,561 A | 8/1974 | Serfass et al. | |
| 3,830,234 A | 8/1974 | Kopp | |
| 3,834,386 A | 9/1974 | Sisley | |
| 3,849,071 A | 11/1974 | Kayser | |
| 3,908,653 A | 9/1975 | Kettering | |
| 3,946,731 A | 3/1976 | Lichtenstein | |
| 3,964,479 A | 6/1976 | Boag et al. | |
| 3,976,311 A | 8/1976 | Spendlove | |
| 3,976,576 A | 8/1976 | Jacobsen et al. | |
| 3,985,134 A | 10/1976 | Lissot et al. | |
| 3,996,027 A | 12/1976 | Schnell et al. | |
| 4,031,891 A | 6/1977 | Jess | |
| 4,038,190 A | 7/1977 | Baudet et al. | |
| 4,047,563 A | 9/1977 | Kurata | |
| 4,048,995 A | 9/1977 | Mittleman | |
| 4,054,522 A | 10/1977 | Pinkerton | |
| 4,061,031 A | 12/1977 | Grimsrud | |
| 4,102,655 A | 7/1978 | Jeffrey et al. | |
| 4,137,160 A | 1/1979 | Ebling et al. | |
| 4,141,836 A | 2/1979 | Schael | |
| 4,149,860 A | 4/1979 | Kulik | |
| 4,151,088 A | 4/1979 | Wolf, Jr. et al. | |
| 4,180,460 A | 12/1979 | Calari | |
| 4,181,245 A | 1/1980 | Garrett et al. | |
| 4,191,182 A | 3/1980 | Popovich et al. | |
| 4,200,095 A | 4/1980 | Reti | |
| 4,244,816 A | 1/1981 | Vogler et al. | |
| 4,293,413 A | 10/1981 | Schnell | |
| 4,303,376 A | 12/1981 | Siekmann | |
| 4,304,670 A | 12/1981 | Watanabe et al. | |
| 4,311,137 A | 1/1982 | Gerard | |
| 4,325,715 A | 4/1982 | Bowman et al. | |
| 4,332,264 A | 6/1982 | Gortz et al. | |
| 4,344,777 A | 8/1982 | Siposs | |
| 4,345,919 A | 8/1982 | Wilkinson et al. | |
| 4,345,999 A | 8/1982 | Sigdell et al. | |
| RE31,029 E | 9/1982 | Schael | |
| 4,353,368 A | 10/1982 | Slovak et al. | |
| 4,363,641 A | 12/1982 | Finn, III | |
| 4,368,118 A | 1/1983 | Siposs | |
| 4,386,634 A | 6/1983 | Stasz et al. | |
| 4,427,009 A | 1/1984 | Wells et al. | |
| 4,433,971 A | 2/1984 | Lindsay et al. | |
| 4,464,172 A | 8/1984 | Lichtenstein | |
| 4,468,329 A | 8/1984 | Shaldon et al. | |
| 4,477,342 A | 10/1984 | Allan et al. | |
| 4,486,188 A | 12/1984 | Altshuler et al. | |
| 4,493,705 A | 1/1985 | Gordon et al. | |
| 4,512,163 A | 4/1985 | Wells et al. | |
| 4,531,937 A | 7/1985 | Yates | |
| 4,568,333 A | 2/1986 | Sawyer et al. | |
| 4,583,981 A | 4/1986 | Urquhart et al. | |
| 4,586,925 A | 5/1986 | Carlsson et al. | |
| 4,622,032 A | 11/1986 | Katsura et al. | |
| 4,643,713 A | 2/1987 | Viitala | |
| 4,643,715 A | 2/1987 | Isono et al. | |
| 4,650,458 A | 3/1987 | Dahlberg et al. | |
| 4,657,490 A | 4/1987 | Abbott | |
| 4,661,246 A | 4/1987 | Ash | |
| 4,666,598 A | 5/1987 | Heath et al. | |
| 4,681,606 A | 7/1987 | Swan, Jr. et al. | |
| 4,702,829 A | 10/1987 | Polaschegg et al. | |
| 4,708,802 A | 11/1987 | Rath et al. | |
| 4,722,725 A | 2/1988 | Sawyer et al. | |
| 4,722,731 A | 2/1988 | Vailancourt | |
| 4,734,269 A | 3/1988 | Clarke et al. | |
| 4,767,399 A | 8/1988 | Bollish | |
| 4,778,451 A | 10/1988 | Kamen | |
| 4,806,135 A | 2/1989 | Siposs | |
| 4,828,543 A | 5/1989 | Weiss et al. | |
| 4,838,865 A | 6/1989 | Flank et al. | |
| 4,923,612 A | 5/1990 | Trivett et al. | |
| 4,932,987 A | 6/1990 | Molina | |
| 4,941,875 A | 7/1990 | Brennan | |
| 4,946,439 A | 8/1990 | Eggers | |
| D311,061 S | 10/1990 | Vrana et al. | |
| 4,976,685 A | 12/1990 | Block, Jr. | |
| 4,997,464 A | 3/1991 | Kopf | |
| 5,002,471 A | 3/1991 | Perlov | |
| 5,011,607 A | 4/1991 | Shinzato | |
| 5,047,147 A | 9/1991 | Chevallet et al. | |
| 5,047,211 A | 9/1991 | Sloane, Jr. et al. | |
| 5,049,492 A | 9/1991 | Sauer et al. | |
| 5,059,173 A | 10/1991 | Sacco | |
| 5,061,236 A | 10/1991 | Sutherland et al. | |
| 5,061,365 A | 10/1991 | Utterberg | |
| 5,062,774 A | 11/1991 | Kramer et al. | |
| 5,088,515 A | 2/1992 | Kamen | |
| 5,091,094 A | 2/1992 | Veech | |
| 5,112,480 A | 5/1992 | Hukasawa | |
| 5,114,580 A | 5/1992 | Ahmad et al. | |
| 5,120,303 A | 6/1992 | Hombrouckx | |
| 5,167,921 A | 12/1992 | Gordon | |
| 5,173,125 A | 12/1992 | Felding | |
| 5,178,763 A | 1/1993 | Delaunay | |
| 5,204,000 A | 4/1993 | Steadman et al. | |
| 5,211,849 A | 5/1993 | Kitaevich et al. | |
| 5,215,450 A * | 6/1993 | Tamari | 417/474 |
| 5,221,267 A | 6/1993 | Folden | |
| 5,228,889 A | 7/1993 | Cortial et al. | |
| 5,246,560 A | 9/1993 | Nekoksa et al. | |
| 5,259,961 A | 11/1993 | Eigendorf | |
| 5,268,077 A | 12/1993 | Bubik et al. | |
| 5,273,517 A | 12/1993 | Barone et al. | |
| 5,311,908 A | 5/1994 | Barone et al. | |
| 5,328,461 A | 7/1994 | Utterberg | |
| 5,330,420 A | 7/1994 | Lee | |
| 5,336,165 A | 8/1994 | Twardowski | |
| D350,822 S | 9/1994 | Lanigan | |
| D350,823 S | 9/1994 | Lanigan | |
| 5,356,376 A | 10/1994 | Milijasevic et al. | |
| 5,358,481 A | 10/1994 | Todd et al. | |
| 5,368,555 A | 11/1994 | Sussman et al. | |
| 5,376,263 A | 12/1994 | Fischel | |
| 5,394,732 A | 3/1995 | Johnson et al. | |
| 5,401,342 A | 3/1995 | Vincent et al. | |
| D357,312 S | 4/1995 | Riquier et al. | |
| 5,411,472 A | 5/1995 | Steg, Jr. et al. | |
| 5,411,705 A | 5/1995 | Thor et al. | |
| 5,421,815 A | 6/1995 | Noguchi et al. | |
| 5,429,595 A | 7/1995 | Wright, Jr. et al. | |
| 5,431,626 A | 7/1995 | Bryant et al. | |
| 5,441,636 A | 8/1995 | Chevallet et al. | |
| 5,468,388 A | 11/1995 | Goddard et al. | |
| 5,470,483 A | 11/1995 | Bene et al. | |
| 5,484,397 A | 1/1996 | Twardowski | |
| 5,489,385 A | 2/1996 | Raabe et al. | |
| 5,490,925 A | 2/1996 | Eigendorf | |
| 5,503,801 A | 4/1996 | Brugger | |
| 5,509,895 A | 4/1996 | Noguchi et al. | |
| 5,520,640 A | 5/1996 | Utterberg | |
| 5,540,808 A | 7/1996 | Vincent et al. | |
| 5,545,131 A | 8/1996 | Davankov | |
| 5,570,026 A | 10/1996 | Buffaloe, IV et al. | |
| 5,578,070 A | 11/1996 | Utterberg | |
| 5,578,268 A | 11/1996 | Champseix et al. | |
| 5,588,816 A | 12/1996 | Abbott et al. | |
| 5,591,251 A | 1/1997 | Brugger | |
| 5,605,540 A | 2/1997 | Utterberg | |
| 5,609,572 A | 3/1997 | Lang | |
| 5,614,677 A | 3/1997 | Wamsiedler et al. | |
| 5,634,896 A | 6/1997 | Bryant et al. | |
| 5,637,081 A | 6/1997 | Noguchi et al. | |

| Patent No. | Date | Inventor |
|---|---|---|
| 5,643,205 A | 7/1997 | Utterberg |
| 5,650,071 A | 7/1997 | Brugger et al. |
| 5,674,199 A | 10/1997 | Brugger |
| 5,674,397 A | 10/1997 | Pawlak et al. |
| 5,681,294 A | 10/1997 | Osborne et al. |
| 5,683,355 A | 11/1997 | Fini et al. |
| 5,685,988 A | 11/1997 | Malchesky |
| 5,690,831 A | 11/1997 | Kenley et al. |
| 5,702,597 A | 12/1997 | Chevallet et al. |
| 5,702,606 A | 12/1997 | Peter, Jr. et al. |
| 5,725,773 A | 3/1998 | Polaschegg |
| 5,725,776 A | 3/1998 | Kenley et al. |
| 5,730,712 A | 3/1998 | Falkvall et al. |
| 5,730,730 A | 3/1998 | Darling, Jr. |
| 5,744,095 A | 4/1998 | Smith |
| 5,763,266 A | 6/1998 | Palsson et al. |
| 5,776,078 A | 7/1998 | Wardlaw |
| 5,776,091 A | 7/1998 | Brugger et al. |
| 5,776,345 A | 7/1998 | Truitt et al. |
| 5,782,575 A | 7/1998 | Vincent et al. |
| 5,800,597 A | 9/1998 | Perrotta et al. |
| 5,830,185 A | 11/1998 | Block, Jr. |
| 5,836,908 A | 11/1998 | Beden et al. |
| 5,846,419 A | 12/1998 | Nederlof |
| 5,849,065 A | 12/1998 | Wojke |
| 5,851,202 A | 12/1998 | Carlsson |
| 5,858,239 A | 1/1999 | Kenley et al. |
| 5,863,421 A | 1/1999 | Peter, Jr. et al. |
| 5,871,694 A | 2/1999 | Beden et al. |
| 5,871,696 A | 2/1999 | Roberts et al. |
| 5,895,368 A | 4/1999 | Utterberg |
| 5,902,476 A | 5/1999 | Twardowski |
| 5,910,252 A | 6/1999 | Truitt et al. |
| 5,919,369 A | 7/1999 | Ash |
| 5,925,011 A | 7/1999 | Faict et al. |
| 5,928,744 A | 7/1999 | Heilmann et al. |
| 5,928,889 A | 7/1999 | Bakich et al. |
| 5,931,990 A | 8/1999 | Andrews |
| 5,932,103 A | 8/1999 | Kenley et al. |
| 5,938,634 A | 8/1999 | Packard |
| 5,948,251 A | 9/1999 | Brugger |
| 5,951,870 A | 9/1999 | Utterberg |
| 5,957,153 A | 9/1999 | Frey et al. |
| 5,980,741 A | 11/1999 | Schnell et al. |
| 5,983,947 A | 11/1999 | Utterberg |
| 5,989,318 A | 11/1999 | Schroll |
| 5,989,423 A | 11/1999 | Kamen et al. |
| 5,997,818 A | 12/1999 | Hacker et al. |
| 6,000,567 A | 12/1999 | Carlsson et al. |
| 6,001,201 A | 12/1999 | Vincent et al. |
| 6,004,311 A | 12/1999 | Heilmann et al. |
| 6,010,623 A | 1/2000 | Schnell et al. |
| 6,019,824 A | 2/2000 | Schnell |
| 6,036,858 A | 3/2000 | Carlsson et al. |
| 6,036,924 A | 3/2000 | Simons et al. |
| 6,046,806 A | 4/2000 | Thompson |
| 6,051,134 A | 4/2000 | Schnell et al. |
| 6,053,967 A | 4/2000 | Heilmann et al. |
| 6,066,111 A | 5/2000 | Brockhoff |
| 6,071,269 A | 6/2000 | Schnell et al. |
| 6,101,406 A | 8/2000 | Hacker et al. |
| 6,117,342 A | 9/2000 | Schnell et al. |
| 6,129,699 A | 10/2000 | Haight et al. |
| 6,132,616 A | 10/2000 | Twardowski et al. |
| 6,139,748 A | 10/2000 | Ericson et al. |
| 6,146,536 A | 11/2000 | Twardowski |
| 6,171,484 B1 | 1/2001 | Schnell et al. |
| 6,176,903 B1 | 1/2001 | Wamsiedler |
| 6,187,198 B1 | 2/2001 | Utterberg |
| 6,206,954 B1 | 3/2001 | Schnell et al. |
| 6,210,361 B1 | 4/2001 | Kamen et al. |
| 6,234,992 B1 | 5/2001 | Haight et al. |
| 6,251,167 B1 | 6/2001 | Berson |
| 6,254,567 B1 | 7/2001 | Treu et al. |
| 6,260,715 B1 | 7/2001 | Simard et al. |
| 6,274,034 B1 | 8/2001 | Nikaido et al. |
| 6,280,632 B1 | 8/2001 | Polaschegg |
| 6,287,516 B1 | 9/2001 | Matson et al. |
| 6,302,653 B1 | 10/2001 | Bryant et al. |
| 6,312,414 B1 | 11/2001 | Brockhoff et al. |
| 6,315,895 B1 | 11/2001 | Summerton et al. |
| 6,322,551 B1 | 11/2001 | Brugger |
| 6,325,775 B1 | 12/2001 | Thom et al. |
| 6,331,252 B1 | 12/2001 | El Sayyid et al. |
| 6,344,139 B1 | 2/2002 | Utterberg |
| 6,357,600 B1 | 3/2002 | Scagliarini |
| 6,364,857 B1 | 4/2002 | Gray et al. |
| 6,382,923 B1 | 5/2002 | Gray |
| 6,391,541 B1 | 5/2002 | Petersen et al. |
| 6,391,638 B1 | 5/2002 | Shaaltiel |
| 6,406,631 B1 | 6/2002 | Collins et al. |
| 6,416,293 B1 | 7/2002 | Bouchard et al. |
| 6,447,491 B1 | 9/2002 | Lord |
| 6,454,736 B1 | 9/2002 | Ludt et al. |
| 6,464,878 B2 | 10/2002 | Utterberg |
| 6,471,855 B1 | 10/2002 | Odak et al. |
| 6,472,220 B1 | 10/2002 | Simons et al. |
| 6,481,455 B2 | 11/2002 | Gustafson et al. |
| 6,481,980 B1 | 11/2002 | Vandlik et al. |
| 6,484,383 B1 | 11/2002 | Herklotz |
| 6,485,263 B1 | 11/2002 | Bryant et al. |
| 6,491,656 B1 | 12/2002 | Morris |
| 6,495,366 B1 | 12/2002 | Briggs |
| 6,514,255 B1 | 2/2003 | Ferree |
| 6,531,061 B1 | 3/2003 | Cholewa |
| 6,537,356 B1 | 3/2003 | Soriano |
| 6,537,450 B2 | 3/2003 | Russell et al. |
| 6,551,513 B2 | 4/2003 | Nikaido et al. |
| 6,554,789 B1 | 4/2003 | Brugger et al. |
| 6,558,340 B1 | 5/2003 | Traeger |
| 6,561,997 B1 | 5/2003 | Weitzel et al. |
| 6,562,107 B2 | 5/2003 | Purdom et al. |
| 6,572,576 B2 | 6/2003 | Brugger et al. |
| 6,572,641 B2 | 6/2003 | Brugger et al. |
| 6,579,253 B1 | 6/2003 | Burbank et al. |
| 6,582,385 B2 | 6/2003 | Burbank et al. |
| 6,582,604 B2 | 6/2003 | Nikaido et al. |
| 6,582,955 B2 | 6/2003 | Martinez et al. |
| 6,589,482 B1 | 7/2003 | Burbank et al. |
| 6,595,948 B2 | 7/2003 | Suzuki et al. |
| 6,604,908 B1 | 8/2003 | Bryant et al. |
| 6,620,120 B2 | 9/2003 | Landry et al. |
| 6,623,441 B1 | 9/2003 | Kihara et al. |
| 6,635,179 B1 | 10/2003 | Summerton et al. |
| 6,638,477 B1 | 10/2003 | Treu et al. |
| 6,638,478 B1 | 10/2003 | Treu et al. |
| 6,649,063 B2 | 11/2003 | Brugger et al. |
| 6,663,359 B2 | 12/2003 | Gray |
| 6,702,561 B2 | 3/2004 | Stillig et al. |
| 6,706,007 B2 | 3/2004 | Gelfand et al. |
| 6,719,907 B2 | 4/2004 | Collins et al. |
| 6,730,233 B2 | 5/2004 | Pedrazzi |
| 6,743,201 B1 | 6/2004 | Donig et al. |
| 6,749,403 B2 | 6/2004 | Bryant et al. |
| 6,749,818 B2 | 6/2004 | Sano et al. |
| 6,752,172 B2 | 6/2004 | Lauer |
| 6,755,801 B2 | 6/2004 | Utterberg et al. |
| 6,764,460 B2 | 7/2004 | Dolecek et al. |
| 6,770,049 B2 | 8/2004 | Ludt et al. |
| 6,802,971 B2 | 10/2004 | Gorsuch et al. |
| 6,821,441 B2 | 11/2004 | Pedrini et al. |
| 6,827,862 B1 | 12/2004 | Brockhoff et al. |
| 6,830,553 B1 | 12/2004 | Burbank et al. |
| 6,843,779 B1 | 1/2005 | Andrysiak et al. |
| 6,852,090 B2 | 2/2005 | Burbank et al. |
| 6,877,713 B1 | 4/2005 | Gray et al. |
| 6,878,283 B2 | 4/2005 | Thompson |
| 6,884,441 B2 | 4/2005 | Pippert et al. |
| 6,887,214 B1 | 5/2005 | Levin et al. |
| 6,899,693 B2 | 5/2005 | Ghelli et al. |
| 6,905,479 B1 | 6/2005 | Bouchard et al. |
| 6,916,424 B2 * | 7/2005 | Collins et al. ............ 210/646 |
| 6,919,326 B1 | 7/2005 | Miyata |
| 6,929,743 B2 | 8/2005 | Diel |
| 6,960,178 B2 | 11/2005 | Chang et al. |
| 7,037,428 B1 | 5/2006 | Robinson et al. |
| 7,040,142 B2 | 5/2006 | Burbank |
| 7,074,332 B2 | 7/2006 | Summerton et al. |

| | | |
|---|---|---|
| 7,077,956 B2 | 7/2006 | Rovatti |
| 7,087,033 B2 | 8/2006 | Brugger et al. |
| 7,097,690 B2 | 8/2006 | Usher et al. |
| 7,112,273 B2 | 9/2006 | Weigel et al. |
| 7,115,107 B2 | 10/2006 | Delnevo et al. |
| 7,115,205 B2 | 10/2006 | Robinson et al. |
| 7,128,836 B2 | 10/2006 | De Paolis et al. |
| 7,134,489 B2 | 11/2006 | Van Riet |
| 7,150,755 B2 | 12/2006 | Levaughn et al. |
| 7,169,352 B1 | 1/2007 | Felt et al. |
| 7,175,606 B2 | 2/2007 | Bowman, Jr. et al. |
| 7,186,342 B2 | 3/2007 | Pirazzoli et al. |
| 7,195,607 B2 | 3/2007 | Westberg et al. |
| 7,214,312 B2 | 5/2007 | Brugger et al. |
| 7,223,338 B2 | 5/2007 | Duchamp et al. |
| 7,232,418 B2 | 6/2007 | Neri et al. |
| 7,238,164 B2 | 7/2007 | Childers et al. |
| 7,250,100 B2 | 7/2007 | Yonish |
| 7,285,106 B2 | 10/2007 | Collins et al. |
| 7,297,689 B2 | 11/2007 | Miyata |
| 7,300,413 B2 | 11/2007 | Burbank et al. |
| D556,909 S | 12/2007 | Reihanifam et al. |
| 7,311,689 B2 | 12/2007 | Levin et al. |
| 7,314,460 B2 | 1/2008 | Tu et al. |
| 7,374,672 B2 | 5/2008 | Hofmann |
| 7,407,501 B2 | 8/2008 | Zvuloni |
| 7,410,473 B2 | 8/2008 | Levin et al. |
| 7,465,285 B2 | 12/2008 | Hutchinson et al. |
| 7,476,209 B2 | 1/2009 | Gara et al. |
| 7,531,098 B2 | 5/2009 | Robinson et al. |
| 7,666,149 B2 | 2/2010 | Simons et al. |
| 7,686,779 B1 | 3/2010 | Gibbs |
| 7,695,423 B2 | 4/2010 | Robinson et al. |
| 7,736,328 B2 | 6/2010 | Childers et al. |
| 7,867,214 B2 | 1/2011 | Childers et al. |
| 7,883,473 B2 | 2/2011 | LeVaughn et al. |
| 8,029,454 B2 * | 10/2011 | Kelly et al. .................. 604/5.01 |
| 2001/0021817 A1 | 9/2001 | Brugger et al. |
| 2001/0037079 A1 | 11/2001 | Burbank et al. |
| 2001/0042441 A1 | 11/2001 | Purdom et al. |
| 2002/0068015 A1 | 6/2002 | Polaschegg et al. |
| 2002/0072718 A1 | 6/2002 | Brugger et al. |
| 2002/0143283 A1 | 10/2002 | Braverman et al. |
| 2002/0147423 A1 | 10/2002 | Burbank et al. |
| 2003/0010717 A1 | 1/2003 | Brugger et al. |
| 2003/0010718 A1 | 1/2003 | Burbank et al. |
| 2003/0018290 A1 | 1/2003 | Brugger et al. |
| 2004/0019313 A1 | 1/2004 | Childers et al. |
| 2004/0019314 A1 | 1/2004 | Delnevo |
| 2004/0138607 A1 | 7/2004 | Burbank et al. |
| 2004/0158189 A1 | 8/2004 | Tonelli et al. |
| 2004/0176724 A1 | 9/2004 | Kamen et al. |
| 2004/0186416 A1 | 9/2004 | Caleffi |
| 2004/0238416 A1 | 12/2004 | Burbank et al. |
| 2004/0243046 A1 | 12/2004 | Brugger et al. |
| 2004/0243047 A1 | 12/2004 | Brugger et al. |
| 2004/0243048 A1 | 12/2004 | Brugger et al. |
| 2004/0243049 A1 | 12/2004 | Brugger et al. |
| 2004/0243050 A1 | 12/2004 | Treu et al. |
| 2004/0245161 A1 | 12/2004 | Treu et al. |
| 2004/0247185 A1 | 12/2004 | Sato et al. |
| 2004/0244331 A1 | 12/2004 | Burbank et al. |
| 2004/0267184 A1 | 12/2004 | Burbank et al. |
| 2005/0000868 A1 | 1/2005 | Weigel et al. |
| 2005/0004502 A1 | 1/2005 | O'Mahony et al. |
| 2005/0010158 A1 | 1/2005 | Brugger et al. |
| 2005/0011823 A1 | 1/2005 | Delnevo et al. |
| 2005/0020958 A1 | 1/2005 | Paolini et al. |
| 2005/0020959 A1 | 1/2005 | Brugger et al. |
| 2005/0020960 A1 | 1/2005 | Brugger et al. |
| 2005/0095141 A1 | 5/2005 | Lanigan et al. |
| 2005/0096583 A1 | 5/2005 | Demers et al. |
| 2005/0131332 A1 * | 6/2005 | Kelly et al. .................. 604/4.01 |
| 2005/0209563 A1 | 9/2005 | Hopping et al. |
| 2005/0230292 A1 | 10/2005 | Beden et al. |
| 2006/0084906 A1 | 4/2006 | Burbank et al. |
| 2006/0110274 A1 * | 5/2006 | Gottschalk .................. 417/477.6 |
| 2006/0122551 A1 | 6/2006 | Brieske |
| 2006/0195064 A1 | 8/2006 | Plahey et al. |
| 2006/0213835 A1 | 9/2006 | Nimura et al. |
| 2006/0222561 A1 | 10/2006 | Hutchinson et al. |
| 2006/0224099 A1 | 10/2006 | Hutchinson et al. |
| 2006/0237351 A1 | 10/2006 | Felding |
| 2007/0119246 A1 | 5/2007 | Miyakoshi et al. |
| 2007/0249983 A1 | 10/2007 | Tonelli et al. |
| 2007/0253463 A1 | 11/2007 | Perry et al. |
| 2007/0278155 A1 * | 12/2007 | Lo et al. .................. 210/646 |
| 2007/0293803 A1 | 12/2007 | Tonelli et al. |
| 2008/0175719 A1 | 7/2008 | Tracey et al. |
| 2008/0202591 A1 | 8/2008 | Grant et al. |
| 2008/0208103 A1 | 8/2008 | Demers et al. |
| 2008/0216898 A1 | 9/2008 | Grant et al. |
| 2008/0234620 A1 | 9/2008 | Tonelli et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2009/0004033 A1 | 1/2009 | Demers et al. |
| 2009/0008331 A1 | 1/2009 | Wilt et al. |
| 2009/0012456 A1 | 1/2009 | Childers et al. |
| 2009/0084721 A1 | 4/2009 | Yardimci et al. |
| 2009/0095679 A1 | 4/2009 | Demers et al. |
| 2009/0099498 A1 | 4/2009 | Demers et al. |
| 2009/0101549 A1 | 4/2009 | Kamen et al. |
| 2009/0105629 A1 | 4/2009 | Grant et al. |
| 2009/0107335 A1 | 4/2009 | Wilt et al. |
| 2009/0114582 A1 | 5/2009 | Grant et al. |

FOREIGN PATENT DOCUMENTS

| | | |
|---|---|---|
| DE | 1806654 | 5/1970 |
| DE | 20 02 033 | 8/1970 |
| DE | 29 01 628 | 7/1980 |
| DE | 31 22 756 A1 | 6/1982 |
| DE | 33 07 830 A1 | 6/1984 |
| DE | 34 42 744 | 6/1986 |
| DE | 40 03 452 A1 | 8/1991 |
| DE | 42 08 054 A1 | 10/1992 |
| DE | 41 22 754 A1 | 1/1993 |
| DE | 198 14 695 | 10/1999 |
| DE | 198 54 338 A1 | 6/2000 |
| EP | 0 058 325 | 8/1982 |
| EP | 0 106 026 | 4/1984 |
| EP | 0 143 340 | 6/1985 |
| EP | 0 143 341 A2 | 6/1985 |
| EP | 0 233 848 A2 | 8/1987 |
| EP | 0 318 993 | 6/1989 |
| EP | 0 350 675 | 1/1990 |
| EP | 0 373 455 B1 | 6/1990 |
| EP | 0 222 709 B1 | 5/1991 |
| EP | 0 490 212 A1 | 6/1992 |
| EP | 0 501 144 | 9/1992 |
| EP | 0 560 368 A2 | 9/1993 |
| EP | 0 560 368 B1 | 9/1993 |
| EP | 0 587 251 | 3/1994 |
| EP | 0 720 856 A2 | 7/1996 |
| EP | 0 720 856 B1 | 7/1996 |
| EP | 0 722 744 A1 | 7/1996 |
| EP | 0 776 222 | 6/1997 |
| EP | 0 826 383 A2 | 3/1998 |
| EP | 0 826 383 B1 | 3/1998 |
| EP | 0 826 384 A2 | 3/1998 |
| EP | 0 826 384 B1 | 3/1998 |
| EP | 0 659 091 B1 | 12/2000 |
| EP | 1 097 724 A2 | 5/2001 |
| EP | 1323439 A2 | 7/2003 |
| EP | 1323439 A3 | 7/2003 |
| EP | 1 837 046 | 9/2007 |
| FR | 2 397 197 | 2/1979 |
| FR | 2 585 251 | 1/1987 |
| GB | 1 408 319 | 10/1975 |
| GB | 2 014 060 A | 8/1979 |
| GB | 1 554 810 | 10/1979 |
| GB | 2 061 755 | 5/1981 |
| GB | 2 212 739 | 8/1989 |
| GR | 3 026 703 | 7/1998 |
| JP | 11-226121 | 8/1999 |
| JP | 2000-217908 A | 8/2000 |
| JP | 2000-296318 A | 10/2000 |
| JP | 2001-270856 | 10/2001 |

| | | |
|---|---|---|
| SU | 1001945 | 3/1983 |
| SU | 1821222 A1 | 6/1993 |
| WO | 94/15099 | 7/1994 |
| WO | 95/17597 | 6/1995 |
| WO | 97/09074 | 3/1997 |
| WO | 98/22165 | 5/1998 |
| WO | 98/23353 | 6/1998 |
| WO | 98/32477 | 7/1998 |
| WO | 99/42150 | 8/1999 |
| WO | 00/09182 | 2/2000 |
| WO | 00/31967 | 6/2000 |
| WO | 00/57925 | 10/2000 |
| WO | 00/57926 | 10/2000 |
| WO | 00/57927 | 10/2000 |
| WO | 00/64510 | 11/2000 |
| WO | 01/37786 A2 | 5/2001 |
| WO | 01/37894 A2 | 5/2001 |
| WO | 01/37895 A2 | 5/2001 |
| WO | 01/37900 A2 | 5/2001 |
| WO | 01/41831 A2 | 6/2001 |
| WO | 01/41832 A2 | 6/2001 |
| WO | 01/41833 A2 | 6/2001 |
| WO | 01/42758 A2 | 6/2001 |
| WO | 01/45769 A2 | 6/2001 |
| WO | 01/47576 A2 | 7/2001 |
| WO | 02/070042 A1 | 9/2002 |
| WO | 02/098491 | 12/2002 |
| WO | 2006/120415 | 11/2006 |
| WO | 2008/090406 | 7/2008 |

OTHER PUBLICATIONS

U.S. Appl. No. 11/773,763, filed Jul. 5, 2007, Childers et al.
U.S. Appl. No. 12/884,989, filed Sep. 17, 2010, Kelly et al.
U.S. Appl. No. 13/213,676, filed Aug. 19, 2011, Lo et al.
U.S. Appl. No. 13/213,727, filed Aug. 19, 2011, Childers et al.
International Search Report and Written Opinion for International Application No. PCT/US2008/068960 mailed on May 14, 2009.
Written Opinion of the International Searching Authority for International Application No. PCT/US2008/080166 mailed on Jan. 20, 2009.
International Search Report and Written Opinion for International Application No. PCT/US2008/081058 mailed on Jun. 8, 2009.

* cited by examiner

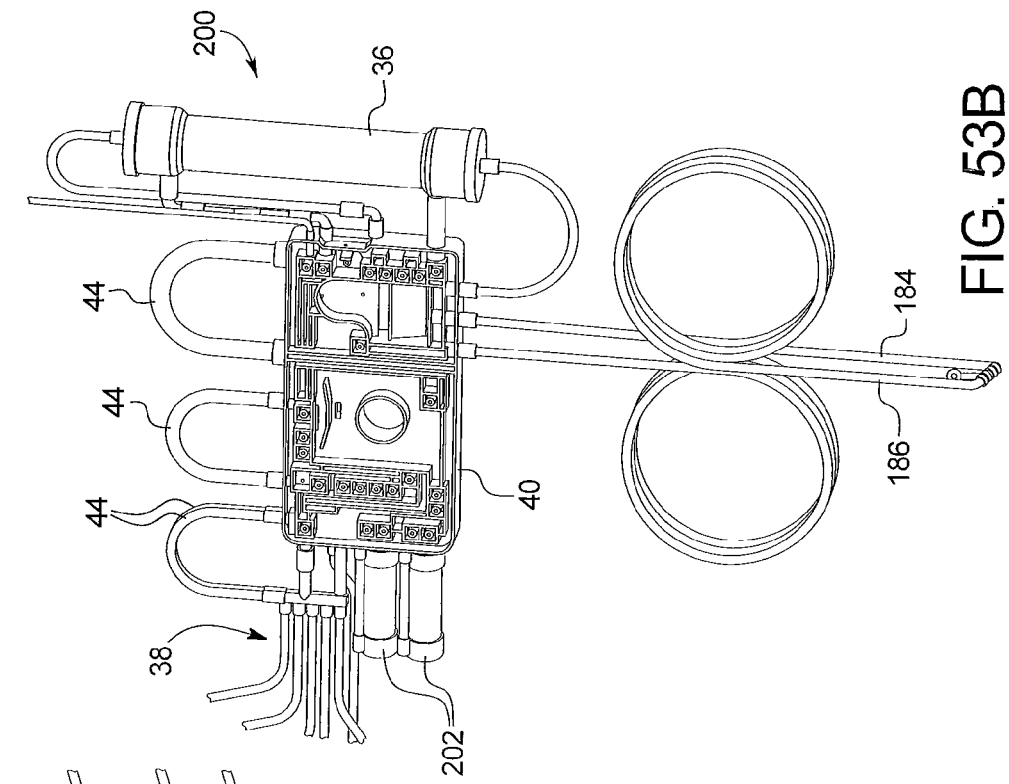
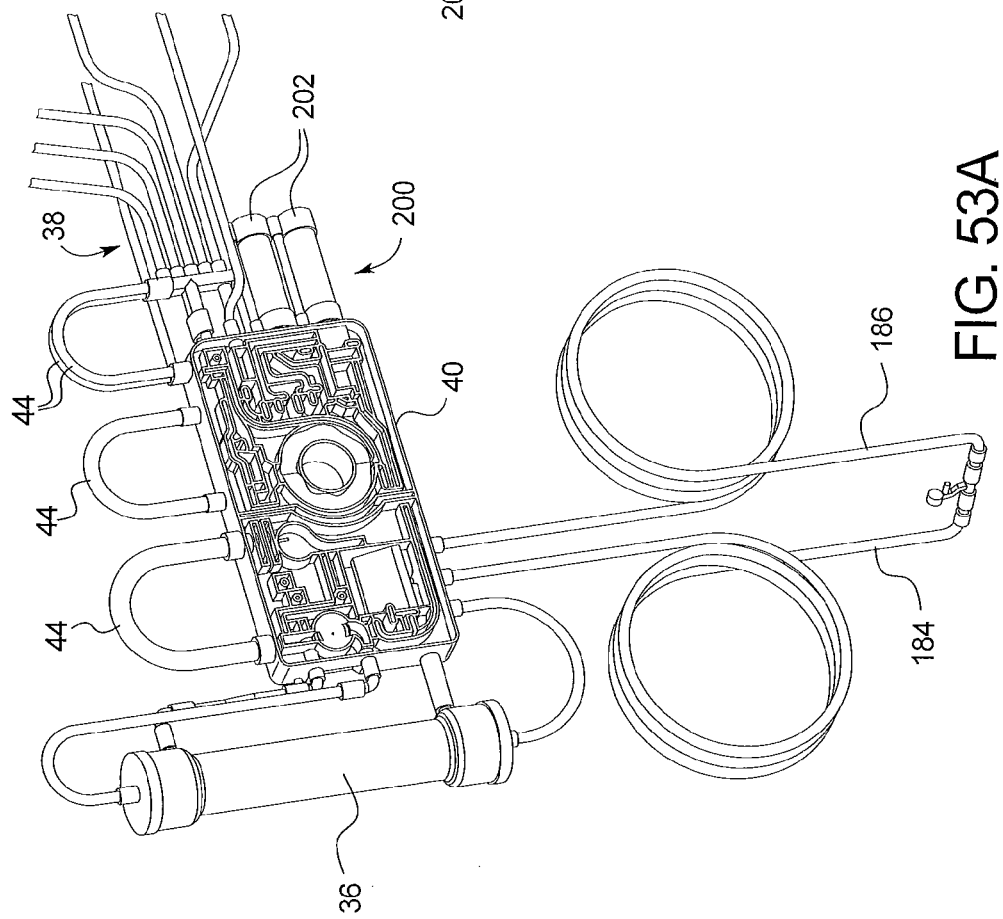
FIG. 53A
FIG. 53B

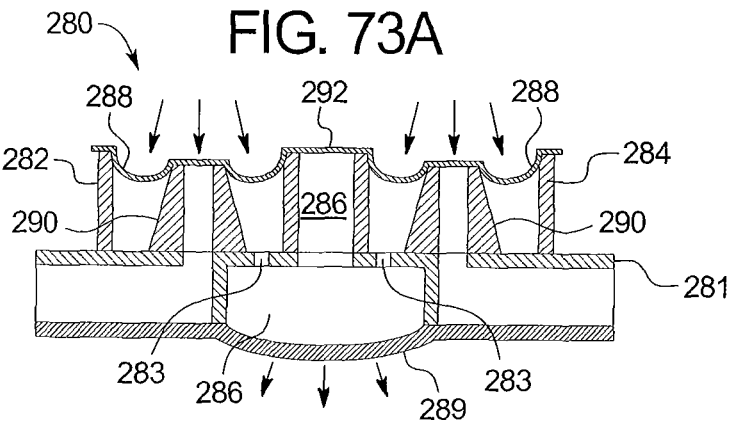
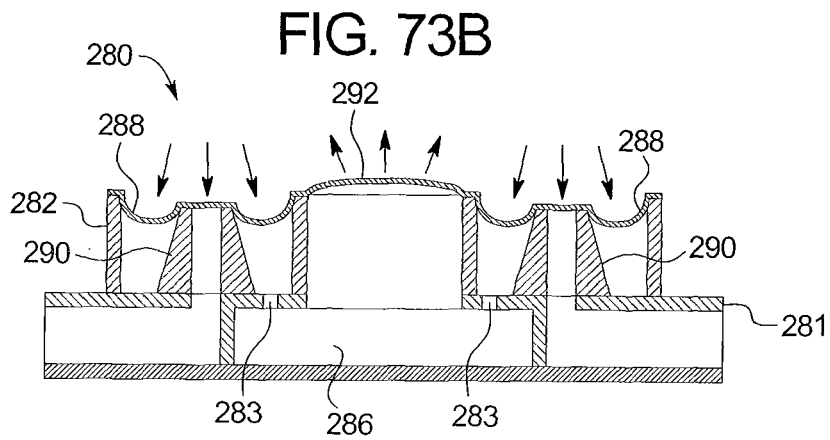
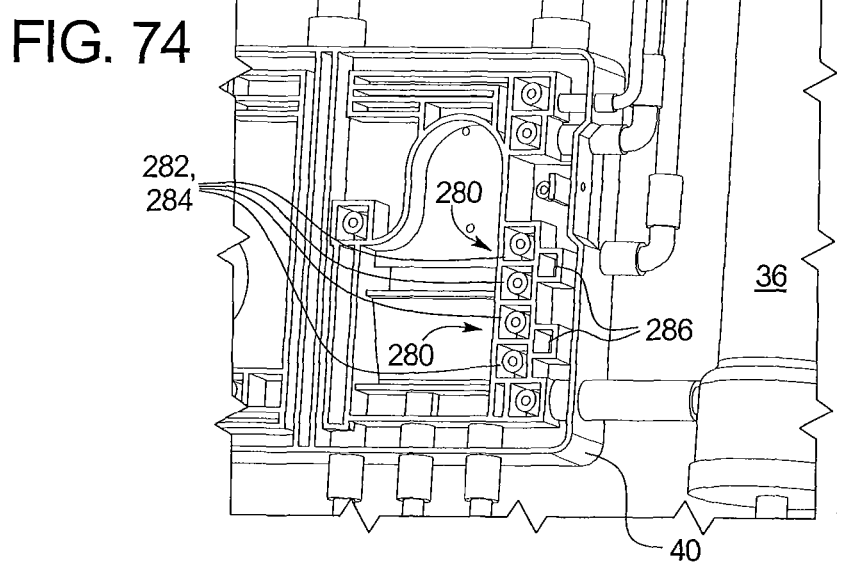

HEMODIALYSIS SYSTEM WITH CASSETTE AND PINCH CLAMP

PRIORITY

This application claims priority to and the benefit as a continuation of U.S. patent Ser. No. 12/257,014, entitled "Personal Hemodialysis System", filed Oct. 23, 2008, now U.S. Pat. No. 8,114,276, which claims priority to U.S. Provisional Patent Application No. 60/982,323, entitled "Personal Hemodialysis System", filed Oct. 24, 2007, the entire contents of each of which are incorporated herein by reference and relied upon.

BACKGROUND

The present disclosure relates generally to medical treatments. More specifically, the present disclosure relates to medical fluid treatments, such as the treatment of renal failure and fluid removal for congestive heart failure.

Hemodialysis ("HD") in general uses diffusion to remove waste products from a patient's blood. A diffusive gradient that occurs across the semi-permeable dialyzer between the blood and an electrolyte solution called dialysate causes diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Home hemodialysis ("HHD") is performed in the patient's home. One drawback of home hemodialysis has been the need for a dedicated water treatment, which includes equipment, water connection and drainage. Installing and using those components is a difficult and cumbersome task that can require a patient's home to be modified. Nevertheless, there are benefits to daily hemodialysis treatments versus bi- or tri-weekly visits to a treatment center. In particular, a patient receiving more frequent treatments removes more toxins and waste products than a patient receiving less frequent but perhaps longer treatments. Accordingly, there is a need for an improved HHD system.

SUMMARY

The present disclosure provides a home hemodialysis ("HHD") system. In one embodiment, the home system includes a mobile cart and integral bag manager. A latch is pulled out to unlock door of the system instrument. The door can be opened to expose a latch hook and peristaltic pump heads.

The instrument accepts a disposable unit which in one embodiment is loaded from above and slid to the right. The disposable unit pivots towards the machine interface, which allows peristaltic tube loops of the disposable unit to fit over peristaltic pump heads of the instrument. Also, supply lines of the disposable unit are passed over individual pinch valve plungers.

The pinch valve plungers pinch the supply tubes against a pinch valve strike plate. The valve assembly is in one embodiment a motor-driven cam operated pinch valve subassembly. The motor in one embodiment is a stepper motor.

The system in one embodiment includes a bellows or bladder that compresses a cassette against the instrument door using a pressure plate and gasket. These apparatuses are structured to accommodate an inline inductive heater provided with the disposable cassette. The bellows is air actuated in one embodiment. The instrument includes a primary coil that inductively heats conductive heating disks located within the cassette, which in turn heat fluid flowing through the cassette.

A multi-peristaltic pump race retracts and extends in one embodiment to facilitate loading of the peristaltic tubes of the cassette onto the peristaltic pump heads. The race is then moved towards the tubes for operation.

The system in one embodiment includes a manual blood pump operator, which allows the patient or caregiver to move the blood pump head manually.

The system includes a bag management system having shelves that fold up, out of the way, and down, sequentially for placement of supply bags. The system in one embodiment supports up to five, six liter solution bags. The bags can be dual chamber bags. The shelves in an embodiment are provided with sensors that allow detection of whether the bags have been (i) loaded or not and (ii) opened or not for therapy. The sensors in one embodiment are capacitive sensors placed on opposite ends of the shelves.

The disposable cassette in one embodiment connects fluidly to a heparin syringe for the injection of heparin into the blood circuit. The syringe fits into a luer connector assembly, which in turn is loaded into a syringe pump. The assembly is turned in the syringe pump to lock the syringe in the syringe pump for treatment. The assembly accommodates large syringes, such as fifty to sixty milliliter syringes, which can lock directly into the syringe pump. In one embodiment, the heparin line passes through the side of the cassette. Here, heparin can enter at the blood pump outlet just prior to the dialyzer inlet.

The system also includes a retractable saline bag support rod. The saline in one embodiment connects to the cassette near the heparin line. A saline valve is located on each side of the blood pump to control the flow of saline to same.

A dialyzer inlet pressure sensor interface in one embodiment doubles as a flow control valve. The cassette can also form an integral venus air separation chamber.

Priming is performed in one embodiment via gravity. Gravity primes the venous line, the arterial line and the air trap (drip chamber).

In another embodiment, priming is preformed via a combination of pumping dialysate and a physiologically safe fluid, such as saline. In particular, a hemodialysis machine can include a blood circuit, a dialysate circuit, a dialyzer placed in communication with the blood circuit and the dialysate circuit; and a priming sequence in which dialysate is used to prime a first portion of the dialysate circuit and a physiologically compatible solution, other than dialysate, is used to prime a second portion of the dialysate circuit, the dialyzer and the blood circuit. The first portion of the dialysate circuit includes a recirculation loop primed by a dialysate supply pump in one embodiment. The second portion of the dialysate circuit can then be located at least substantially between the recirculation loop and the dialyzer, and which is primed by at least one of a blood pump and a downstream dialysate pump. In one embodiment, a volumetric balancing unit separates the first and second portions of the dialysate circuit.

The cassette in one embodiment uses balance tubes to balance fresh and spend dialysate flow. The balance tubes have outlets at the top of the tubes when mounted for operation to allow air to leave the tubes. The cassette also employs diaphragm valves that operate with a compliance chamber that seals against backpressure.

For instance, a hemodialysis machine can include a dialysis instrument having at least one peristaltic pump actuator and first and second pneumatic valve actuators. The instrument operates with a disposable cassette, the disposable cassette including a rigid portion, with at least one peristaltic pump tube extending from the rigid portion for operation with the at least one pump actuator. The rigid portion defines first and second valve chambers in operable connection with the first and second valve actuators, respectively, the first and second valve chambers communicating fluidly with each other, at least the first valve chamber communicating fluidly with a compliance chamber, the compliance chamber absorbing energy from a pneumatic closing pressure applied to close the first valve chamber, so as to tend to prevent the pneumatic closing pressure from opening an existing closure of the second valve chamber.

The machine in one embodiment includes a vacuum applied to the compliance chamber to absorb the energy from the pneumatic closing pressure applied to close the first valve chamber.

In the above example, a flexible membrane can be sealed to the rigid portion, the pneumatic closing pressure applied to the membrane to close the first valve chamber. Here, the compliance chamber is formed in part via a portion of the flexible membrane, wherein the flexible membrane portion is configured to absorb the energy from the pneumatic closing pressure. The cassette can alternatively include a flexible diaphragm located on an opposing side of the rigid portion from the flexible membrane, the compliance chamber formed in part via the flexible diaphragm, the flexible diaphragm configured to absorb the energy from the pneumatic closing pressure.

The disposable cassette can have multiple compliance chambers operating with different sets of valve chambers. The compliance chamber aids both upstream and downstream valves. The compliance chamber overcomes a backpressure applied by the closing of the second valve chamber to the first valve chamber, to allow the first valve chamber to close properly.

In another compliance chamber embodiment, the dialysis instrument has a pump actuator and first and second valve actuators. A disposable cassette is operable with the dialysis instrument, the disposable cassette including a pump portion operable with the pump actuator, the first and second valve chambers communicating fluidly with each other, at least the first valve chamber communicating fluidly with a compliance chamber, the compliance chamber negating a first backpressure due to a pneumatic closing pressure used to close the first valve chamber to help to ensure the pneumatic pressure applied to the first valve chamber will close the first valve chamber against a second backpressure from an existing closure of the second valve chamber. Here, a pneumatic pressure applied to the second valve chamber can be the same as the pneumatic pressure applied to the first valve chamber. The first backpressure would exist around an outside of a port of the first valve chamber if not for the compliance chamber, the second backpressure existing inside the port. As before, the compliance chamber is further configured to tend to prevent the pneumatic pressure applied to the first valve chamber from opening the closed second valve chamber. And, the machine in one embodiment includes a vacuum applied to the compliance chamber to ensure the pneumatic pressure applied to the first valve chamber will close the first valve chamber.

In a further compliance chamber embodiment, the dialysis instrument has a pump actuator and first and second valve actuators. The disposable cassette is operable with the dialysis instrument, the disposable cassette including a pump portion operable with the pump actuator, and first and second valve chambers operable with the first and second valve actuators, respectively, the cassette further including a compliance chamber in fluid communication with the first and second valve chambers, the compliance chamber defined at least in part by a rigid wall of the cassette and a diaphragm located on an opposing side of the rigid wall from the first and second valve chambers. The rigid wall in one embodiment defines first and second apertures that allow the first and second valve chambers to communicate fluidly, respectively, with the compliance chamber. The cassette can include a flexible membrane located on an opposing side of the cassette from the diaphragm, the membrane for closing the first and second valve chambers. Again, the compliance chamber can aid at least one of: (i) maintenance of an existing closure of the second valve chamber when the first valve chamber is closed; and (ii) a proper closure of the first valve chamber at a time when the second valve chamber is already closed. In one embodiment, the aiding is provided via a vacuum applied to the compliance chamber.

In still a further compliance chamber embodiment, a dialysis instrument has a pump actuator and first and second valve actuator. A disposable cassette is operable with the dialysis instrument, the disposable cassette including a pump portion operable with the pump actuator, and first and second valve chambers operable with the first and second valve actuators, respectively. A compliance chamber is placed in fluid communication with the first and second valve chambers, the compliance chamber defined by in part by a flexible membrane used to close at least one of the first and second valve chambers, the valve chambers each defining an aperture for fluid communication with the compliance chamber. The disposable cassette can include a rigid wall, the first and second valves chambers extending from the rigid wall towards the flexible membrane, wherein the apertures of the first and second valve chambers are formed in the rigid wall, and wherein the rigid wall also forms a third, larger aperture to allow fluid flowing through the valve chamber apertures to communicate fluidly with the flexible membrane of the compliance chamber. Again, the compliance chamber aiding at least one of: (i) maintenance of an existing closure of the second valve chamber when the first valve chamber is closed; and (ii) a proper closure of the first valve chamber at a time when the second valve chamber is already closed. Again, the aiding can be provided via a vacuum applied to the compliance chamber.

It is therefore an advantage of the present disclosure to properly seal valves in fluid communication with one another.

It is another advantage of the present disclosure to provide an efficient priming technique that combines the use of dialysate and another physiologically safe fluid, such as saline.

Additional features and advantages are described herein, and will be apparent from, the following Detailed Description and the figures.

BRIEF DESCRIPTION OF THE FIGURES

FIGS. 53A and 53B illustrate one embodiment of a disposable set operable with the system of the present disclosure.

FIG. 73A illustrates one embodiment of a diaphragm valve assembly having a compliance chamber seal against backpressure, which is operable with the HHD system of the present disclosure.

FIG. 73B illustrates one embodiment of a valve assembly having compliance chambers.

FIG. 74 is a perspective view of a disposable cassette having the valve assembly of FIGS. 73A and 73B.

DETAILED DESCRIPTION

Figure 1:
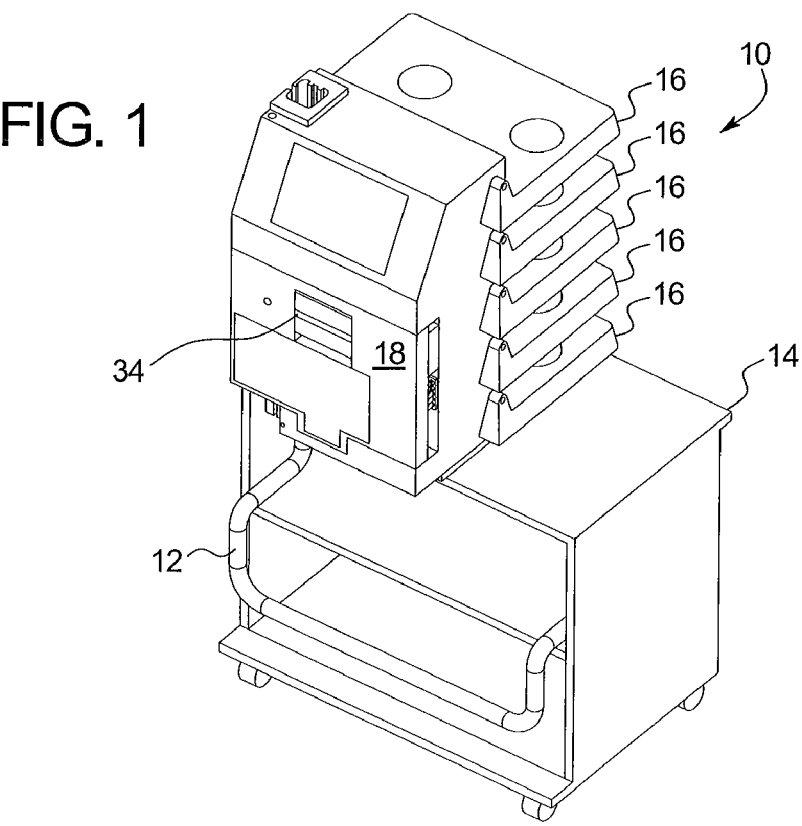
FIG. 1 is a perspective view of one embodiment of a personal home hemodialysis ("HHD") system having a mobile cart and integral bag manager.

Referring now to the drawings, FIG. 1 illustrates one embodiment of a system 10 sitting idle with its dust cover (not illustrated) removed. A handle 12 for a cart 14 is located in a lowered position to minimize the space that system 10 consumes. Shelves 16 for the supply bags (shown below) are also shown in a lowered or "down" position, which minimizes the height of system 10.

Figure 2:
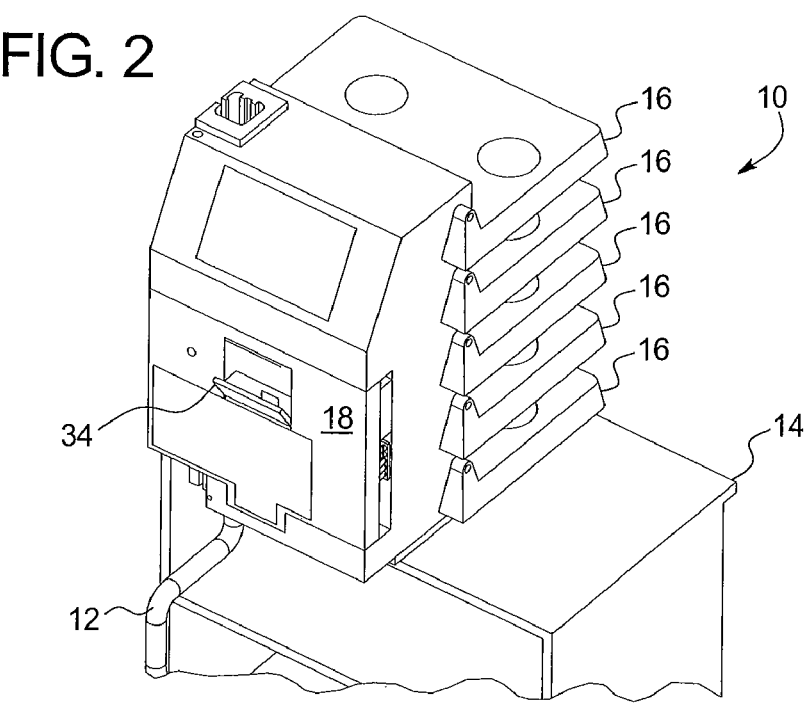
FIG. 2 illustrates the system of the present disclosure, in which a latch is pulled out to unlock a door.

System 10 is programmed in an introductory state to instruct the user to open a door 18 shown in FIG. 2. FIG. 2 illustrates a close-up view of system 10 with a latch 34 pulled out to unlock door 18. Once door 18 is unlocked as seen in FIG. 3, it swings open, e.g., about forty-five degrees, and is held in the open position by a stop (not seen), so that a disposable set (shown below) can be loaded or unloaded.

Figure 3:
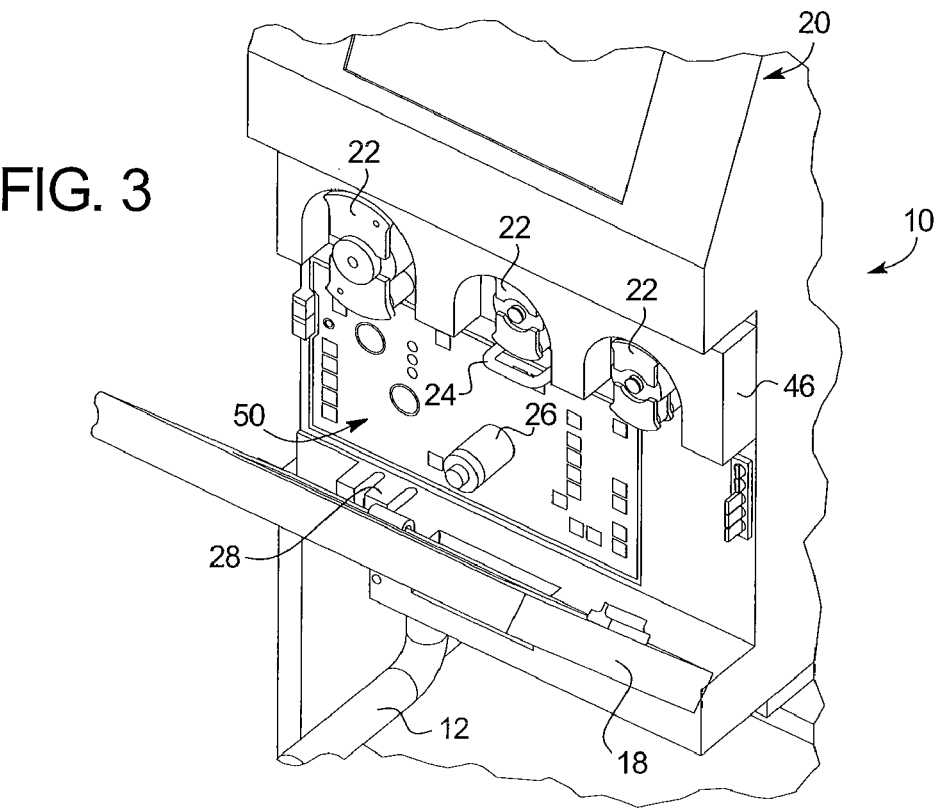
FIG. 3 illustrates the system of the present disclosure, in which a door is opened exposing a latch hook and peristaltic pump heads.
Figure 16:
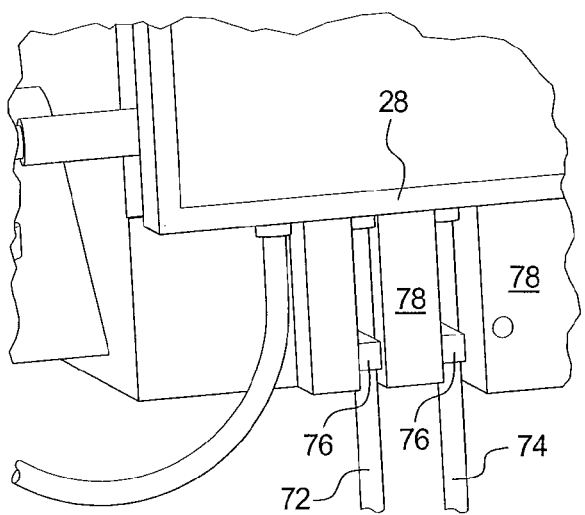
FIG. 16 illustrates blood line clamps closed on the blood lines of FIG. 15.

FIG. 3 illustrates instrument 20 of system 10 with door 18 held in the open position, exposing multiple peristaltic pump heads 22, a latch hook 24, inductive heater coil 26 and a slotted area 28 for the blood lines (not illustrated) to run to and from the patient. Ultrasonic air bubble detectors and optical blood/saline/air detectors are integrated into the molded slotted area 28 just above a cutout in the slot for the venous and arterial line clamps. The cutout located in slotted area 28 accommodates the venous and the arterial line clamps. FIG. 16 shows the venous and arterial line clamps 76 in the closed position, in which the clamps extend through a respective cutout. In an alternative embodiment, the inductive heater coil 26 is retracted into the system to facilitate loading.

Figure 4:
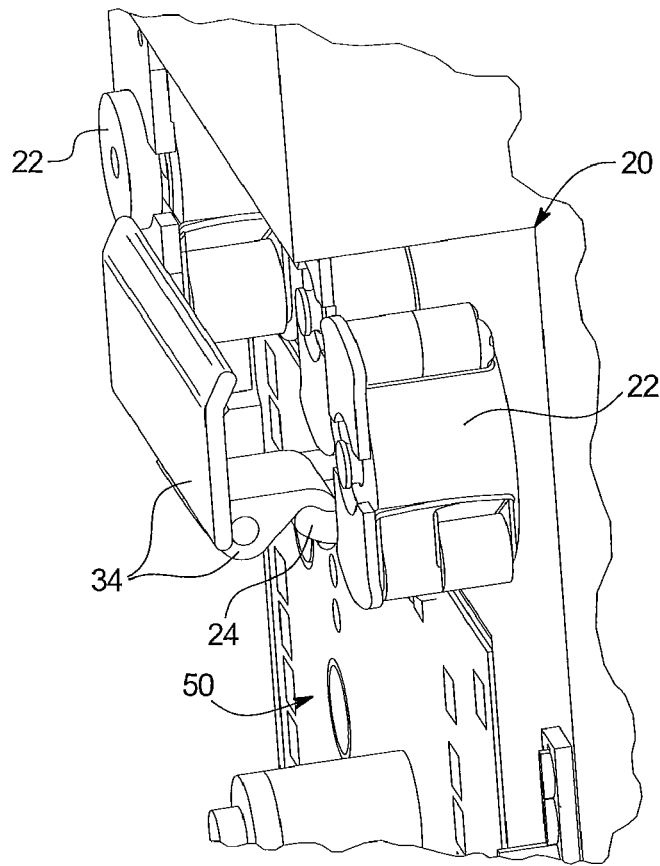
FIG. 4 illustrates one embodiment of the system of the present disclosure, in which the door is hidden to more clearly show the door latch.

In FIG. 4, door 18 is not shown for clarity to illustrate latch 34 and latch hook 24, wherein latch 34 mechanically engages latch hook 24 to hold door 18 closed against the main portion of instrument 20. One suitable latch assembly is shown and described in FIGS. 11 and 13 of U.S. Pat. No. 6,261,065, "System and Methods for Control of Pumps Employing Electrical Field Sensing", the pertinent portions of which are incorporated herein expressly by reference.

Figure 5:
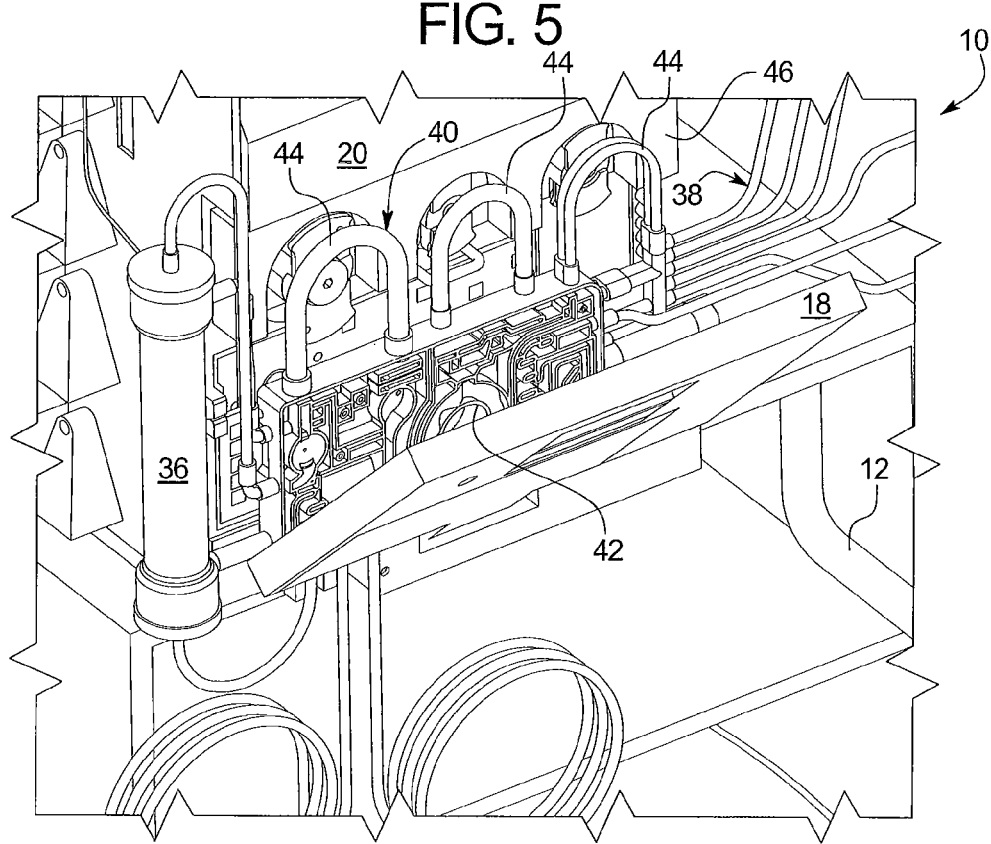
FIG. 5 illustrates one embodiment of the system of the present disclosure, in which a disposable unit is loaded from above and slid to the right.

As seen in FIG. 5, once door 18 has been opened, system 10 prompts the user to load the disposable set. A cassette 40 of the disposable set is lowered into instrument 20 and moved to the right (with respect to the orientation of instrument 20 in FIG. 4). Cassette 40 is loaded starting at the upper left side of open door 18, so that the patient's blood lines extending downwardly from cassette 40 do not interfere with the loading procedure. The patient's left hand can grasp a dialyzer 36 connected to cassette 40, while the patient's right hand can grasp a tubing bundle 38 formed by the supply and drain lines. Single handed loading is also possible, e.g., using right hand only grasp bundle 38 to move both cassette 40 and dialyzer 36.

Figure 6:
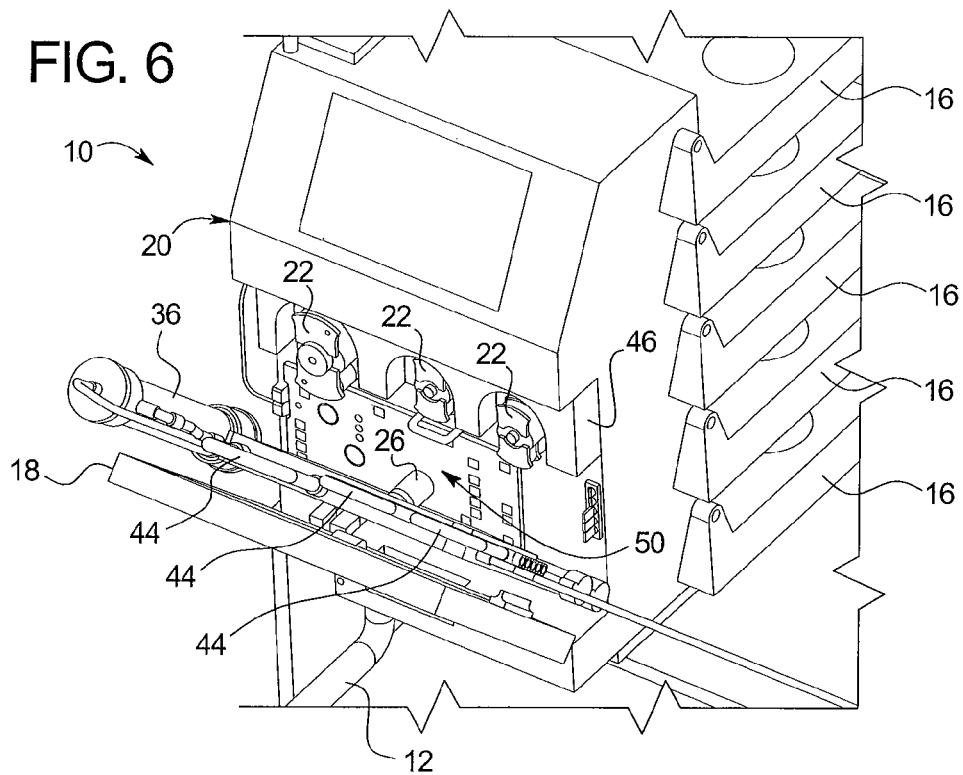
FIG. 6 illustrates one embodiment of the system of the present disclosure, in which the disposable unit is pivoted forward towards the interface.
Figure 7:
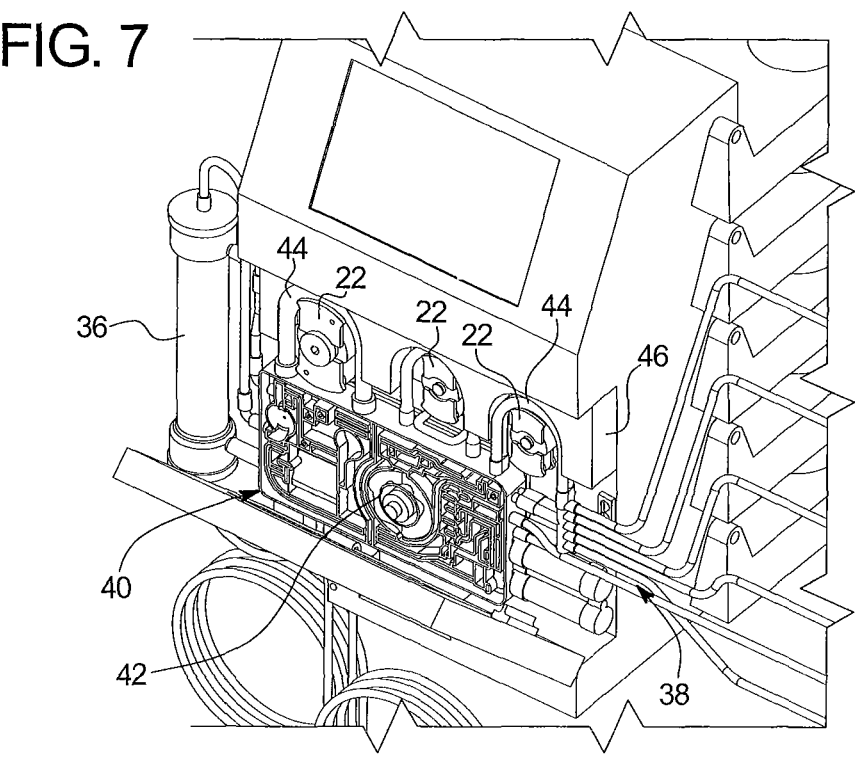
FIG. 7 illustrates one embodiment of the system of the present disclosure, in which the disposable unit pivots forward and the tube loops fit over the peristaltic pump heads.

As seen in FIGS. 6 and 7, door 18 pivots cassette 40 forward towards a cassette interface 50 of instrument 20 when an opening 42 in cassette 40 is located directly over the inductive heater transformer coil 26. In an alternative embodiment, transformer coil 26 is retracted to facilitate loading of cassette 40. In such case, coil 26 is then extended into operating position after cassette 40 is loaded against interface 50. A bezel (not shown) provides locating stops for stopping cassette 40 in the vertical and horizontal directions.

As cassette 40 mates with the cassette interface 50, the peristaltic pump tubing loops 44 of cassette 40 slip over the vertically aligned pumping heads 22. A pump race 46 is retracted automatically upwardly when door 18 is opened to provide clearance between the pump heads 22 and pump race 26 to facilitate the loading of pump tubing 44 and cassette 40.

Figure 8:
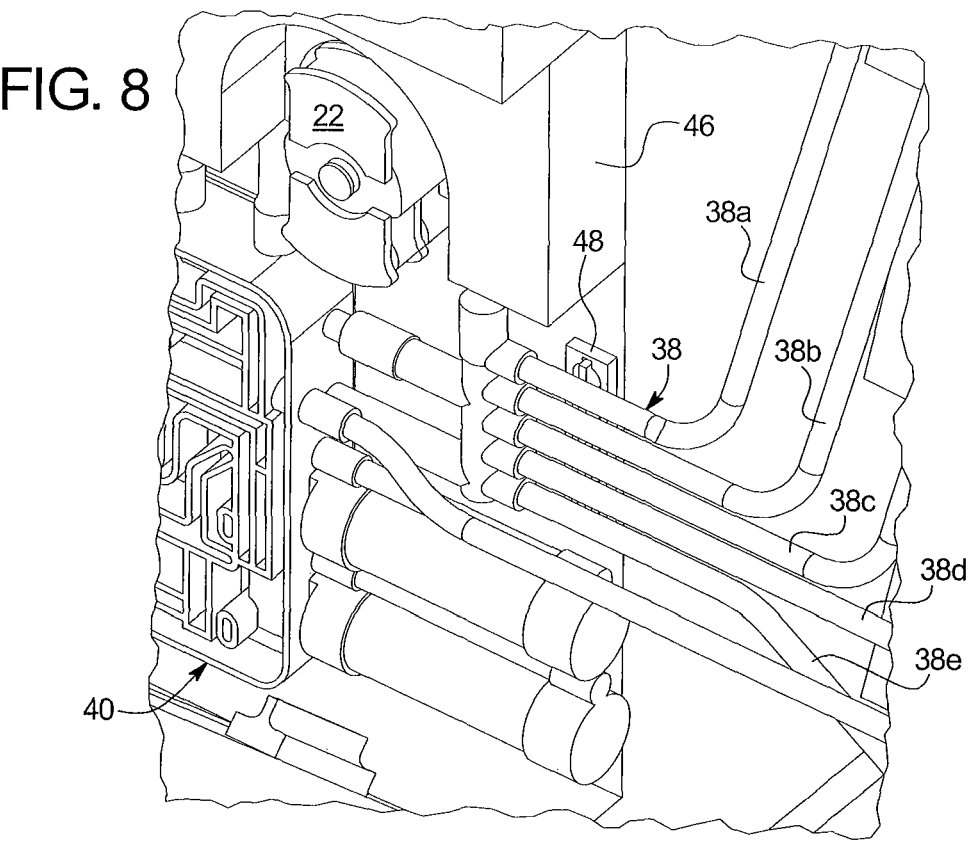
FIG. 8 illustrates one embodiment of the system of the present disclosure, in which the supply lines are placed in operable communication with individual pinch valve plungers.
Figure 9:
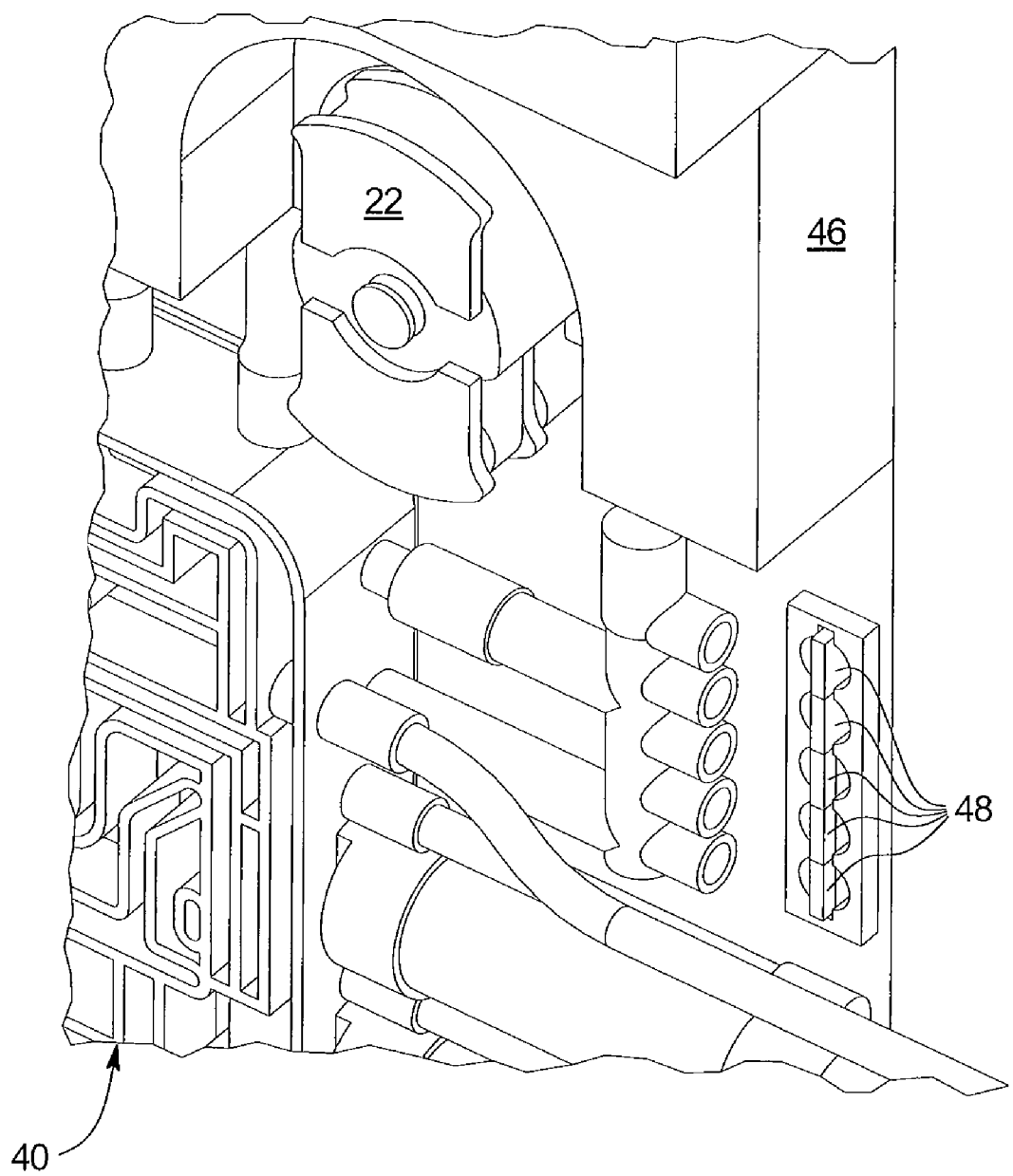
FIG. 9 illustrates one embodiment of the system of the present disclosure, in which the supply lines are hidden to show pinch valve plungers.

FIG. 8 illustrates the supply lines 38a to 38e of bundle 38 (number of supply lines 38 can vary) passing over retracted pinch valves 48. System 10 also retracts pinch valves 48 automatically when door 18 is opened to facilitate the loading of bundle 38 and cassette 40 against interface 50 of instrument 20. System 10 opens and closes pinch valves 48 in a controlled manner, eliminating the need for manual clamps on supply lines 38a to 38e. FIG. 9 is shown with supply lines 38 removed to more clearly illustrate pinch valve plungers 48.

Figure 10:
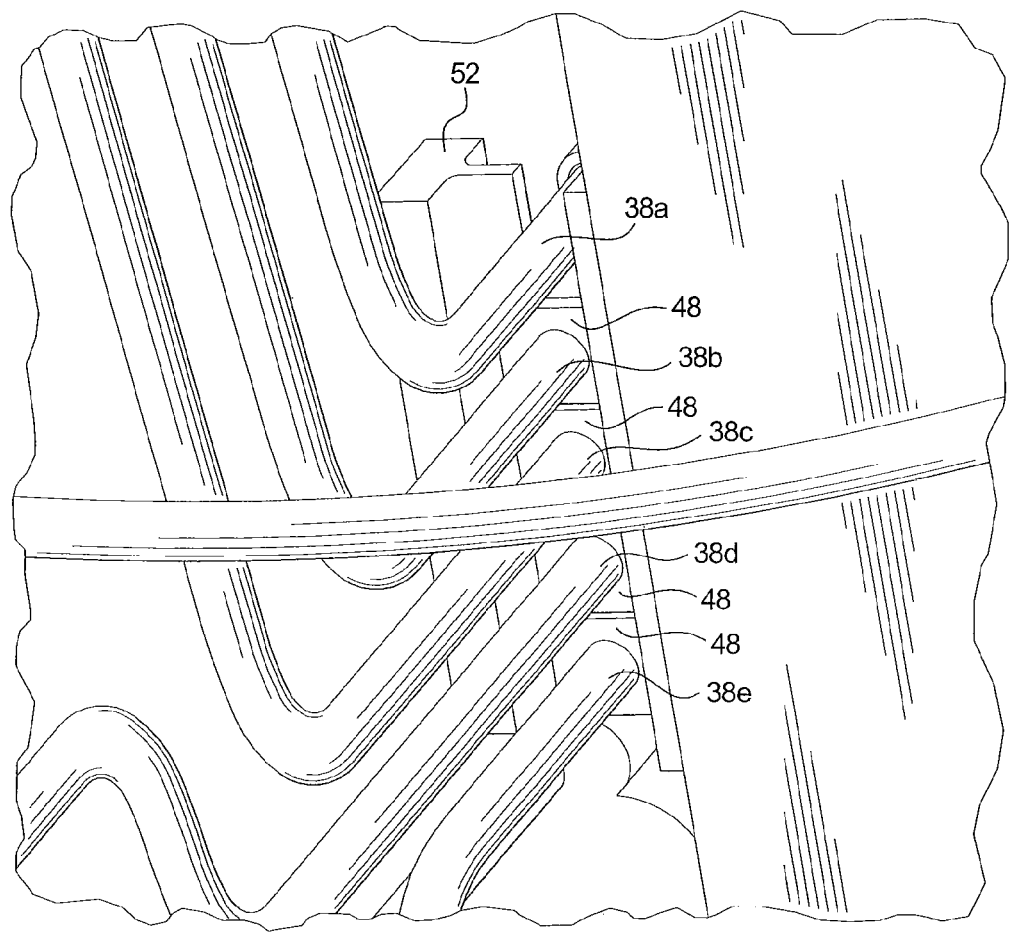
FIG. 10 is rear view of one embodiment of the system of the present disclosure showing a pinch valve strike plate.

FIG. 10 further illustrates pinch valve 48/supply line 38 interaction. Pinch valves 48 pinch supply lines 38 closed against a strike plate 52. In FIG. 10, four pinch valves 48 for supply lines 38b to 38e are pinching a respective supply line closed against strike plate 52, while a fifth pinch valve 48 is retracted, allowing supply line 38a to be open.

Figure 11:
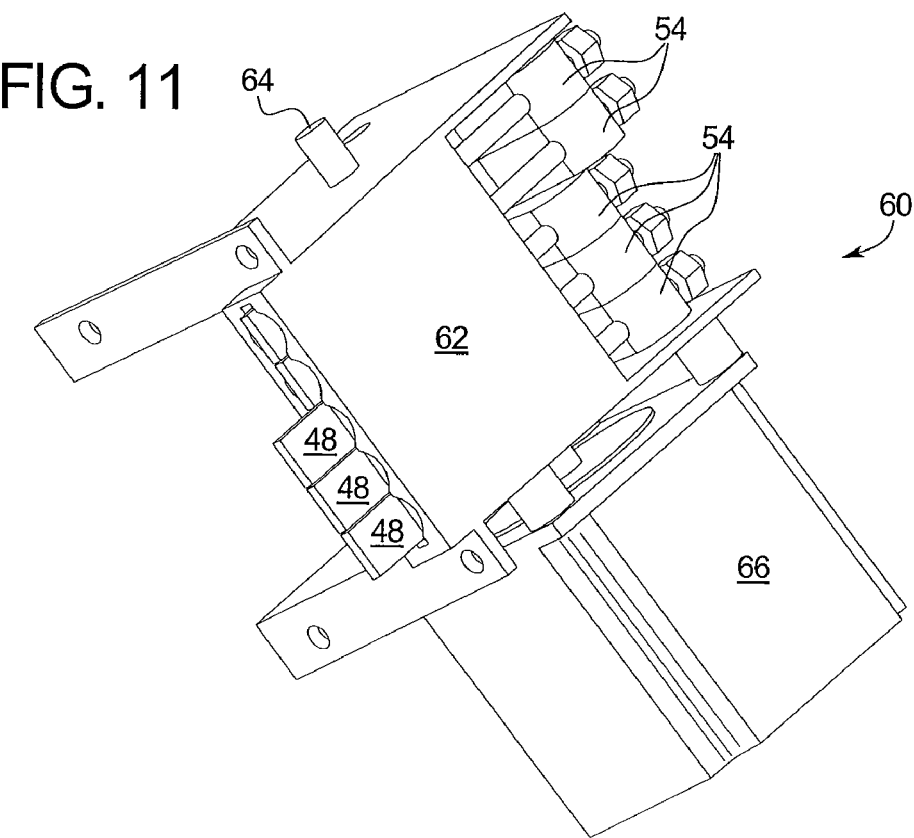
FIG. 11 is a perspective view of one embodiment of a cam operated pinch valve subassembly operable with the system of the present disclosure.
Figure 12:
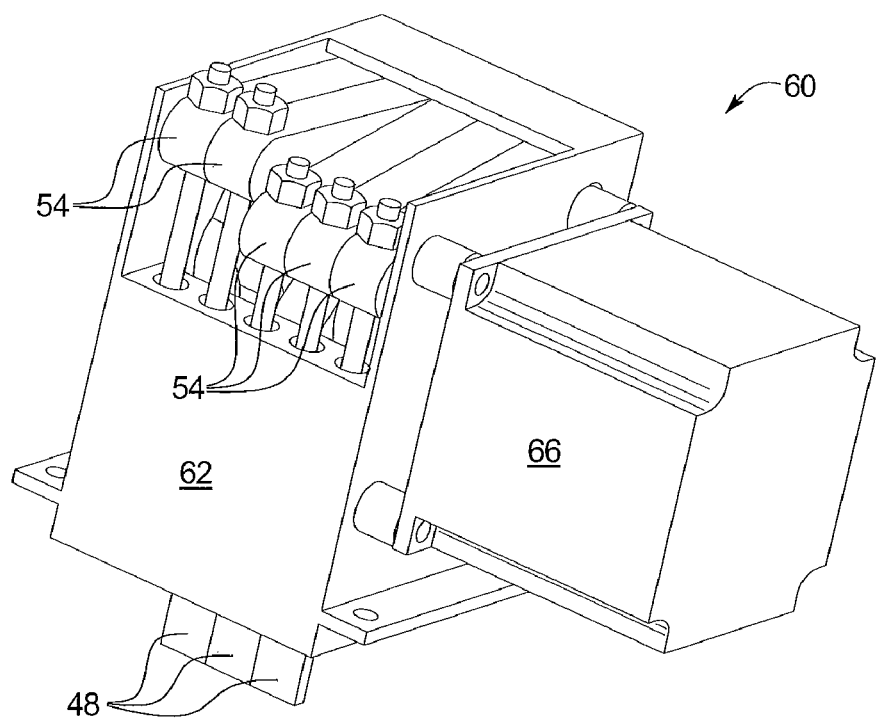
FIG. 12 is another perspective view of the pinch valve subassembly of FIG. 11.
Figure 13:
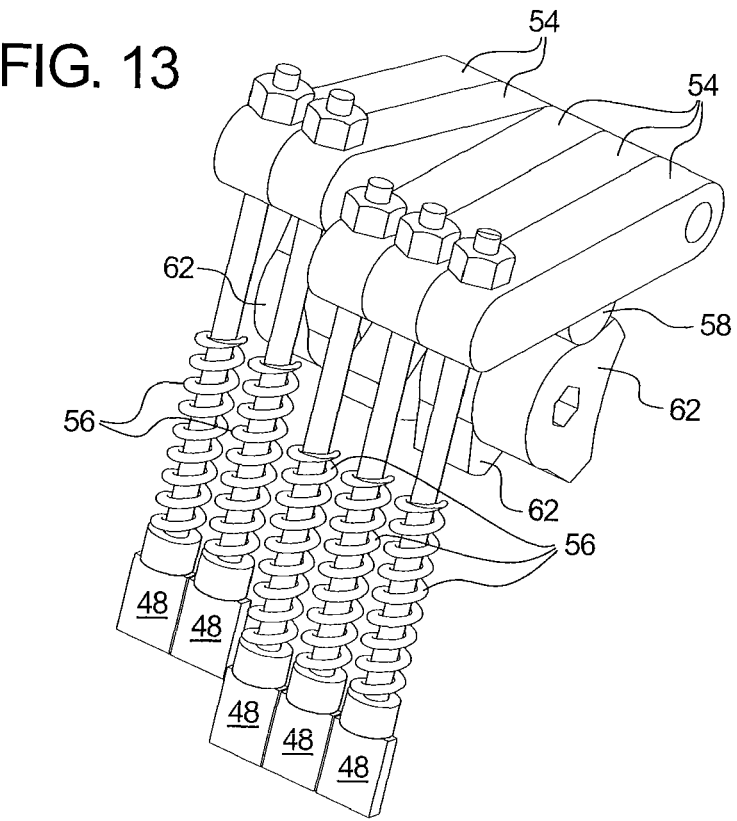
FIG. 13 is a perspective view of the pinch valve subassembly of FIG. 11 with its housing and motor hidden.
Figure 14:
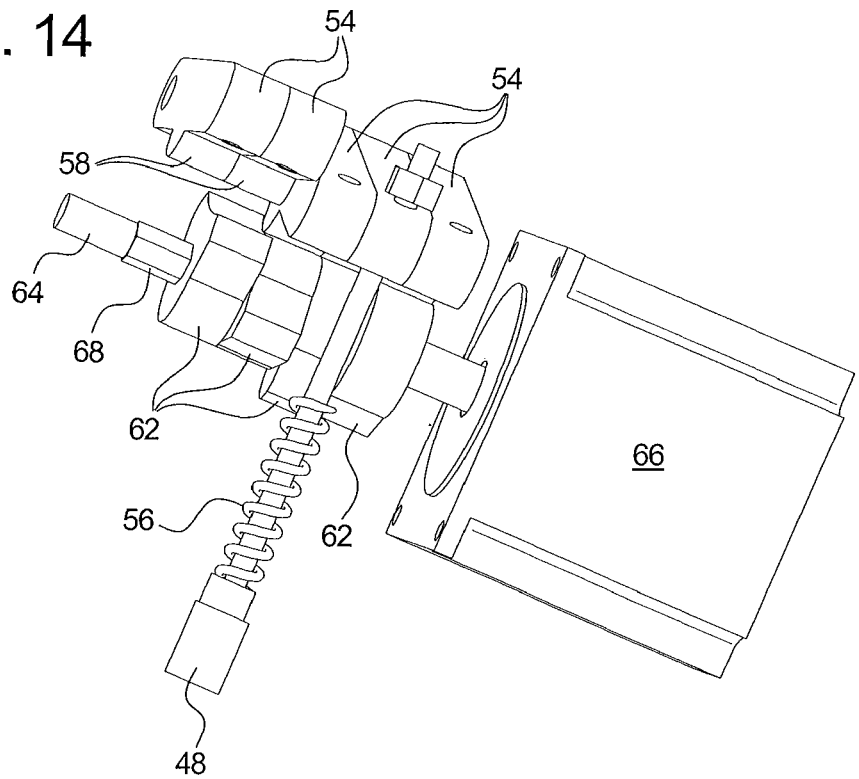
FIG. 14 illustrates a stepper motor operating with the pinch valve subassembly of FIG. 11.

FIGS. 11 and 12 illustrate a pinch valve subassembly 60, in which three of the five plungers 48 are extended (closed state). Clamp heads 54 are connected to a pinch valve body 62 of subassembly 60. FIG. 13 is shown with body 62 removed to illustrate springs 56 that spring load pinch valve plungers 48, e.g., so as to be normally closed. Springs 56 preload pinch valve plungers 48, allowing for variations in the wall thickness of supply tubes 38. FIG. 13 also illustrates that clamp heads 54 are formed with cam followers 58, which ride on associated cam lobes 62 coupled to a camshaft 64 (FIGS. 11 and 14). A motor 66, e.g., a stepper motor, is coupled to a drive camshaft 64. FIG. 14 illustrates that in one embodiment, the individual cam lobes 62 each define apertures configured fit onto a keyed portion 68 of shaft 64. FIG. 14 further illustrates the interaction of cam followers 58 and cam lobes 62.

Figure 15:
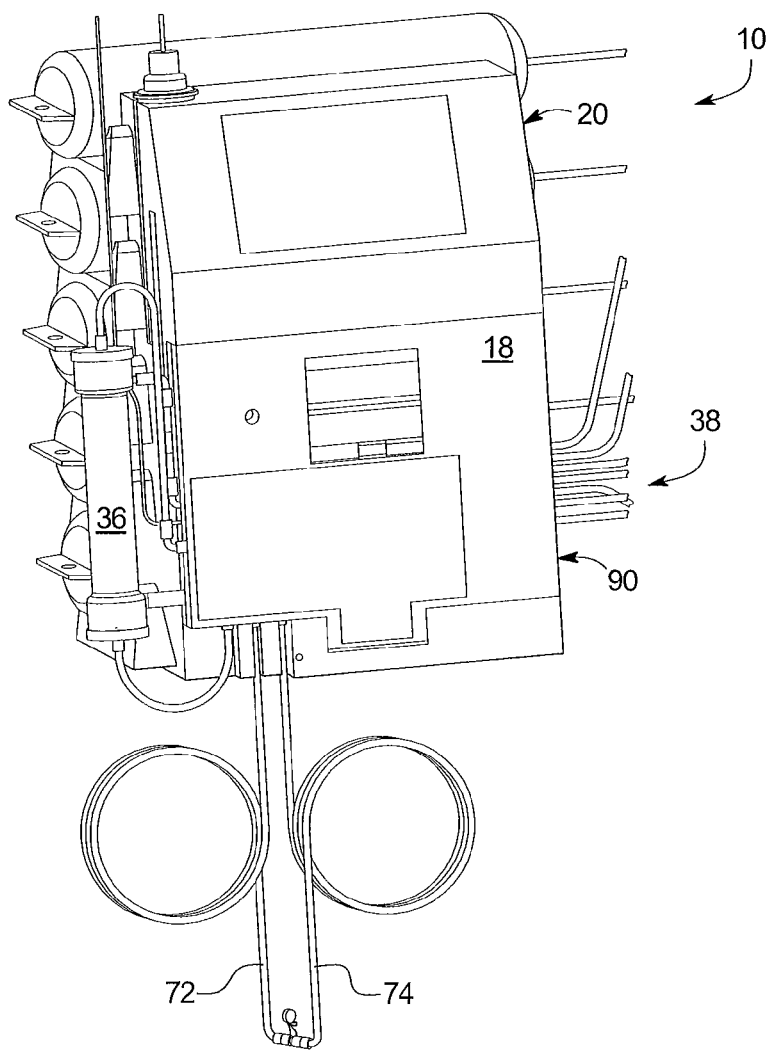
FIG. 15 illustrates blood lines operable with the system of FIG. 1.
Figure 17:
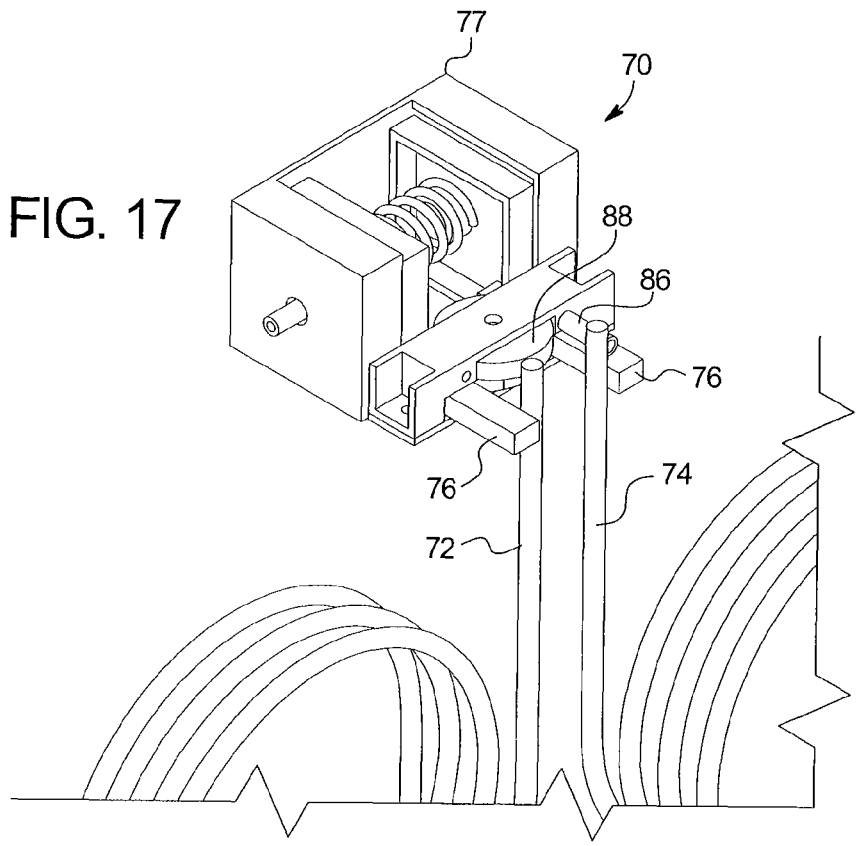
FIG. 17 illustrates one embodiment of a blood line clamp subassembly operable with the system of the present disclosure.

FIG. 15 illustrates that when cassette 40 is loaded into instrument 20 of system 10, blood lines 72 and 74 exit to the lower left of door assembly 90 with venous and arterial line clamps 76 (FIG. 16) open initially. FIGS. 16a and 16b illustrate that venous and arterial line clamps 76 pinch bloodlines 72 and 74 against housing portion 78 of instrument 20 to close bloodlines 72 and 74. During normal operation, system 10 operates clamps 76 independently as needed. FIG. 17 is shown with housing portion 78 and door assembly 90 removed to more fully illustrate venous and arterial line clamp subassembly 70. A strike part of housing portion 78 seen in FIG. 16 is located between the venous and arterial lines 72 and 74 and pinches the lines together with the clamping levers 76 when closed.

Figure 18:
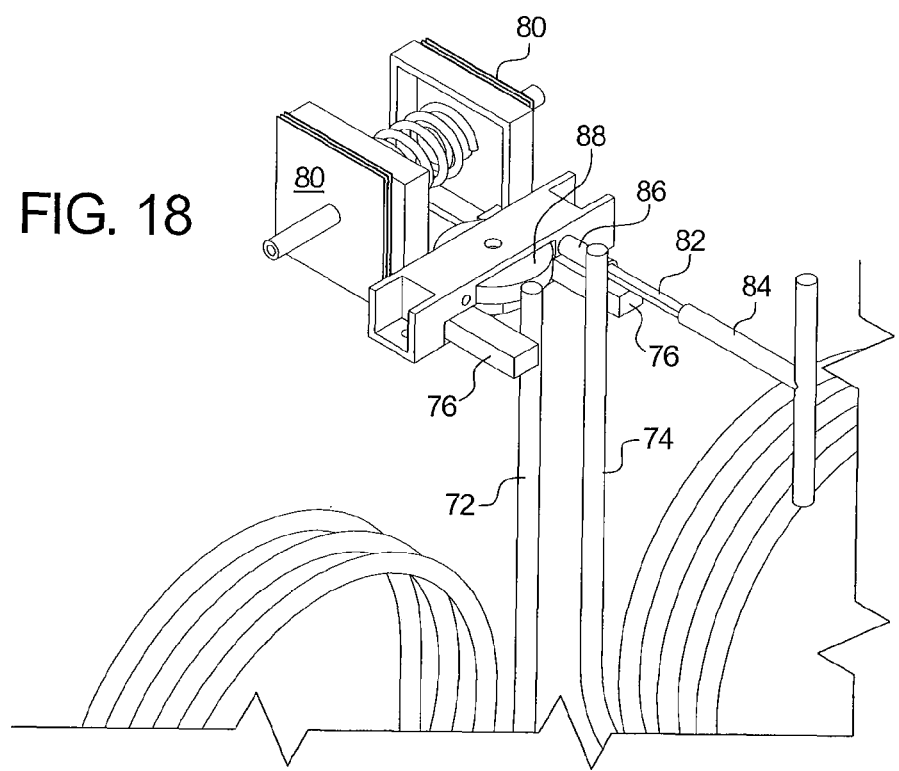
FIG. 18 illustrates one embodiment of a blood line clamp manual override.
Figure 19:
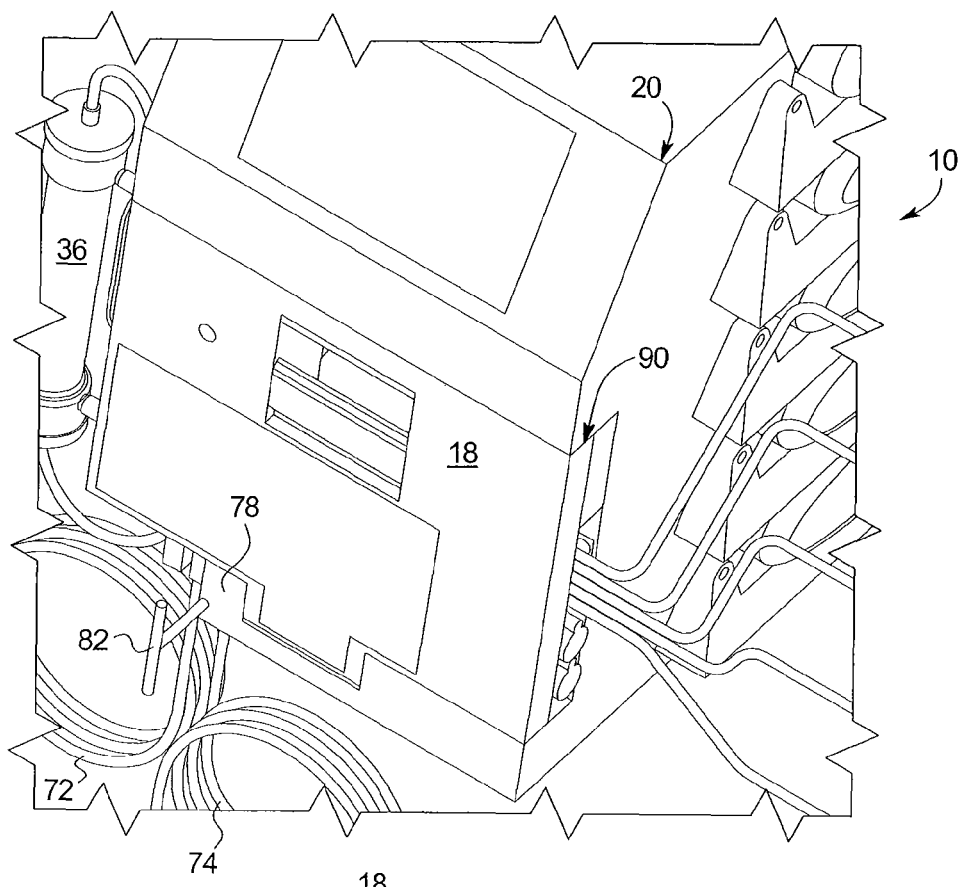
FIG. 19 illustrates a user access to a manual override of the blood line clamps.

FIG. 18 illustrates the venous and arterial line clamp subassembly 70 less a housing 77 shown in FIG. 17, in which clamps 76 are in the open position. Subassembly 70 includes bellows 80 that hold clamps 76 open during normal operation. Subassembly 70 also allows for an Allen wrench 82 with a T-handle 84 to be used to operate a worm gear 86 that is coupled operably to a cam 88, which cooperate to manually open both the venous and arterial line clamps 76 if need be. In an alternative embodiment, subassembly 70 includes dual worm gears and a split cam, so that the venous and arterial line clamps 76 can be manually operated independently. FIG. 19 illustrates the placement of the T-handle Allen wrench 82 with respect to instrument 20 when the venous and arterial line clamps 76 are operated manually. In one embodiment, system 10 causes an, e.g., red, flag (not illustrated) to protrude when the clamps 76 have been opened manually. The flag retracts when the manual override is not engaged.

Figure 20:
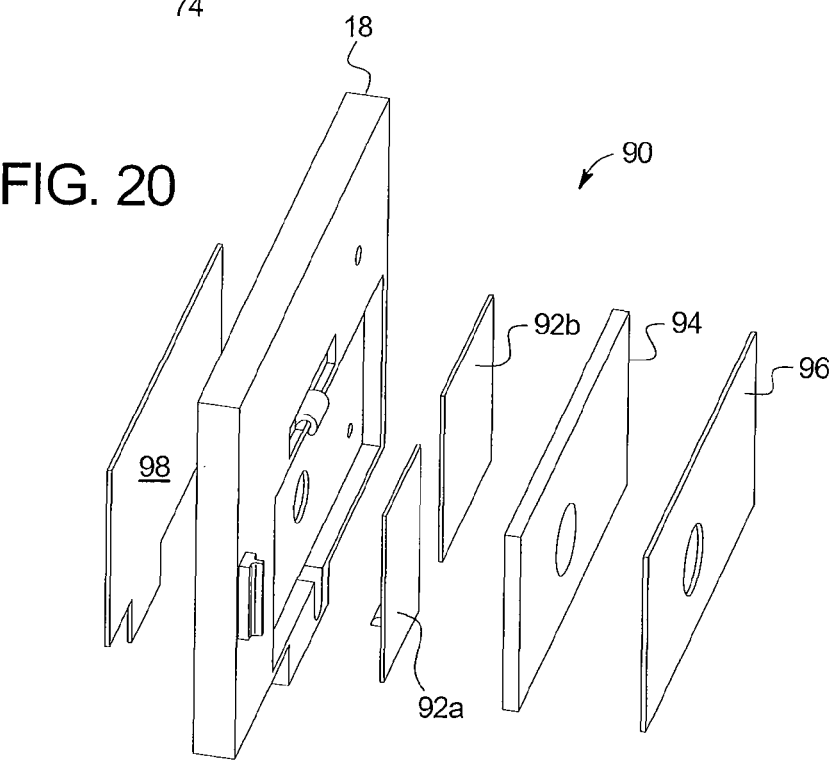
FIG. 20 is a perspective exploded view of one embodiment of a door showing a pressure plate, gasket and bellows operable with the system of the present disclosure.

FIG. 20 illustrates an exploded view of the door assembly 90 taken from inside instrument 20. A pair of bellows or bladders 92a and 92b pushes a plate 94 having a gasket 96 to press the cassette 40 (not seen here) against the disposable interface 50 (not seen here). A space between bladders 92a and 92b is provided to accommodate the inductive heater coil 26 extending from disposable interface 50. Alternatively, instrument 20 provides a single bellows (bladder) to press cassette 40 against the disposable interface 50, which has an internal opening to accommodate heater coil 26 extending from disposable interface 50.

In an alternate failsafe embodiment (not illustrated), the bellows 92a and 92b are replaced by a cavity with a diaphragm that is connected sealably to front pressure plate 18. Springs are located between front pressure plate 18 and the back wall of the cavity and press cassette 40 against disposable interface 50, except when a vacuum is present within the cavity. In the alternative embodiment, system 10 can also introduce positive pressure into the cavity to increase the sealing force.

Figure 21:
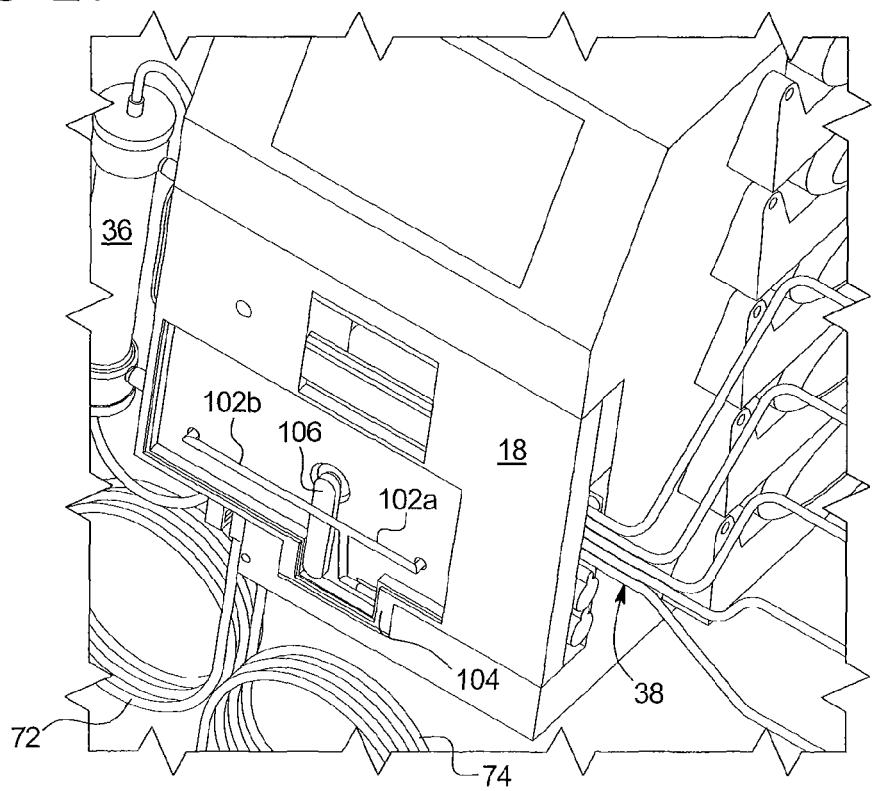
FIG. 21 illustrates the system with a door cover removed exposing tubes for bellows.
Figure 22:
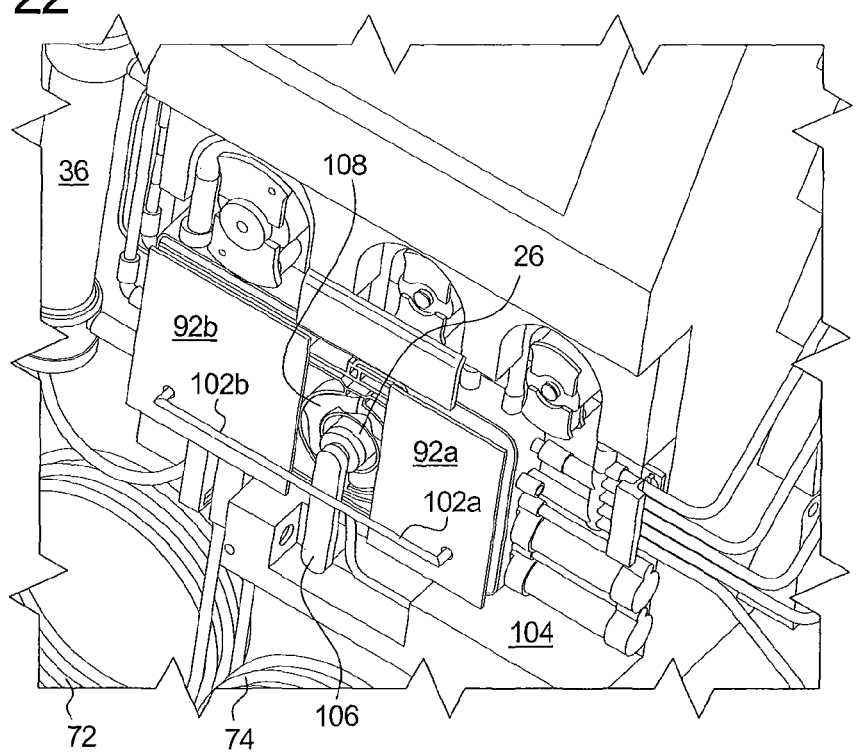
FIG. 22 illustrates the system with the door hidden to better show an inline heating system.
Figure 23:
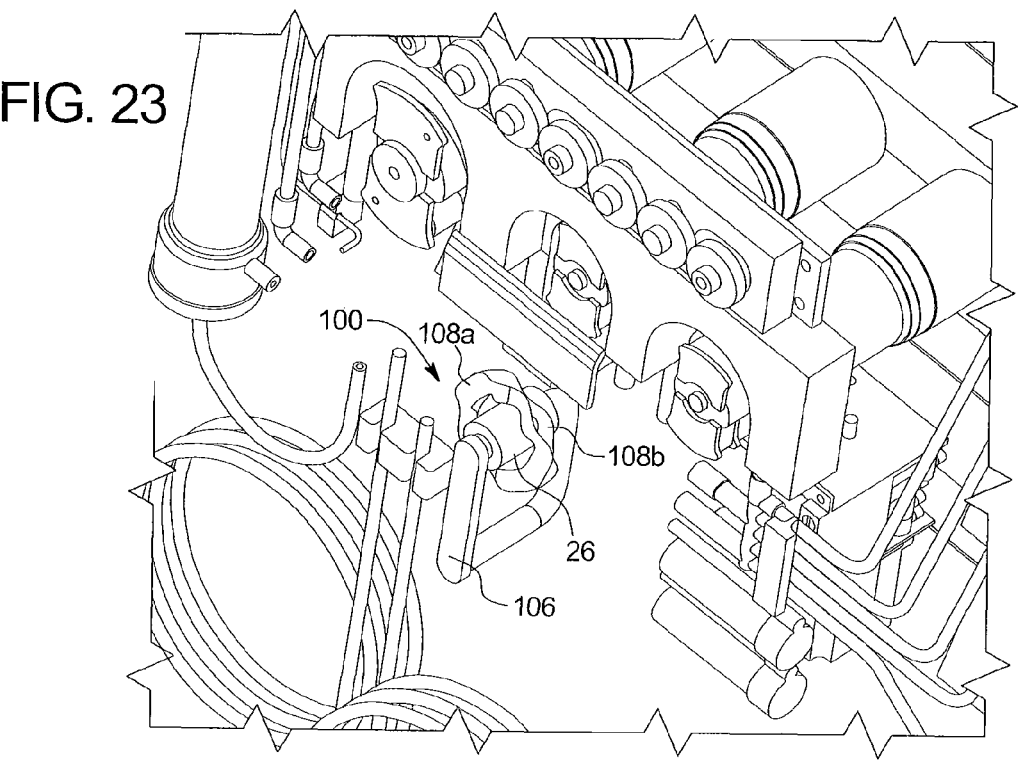
FIG. 23 illustrates the system with the door and cassette hidden to better show a heater coil and wave heater disks.

FIG. 21 illustrates system 10 with the door cover 98 (FIG. 20) removed. Pneumatic lines 102a and 102b to bellows 92a and 92b, respectively, are shown teed together before exiting door 18 through a hollow hinge 104. A vertical metal bar 106 completes a circuit for the inductive heater transformer primary coil 26 when the door 18 is closed against interface 50 of instrument 20. FIG. 22 is also shown with door 18 removed to illustrate the inductive heating system including transformer coil 26 and a wave-shaped disk or disks 108 located in disposable cassette 40, which form a secondary coil that heats dialysis fluid due to $i^2R$ losses. FIG. 23 removes cassette 40 to show inductive heater 100 more clearly. Heater 100 transfers energy from the inductive coil of the transformer 26 into wave washers 108a and 108b that are located within cassette 40. Washers 108a and 108b in turn heat dialysate as it flows through cassette 40.

Figure 24:
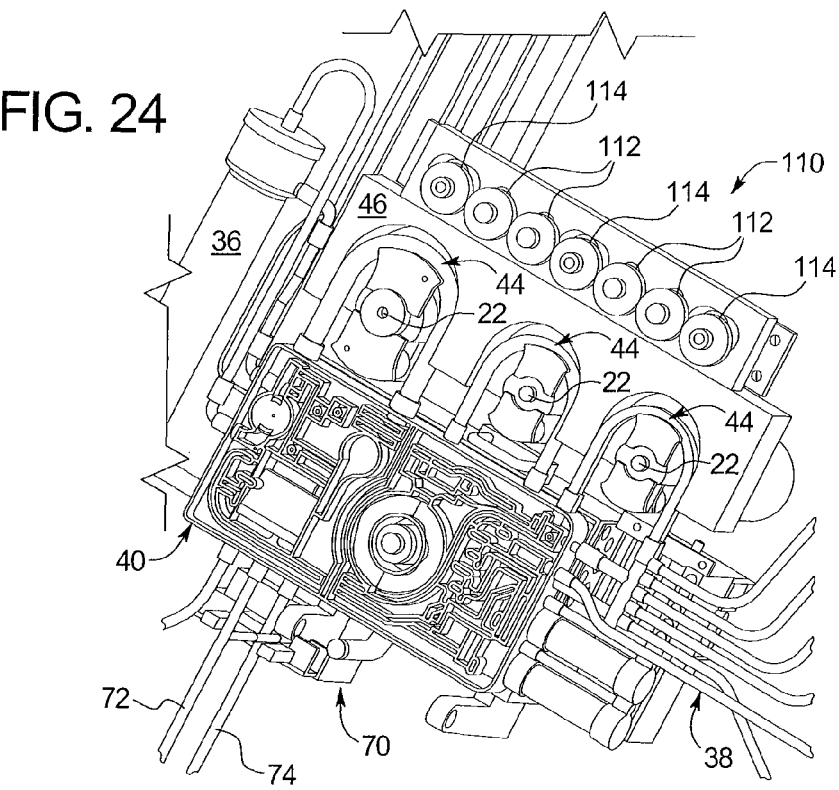
FIG. 24 illustrates a front view of a retracted peristaltic pump race of the system of the present disclosure.

FIG. 24 illustrates the front of the instrument 20 with door assembly 90 and device housing hidden to expose a mechanism 110 that extends and retracts triple peristaltic pump race 46. Mechanism 110 includes four idler gears 112 that tie geared triple cams 114 together to move race 46 to extend (towards tubing 44) and retract (from tubing 44) smoothly. Mechanism 110 is configured such that race 46 extends towards tubing 44 only after door 18 is closed and latched to preclude the operator from being exposed to any moving components. The centers of pump heads 22 are aligned to provide clearance between the pump heads and triple race 46 when the race is retracted.

Figure 25:
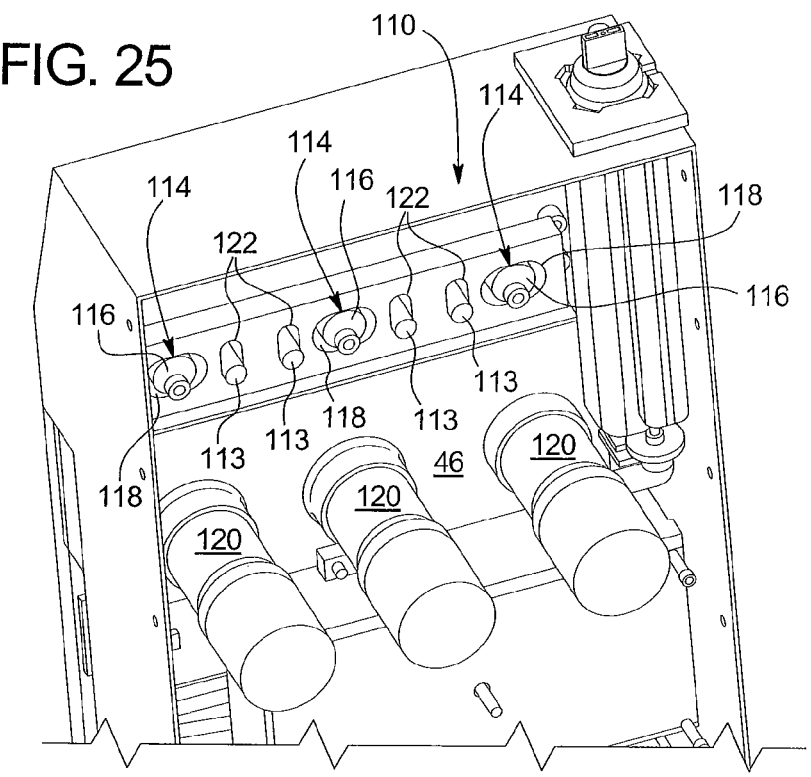
FIG. 25 illustrates a rear view of a retracted peristaltic pump race.

FIG. 25 illustrates the backside of the retractable triple peristaltic pump race 46 and mechanism 110 for moving race 46. Cams 114 are located at each end of race mechanism 110 and race 46. A middle cam 114 is also provided. Each idler gear 112 (FIGS. 24 and 27) includes a shaft 113 that transmits rotational motion from the idler gears to all three cams 114 simultaneously. Cams 114 each include lobes 116 that rotate simultaneously and in concert within large rounded end slots 118 to simultaneously and evenly extend and retract race 46. Shafts 113 of idler gears 112 (FIG. 24) maintain the horizontal orientation of the peristaltic pump race 46 as the race moves up and down.

Figure 26:
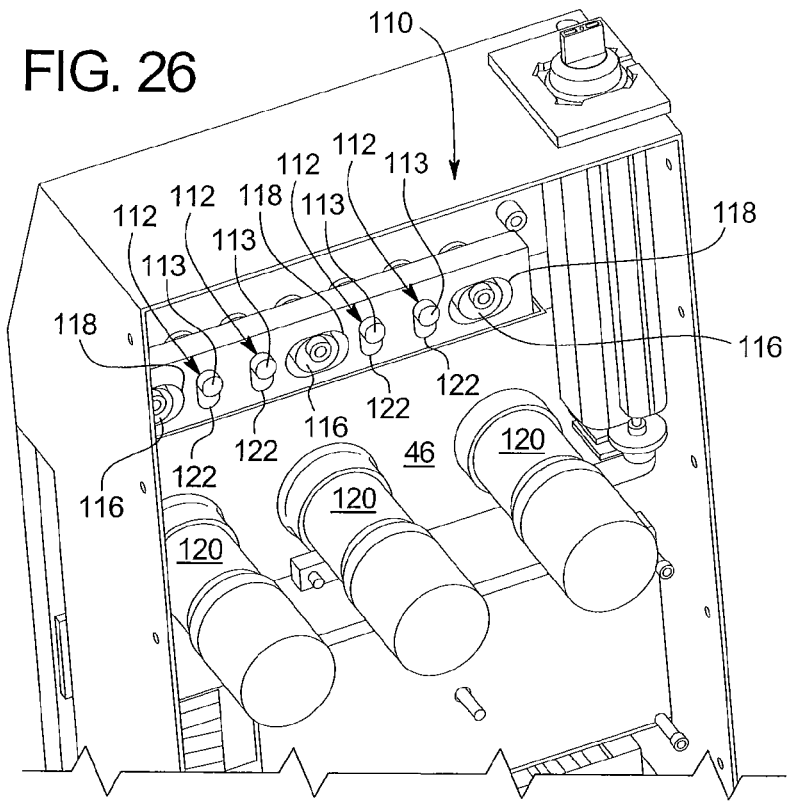
FIG. 26 illustrates a rear view of the peristaltic pump race extended.

FIG. 25 illustrates the cam lobes 116 rotated simultaneously and in concert upwardly, pushing the pump race 46 away from gear motors 120 that are coupled to pump heads 22. The open parts of the horizontally stabilizing idler guide slots are above the shafts 113 of idler gears. FIG. 26 illustrates the cam lobes 116 rotated simultaneously and in concert downwardly, pushing pump race 46 towards the pump gear motors 120 coupled to pump heads 22. The open parts of the horizontally stabilizing idler guide slots 122 are now below the shafts 113 of idler gears 112.

Figure 27:
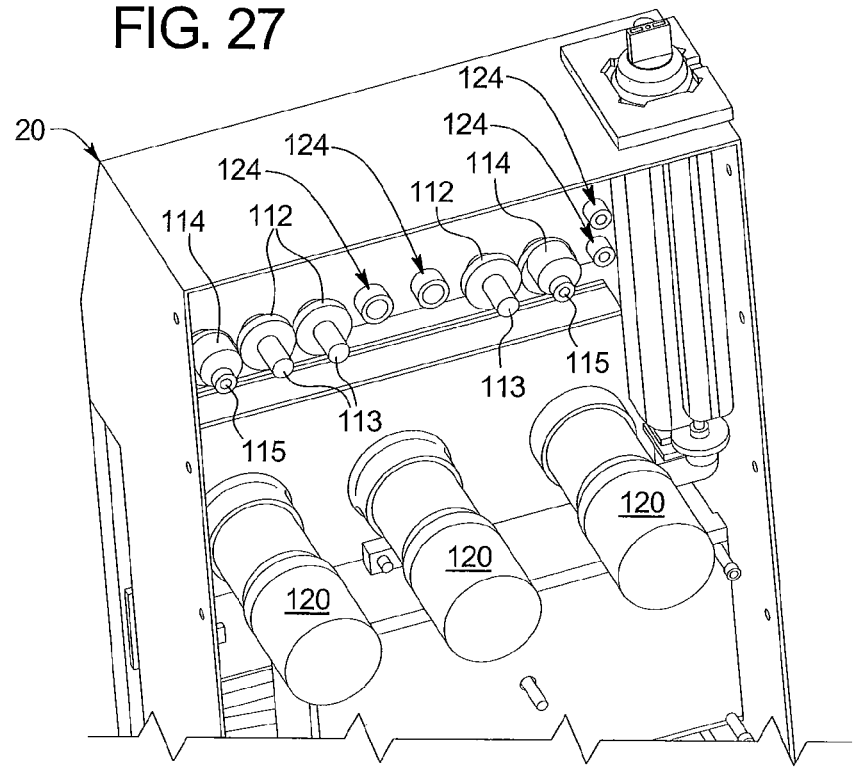
FIG. 27 illustrates that an instrument housing supports the front of the pump race actuator shafts.

FIG. 27 illustrates molded support bosses 124 secured to instrument 20 that support shafts 113 of the idler gears 112 and support the shafts 115 of cams 114 on one end. A bar (not shown here but shown in FIG. 71), which mounts to bosses 124, supports the shafts 113 of gears 112 and shafts 115 of cams 114 on their other ends. A motor (not illustrated) drives cams 114, which operate the retractable pump race 46, and is attached to any of the shafts 115 of any of cams 114. Attaching the motor to the shaft of center cam 114 may be preferred so that clearance in the gear train is symmetric with respect to outer cams 114.

Figure 28:
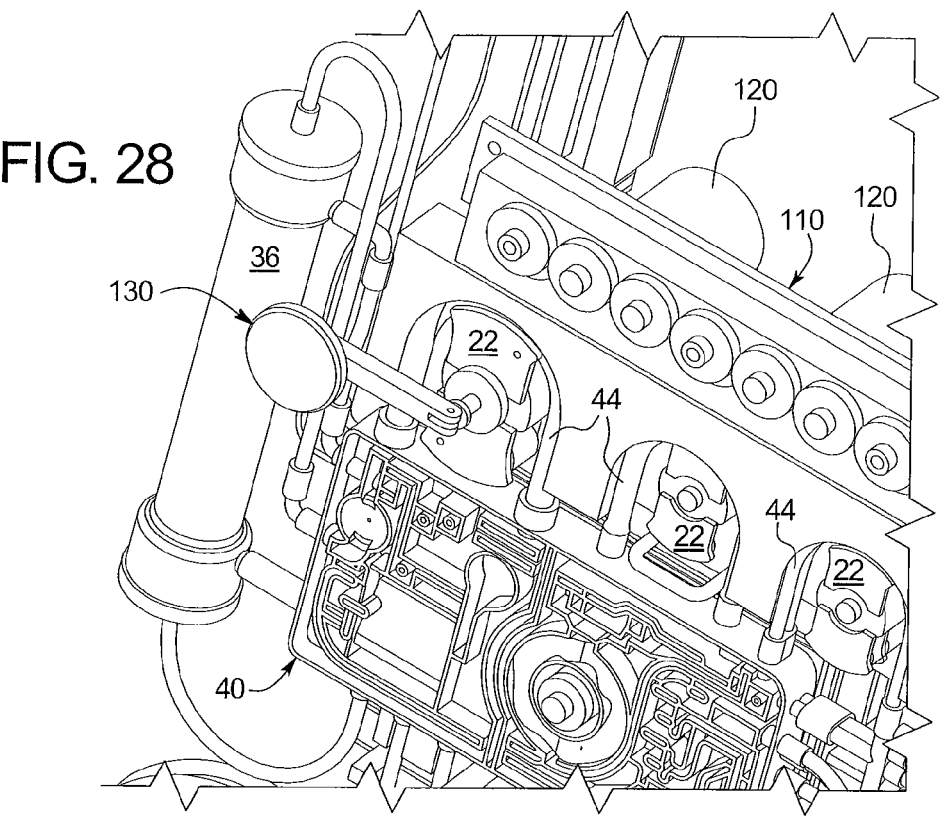
FIG. 28 illustrates one embodiment of a manual blood pump operation of the system of the present disclosure.
Figure 29:
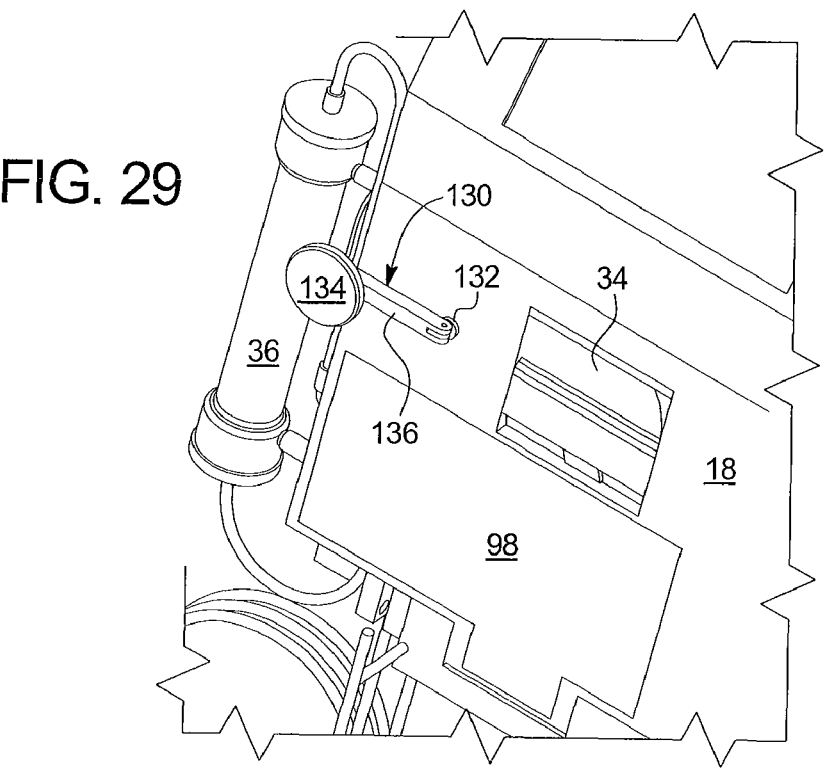
FIG. 29 illustrates a manual blood pump operation with the instrument door closed and latched.

FIGS. 28 and 29 illustrate that system 10 includes a crank 130 that is connected to the blood pump head 22 to operate the head manually. Manual return of the blood contained within the extracorporeal circuit is necessary in the event of a failure of system 10 or after an extended power failure. It is typically necessary to manually operate the venous and arterial line clamps 76 (from a failed closed state) before being able to return the blood in the extracorporeal circuit to the patient. FIG. 29 also illustrates that door 18 in one embodiment defines an opening or aperture 132 through which manual crank 130 for the blood pump 22 can be inserted with the door closed. Crank 130 includes a large gripping handle 134 and crankshaft 136, which is sufficiently long to allow the user to easily turn blood pump head 22. In an alternate embodiment, manual crank 130 is built into the door assembly 90 and is accessible to engage pump head 22 when door 18 is opened and hinged away from machine interface 50.

Figure 30:
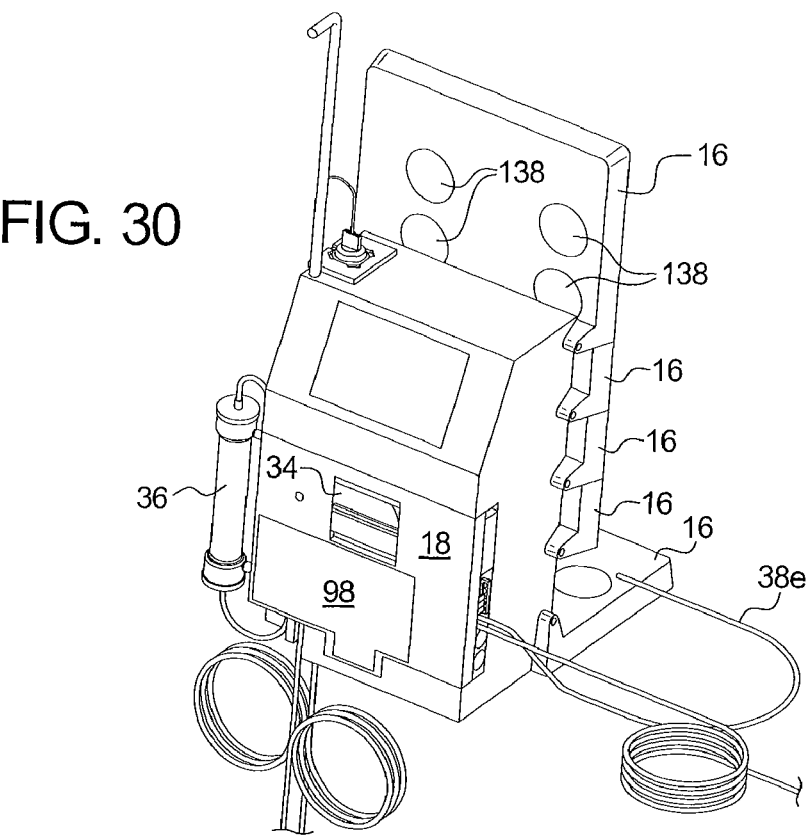
FIG. 30 illustrates one embodiment of a bag management system operable with the HHD system having shelves folded up and ready for placement of a first supply bag.
Figure 31:
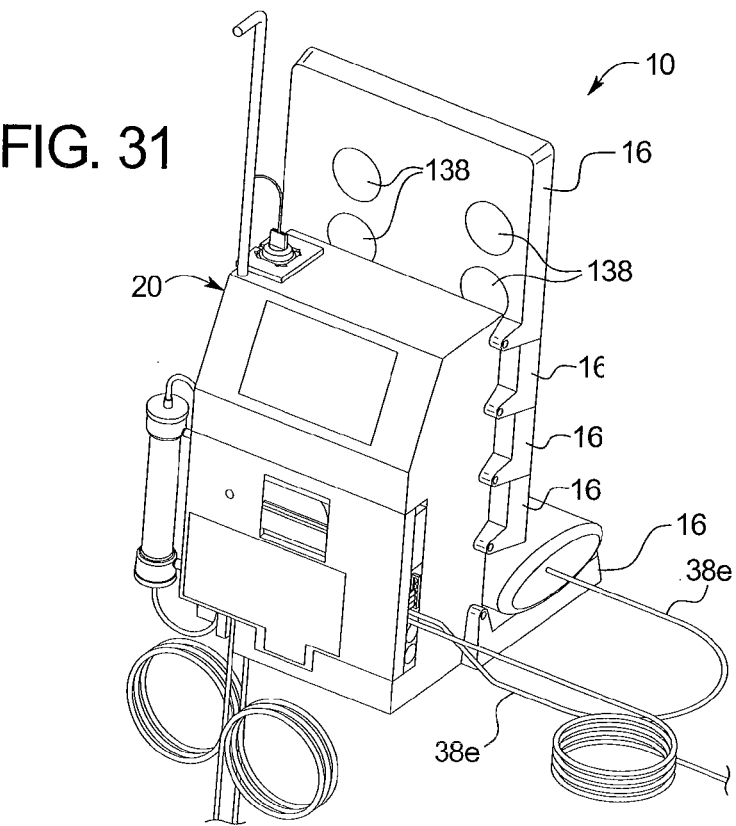
FIG. 31 illustrates a supply bag placed on a bottom shelf of the bag management system.

As seen in FIG. 30, in one bag management embodiment, system 10 prompts the user initially to fold up all of bag shelves 16 except for the bottom shelf 16. The user is then able to break a peel seal of a dual chamber bag (if used), place the first solution bag 140 on bottom shelf 16 and connect the bag to the bottom supply line 38e extending from disposable cassette 40, as shown in FIG. 31. When shelf sensors 138 detect that the bag has been placed onto first shelf 16 and that the peel seal 142 has been broken, system 10 prompts the user to place a second bag 140 on the second lowest shelf 16, and so on. System 10 continues to prompt the user to place solutions bags 140 onto shelves 16 and connect the bags to supply lines 38 until all of shelves 16 are filled, as shown in FIG. 32.

Figure 32:
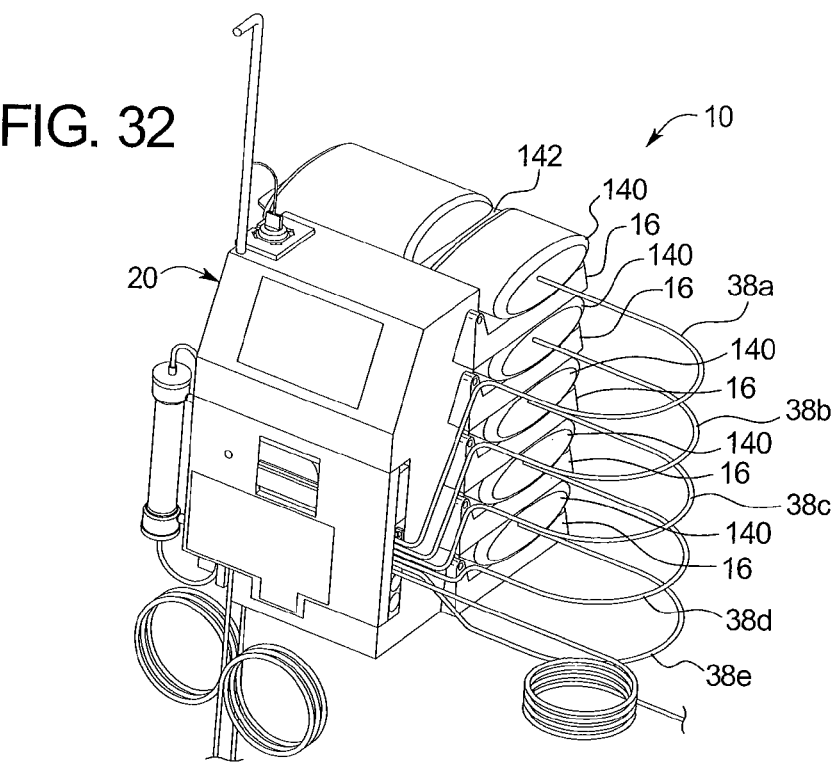
FIG. 32 illustrates one embodiment in which the bag management system can hold up to five solution bags.
Figure 33:
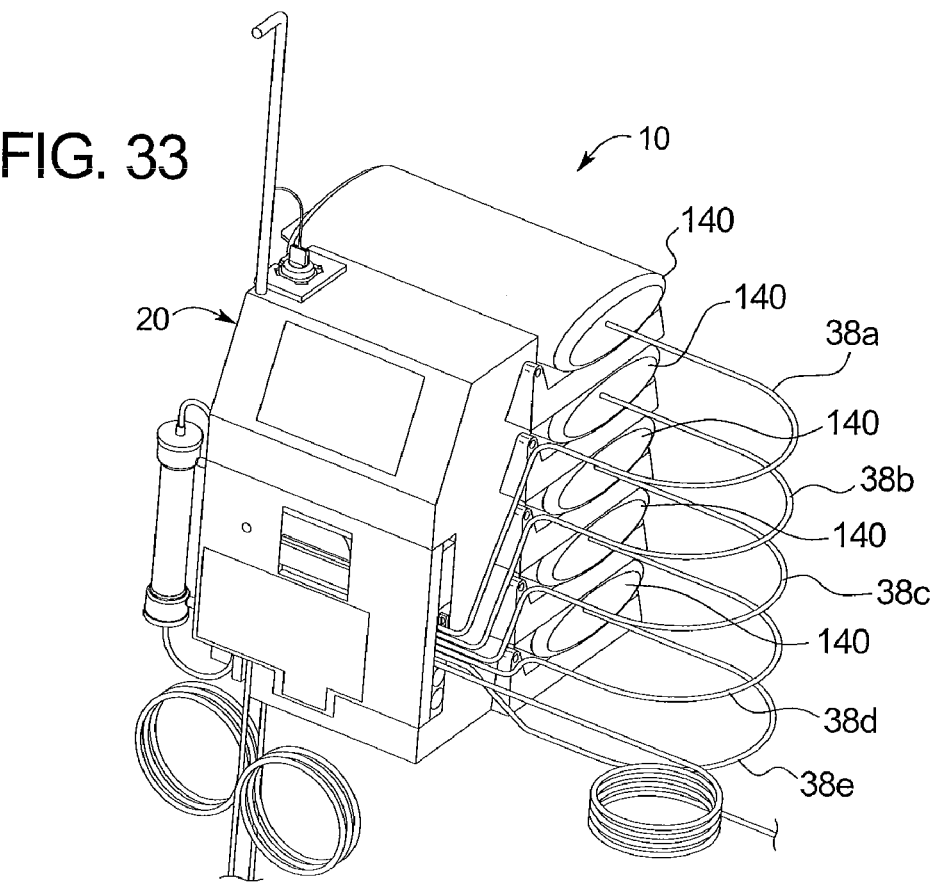
FIG. 33 illustrates the bag management system with all solution bags connected and bag peel seals broken.

As shown in FIG. 32, a peel seal 142 of dual chamber bag 140 present on the top shelf 16 is not broken, a condition which sensors 138 can sense, causing system 10 to instruct the user to break peel seal 142 before continuing with treatment. One such sensor arrangement and peel seal open check is described in U.S. patent application Ser. No. 11/773,742, entitled "Mobile Dialysis System Having Supply Container Detection", filed Jul. 5, 2007, now U.S. Pat. No. 8,105,266, assigned to the assignee of the present disclosure, the pertinent portions of which are incorporated herein expressly by reference. FIG. 33 illustrates all solution bags 140 with peel seals 142 broken, such that treatment can continue.

Figure 34:
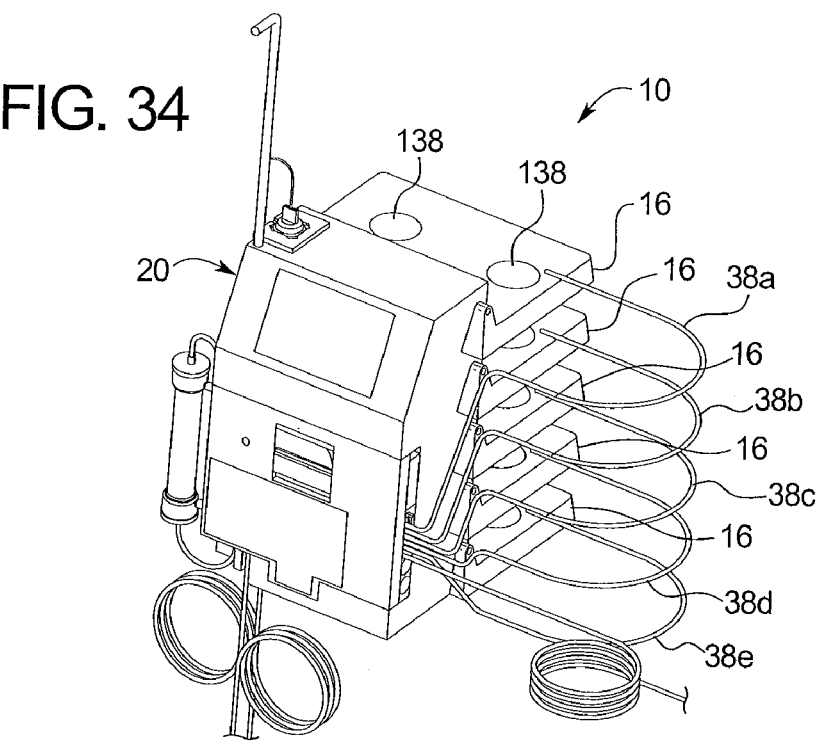
FIG. 34 illustrates the bag management system with capacitive sensors placed on opposite ends of the shelves.

FIG. 34 illustrates one embodiment for the placement of the capacitive sensors 138 that detect the presence of the solution bags, whether peel seal is broken, and perhaps even whether the same solution is present in each bag 140. Other sensors or combinations of sensors can be used alternatively, including optical sensors, inductive sensors, bar code readers, radio frequency identification ("RFID") tags and cameras.

Figure 35:
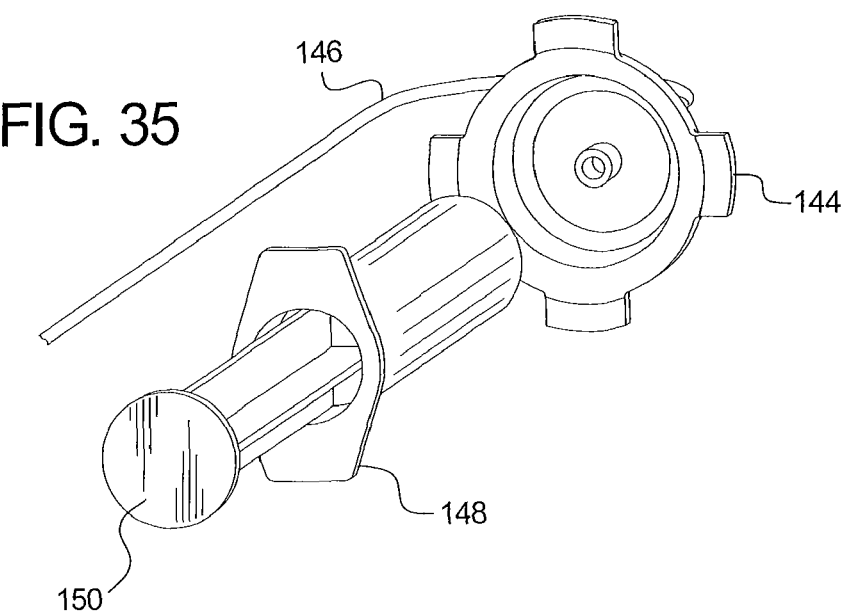
FIG. 35 illustrates one embodiment of a connection of disposable set to a heparin syringe.
Figure 36:
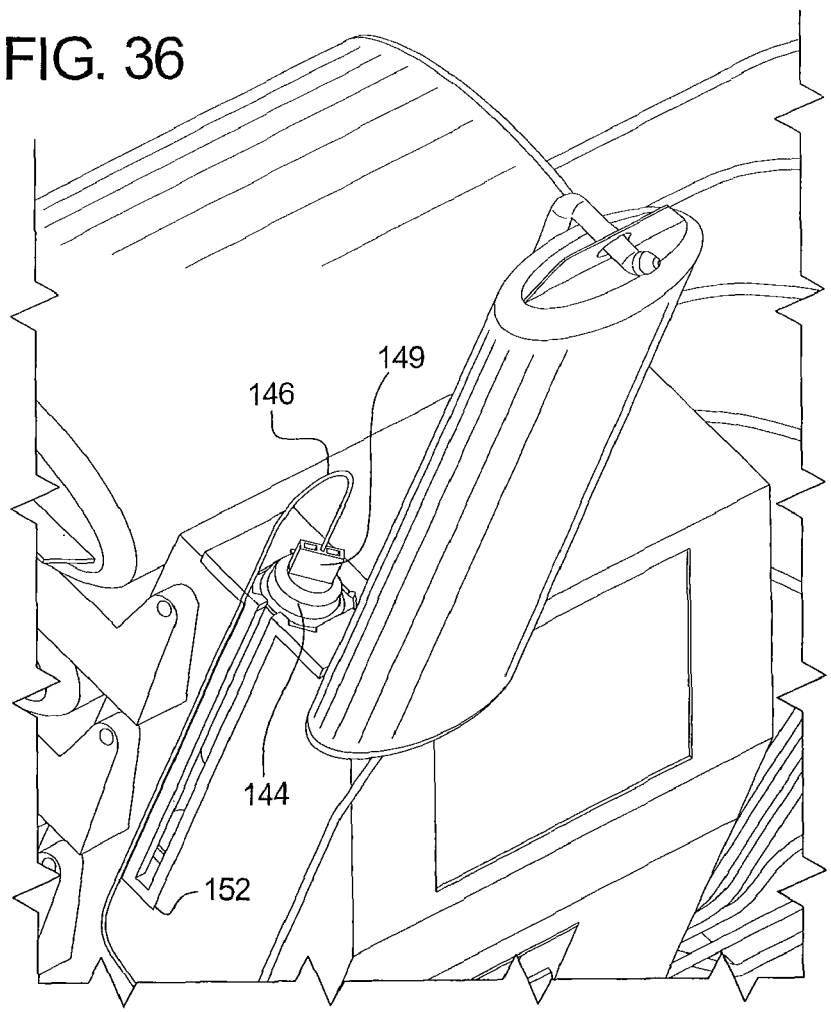
FIG. 36 illustrates the syringe and luer connector assembly loaded into a syringe pump.
Figure 37:
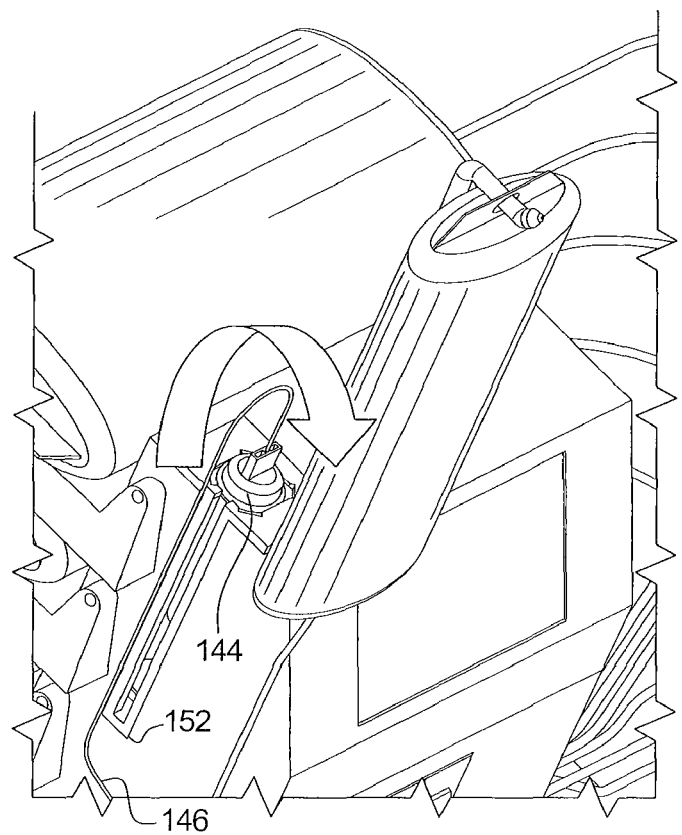
FIG. 37 illustrates the connector of FIG. 36 rotated 45° to lock the syringe into the syringe pump.
Figure 38:
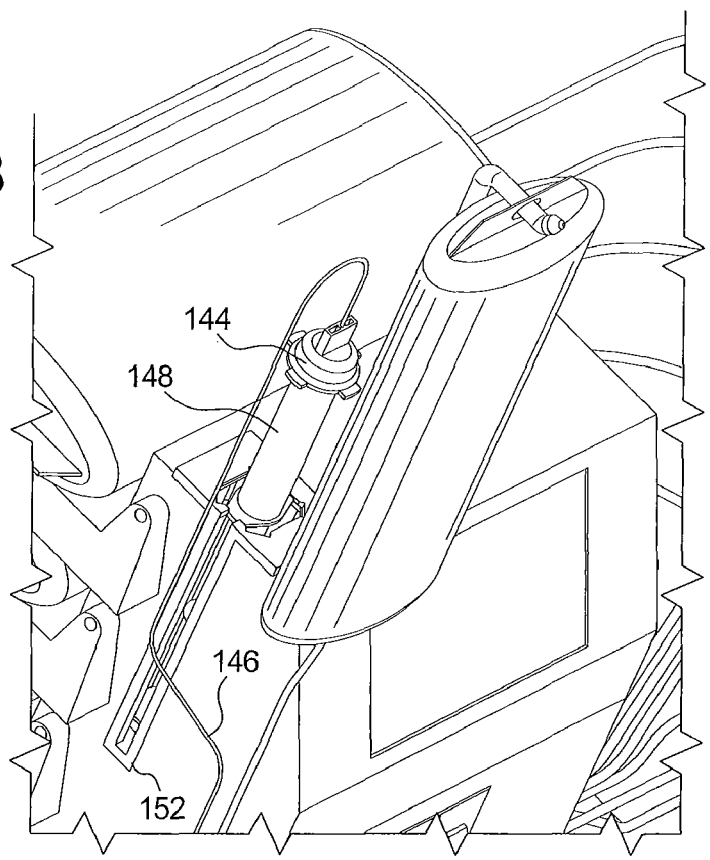
FIG. 38 illustrates that a large, e.g., 50/60 ml, syringe can lock directly into the syringe pump.

FIG. 35 illustrates a luer connection assembly 144, which is located on an end of a heparin line 146, which in turn is connected to disposable cassette 40. A heparin syringe 148 ranging in size from ten milliliters to sixty milliliters, can be connected to luer connection assembly 144 of the disposable set and is inserted with the plunger 150 pointing down into a syringe pump 152 as shown in as shown in FIG. 36. The luer connection assembly 144 is then rotated to lock the syringe in place as shown in FIG. 37. Syringe 148, for sizes larger than 30 milliliters, is inserted with the plunger 150 pointing down into a syringe pump 152 as shown in as shown in FIG. 38. The integral grip 149 on the larger heparin syringes is rotated forty-five degrees to lock the syringe 148 into the syringe pump 152 as shown in FIGS. 37 and 38 versus grip 149 shown in FIG. 36.

Figure 39:
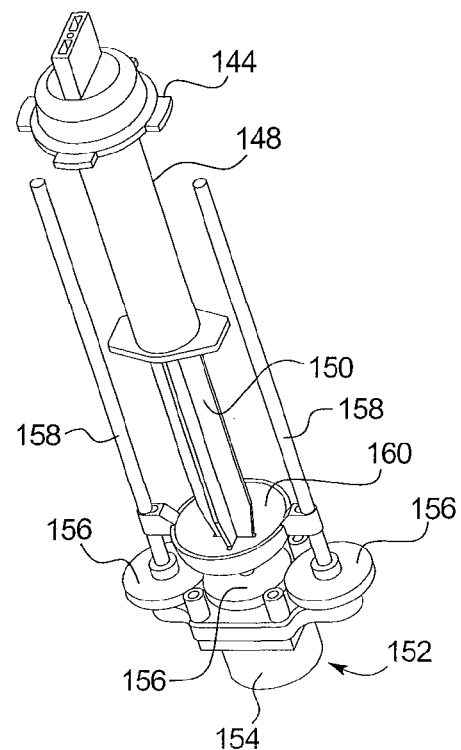
FIG. 39 illustrates one embodiment of a syringe pump mechanism operable with the HHD system of the present disclosure.

Syringe pump 152 is shown in more detail in FIG. 39. Pump 152 includes a stepper motor 154, gears 156, guide rails 158 and a concave push plate 160 that self-centers on the end of the syringe plunger 150. Air exits syringe 148 above the heparin and is purged during the priming of the extracorporeal circuit because syringe 148 is inverted for use. Stepper motor 154 increments 0.9 degrees per step in one implementation. Pump 152 and assembly 144 are sized to accept nearly any size of syringe 148. The user inputs the syringe stroke length and syringe stroke volume into system 10. System 10 can thereafter determine the volume of heparin to be delivered.

Figure 40:
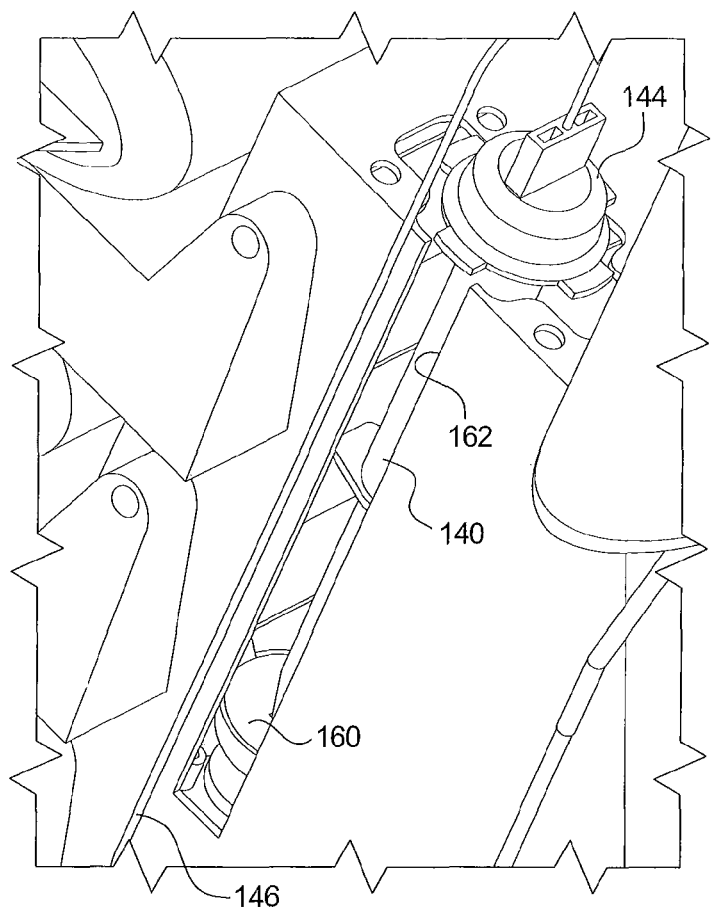
FIG. 40 illustrates one embodiment of a viewing window for viewing heparin delivery.

Smaller syringes 148 are visible through a window 162 in the side of the pump as shown in FIG. 40. Larger syringes housings are visible since they are not inserted into syringe pump 152 and remain outside of instrument 20 as illustrated in FIG. 38. Should a saline or dialysate bag leak, or be spilled, onto instrument 20, the liquid could flow into the heparin pump and out the opening in side window 162 but would not flow inside the instrument, where the fluid could damage instrument 20.

Figure 41:
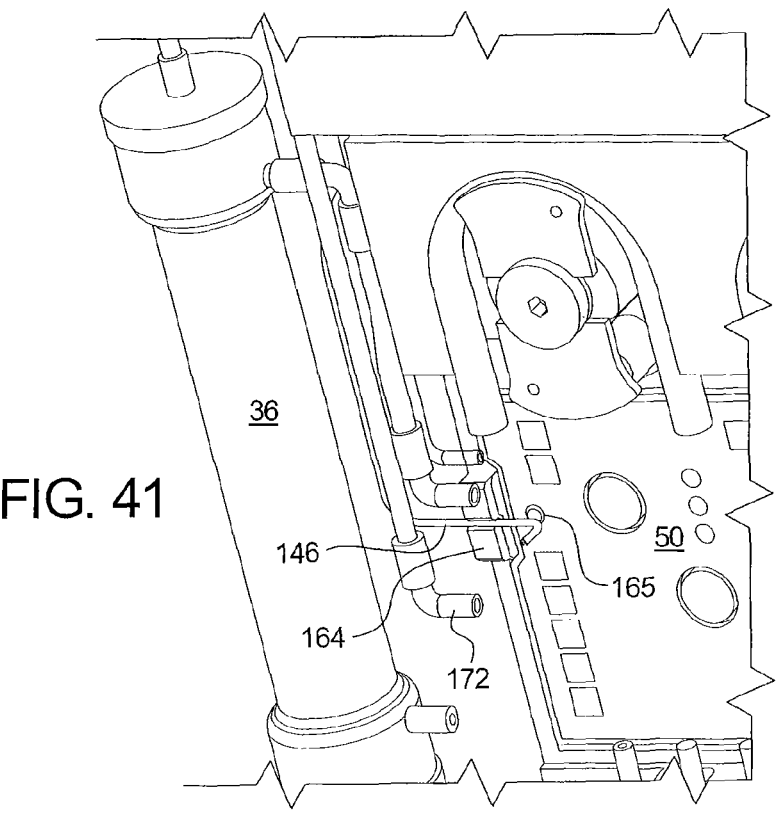
FIG. 41 illustrates the heparin line passing through the side of the cassette and attaching to the backside of the instrument.
Figure 42:
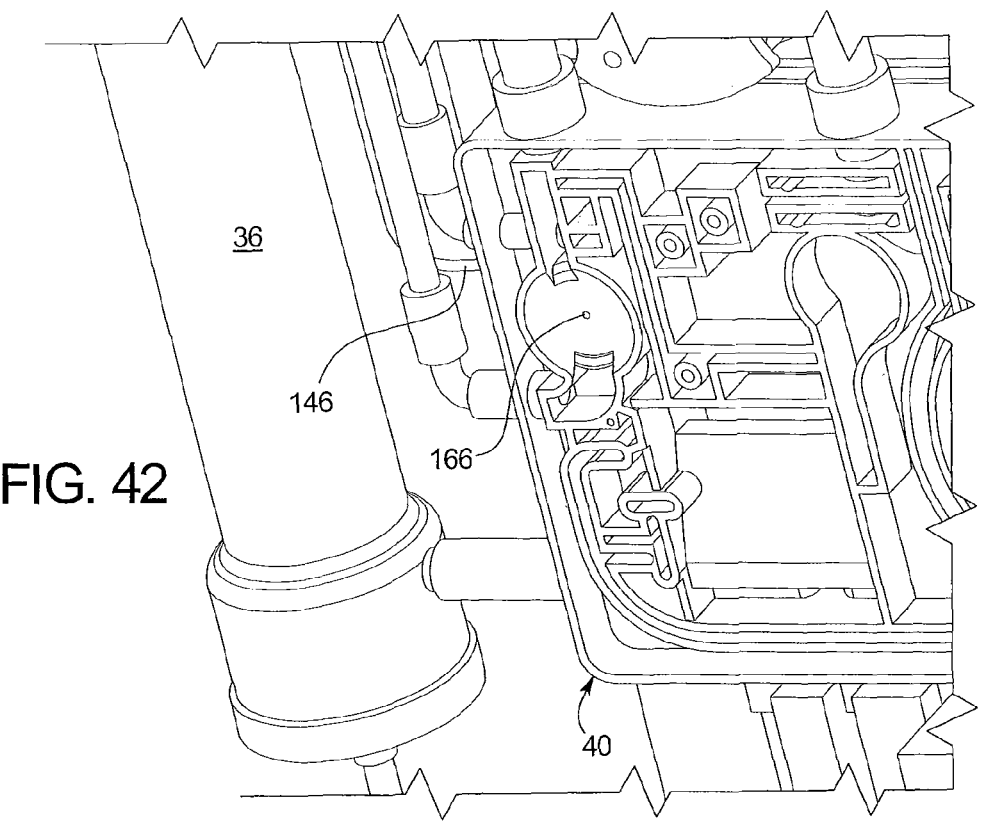
FIG. 42 illustrates that heparin enters at the blood pump outlet just before the dialyzer inlet.

FIGS. 41 and 42 illustrate that heparin line 146 passes through an air bubble detector 164 to cassette 40. System 10 introduces heparin into the patient's blood stream at the outlet 166 of the blood pump just before the blood passes into the dialyzer. The internal volume of the heparin line is essentially that of a very small diameter tube of minimum length. A diaphragm actuated pinch valve 165 (plunger only shown in FIG. 41), which does not add to the internal volume of the heparin line, can be provided to block the flow of heparin to cassette 40.

Figure 43:
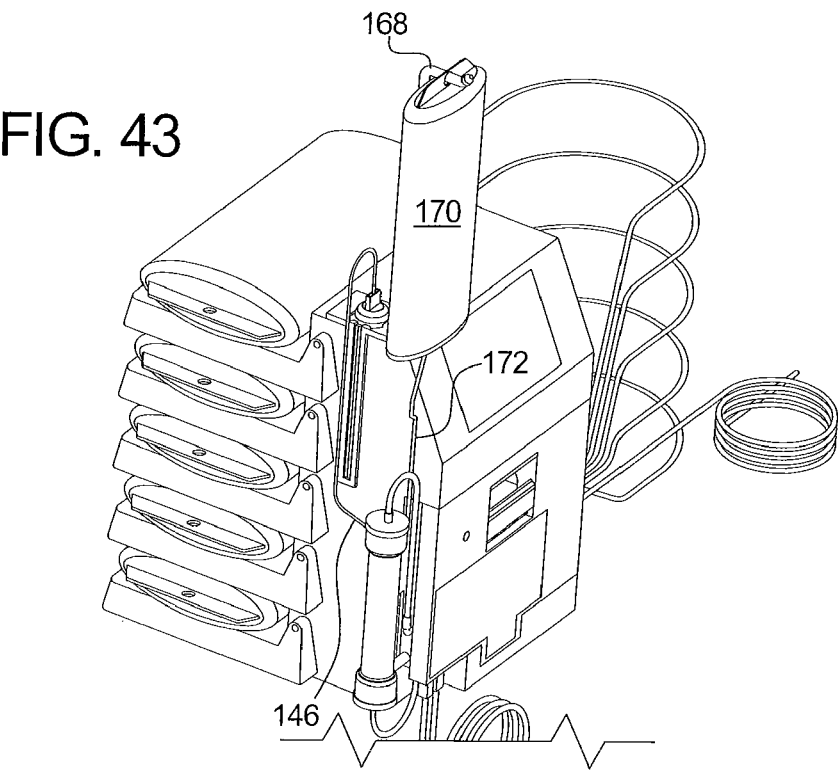
FIG. 43 illustrates one embodiment of a saline bag support rod operable with the HHD system of the present disclosure.

FIG. 43 illustrates a support rod 168 that collapses into instrument 20 when not in use. Support rod 168 supports a saline bag 170 that is used for priming system 10 and rinsing blood back to the patient at the end of the therapy. Alternatively, rod 168 is detachable from instrument 20 when not in use.

Figure 44:
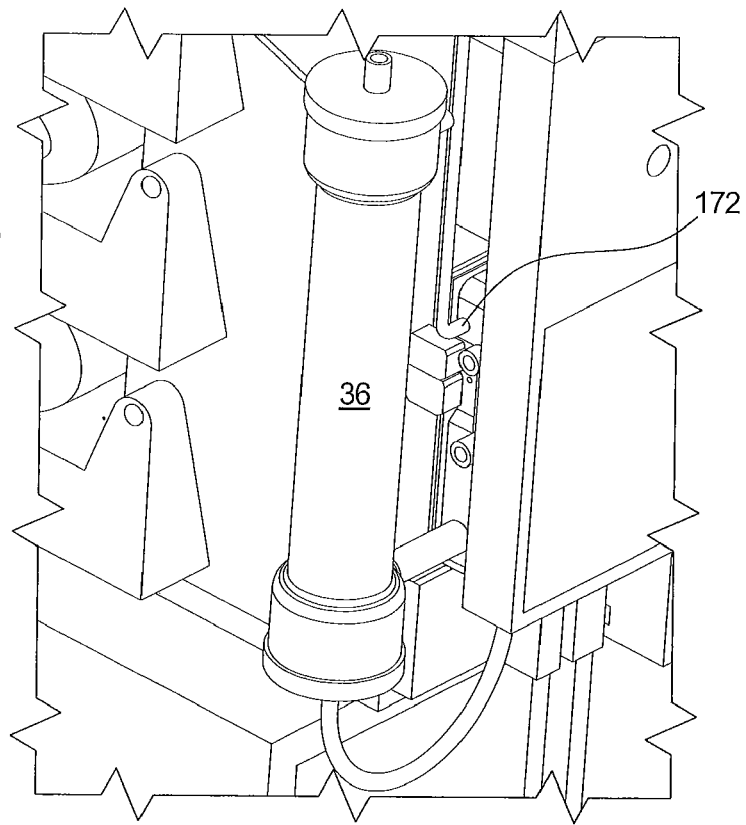
FIG. 44 illustrates the saline line connected to the cassette near the heparin line.
Figure 45:
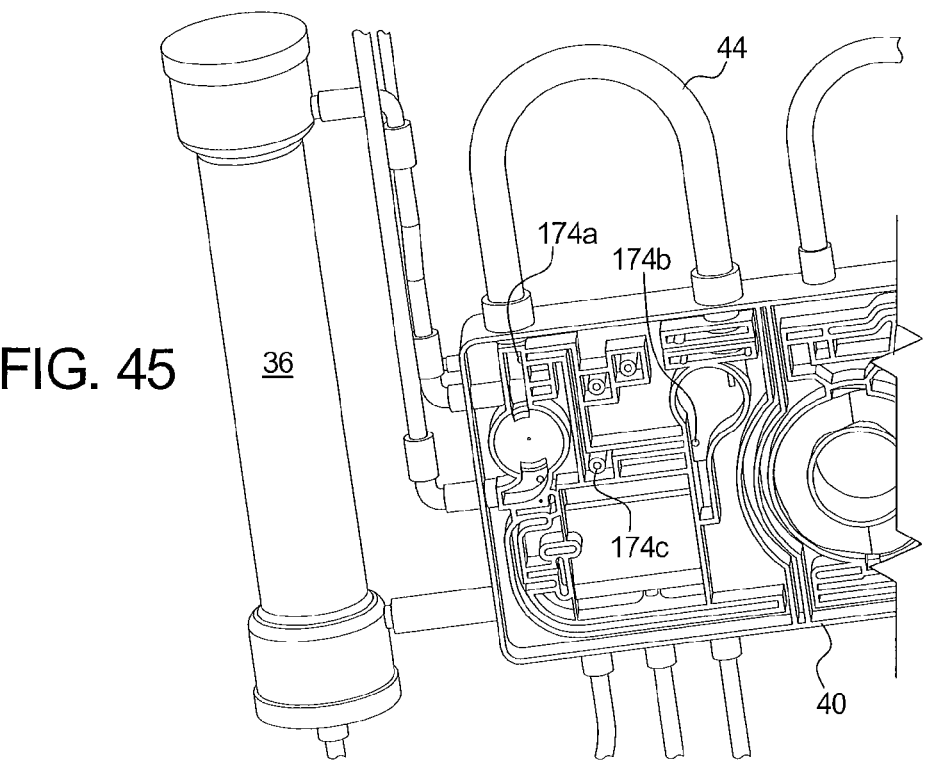
FIG. 45 illustrates a saline valve located on each side of the blood pump.
Figure 46:
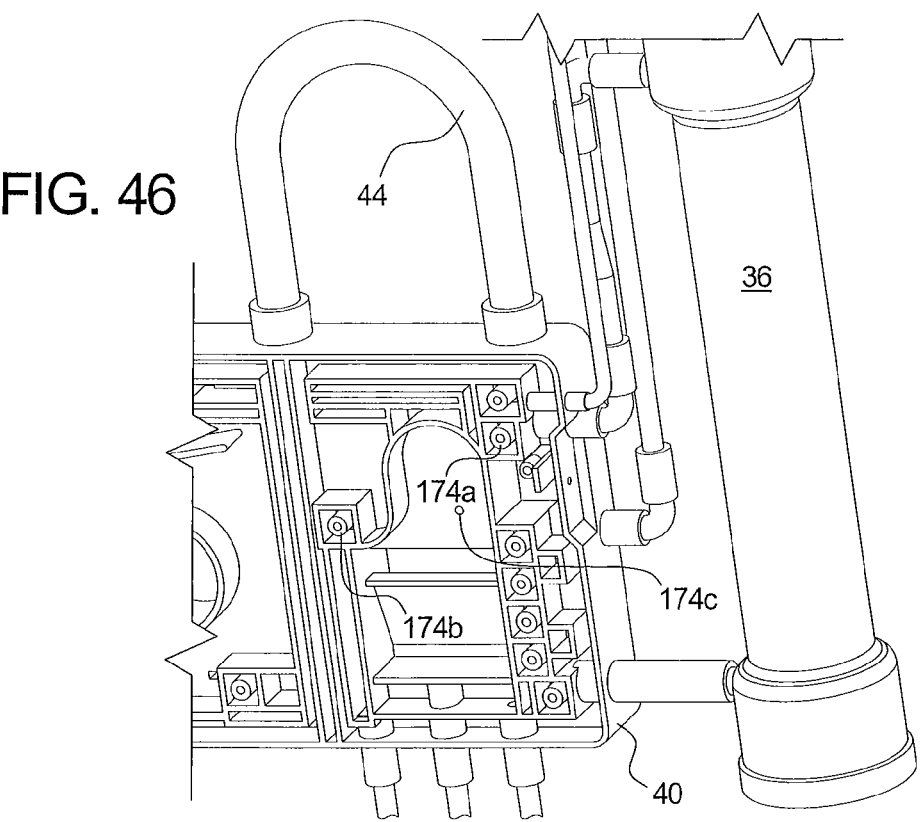
FIG. 46 illustrates that the saline valve ports feed into each side of the blood pump.

FIGS. 43 and 44 illustrate that saline line 172 enters instrument 20 adjacent to the entry of heparin line 164 (see also FIG. 41). FIG. 45 illustrates that two saline flow control valves 174a and 174b are located on each side of blood pump tubing loop 44. The center port from each of the valves feeds directly into blood flow into, or coming from, the blood pump as shown in FIG. 46. The third saline valve 174c is located on the backside of cassette 40 as seen in FIGS. 45 and 46 and is positioned to put saline directly into a venous air separation (drip) chamber 176. The saline valve 174a on the blood pump outlet, and the saline valve 174b leading to dialyzer 36, are opened sequentially to gravity prime the arterial blood line and the venous drip chamber 176 as illustrated later in FIG. 54.

Figure 47:
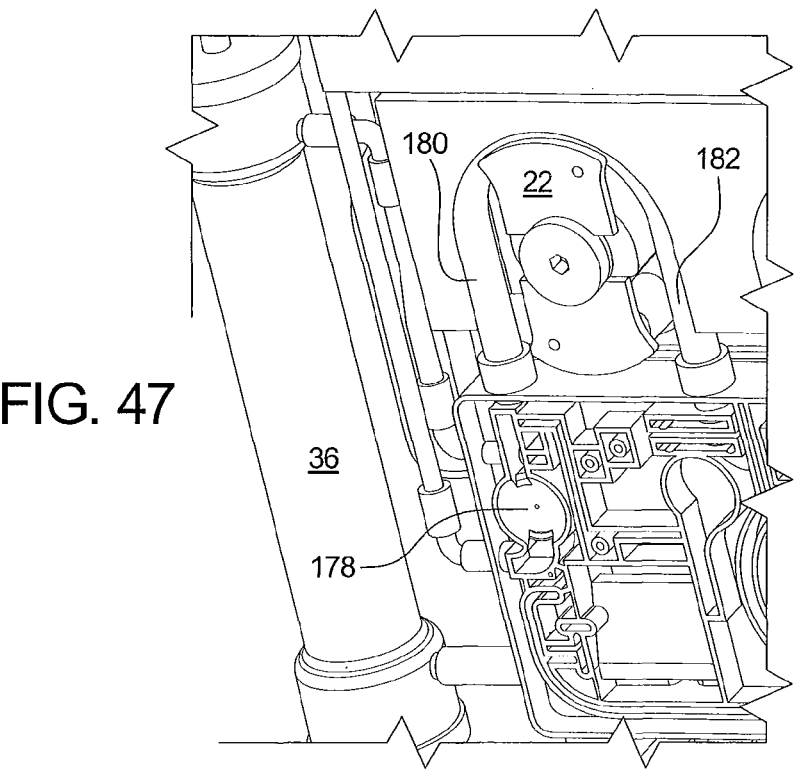
FIG. 47 illustrates that a dialyzer inlet pressure sensor interface can serve additionally as a flow control valve.

As seen in FIG. 47, a normally evacuated dialyzer inlet line pressure transducer interface 178 is pressurized so that it operates as a flow control valve, preventing saline from backflowing into the dialyzer or filter 36. The gravity head from the saline bag causes saline to flow into the blood circuit and into the reversed rotating pump inlet 180 (the outlet under normal operating flow) when saline valve 174a is opened. The reversed flow blood pump head 22 draws saline from the saline bag and pumps it through reversed flow outlet 182 (the inlet under normal operating conditions) and down the arterial line 186.

Figure 48:
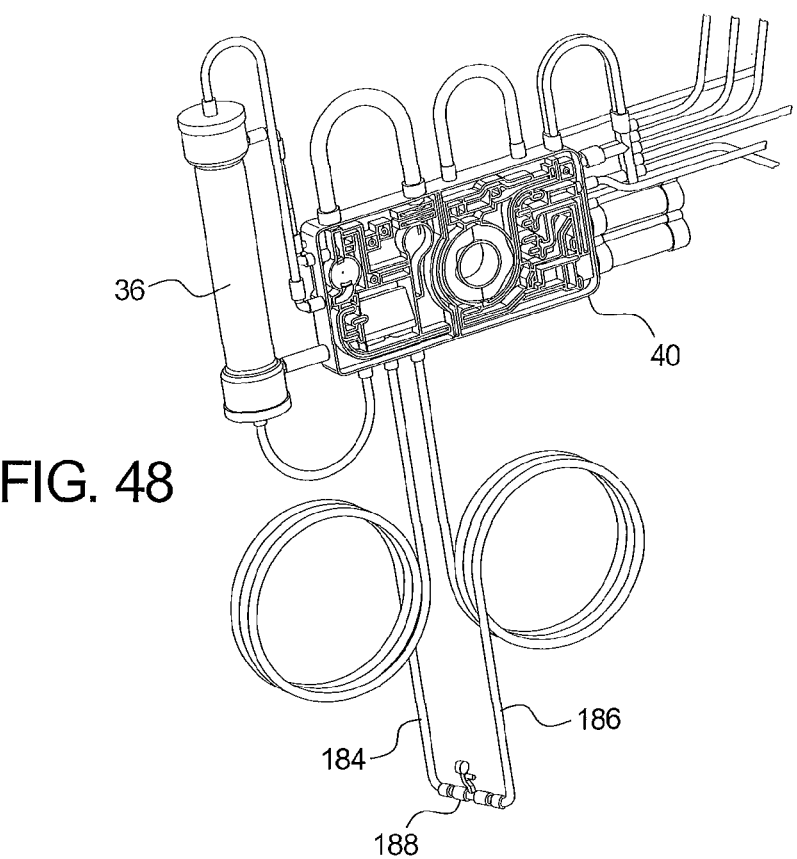
FIG. 48 illustrates the venous and arterial lines are connected together to form a priming loop.
Figure 49:
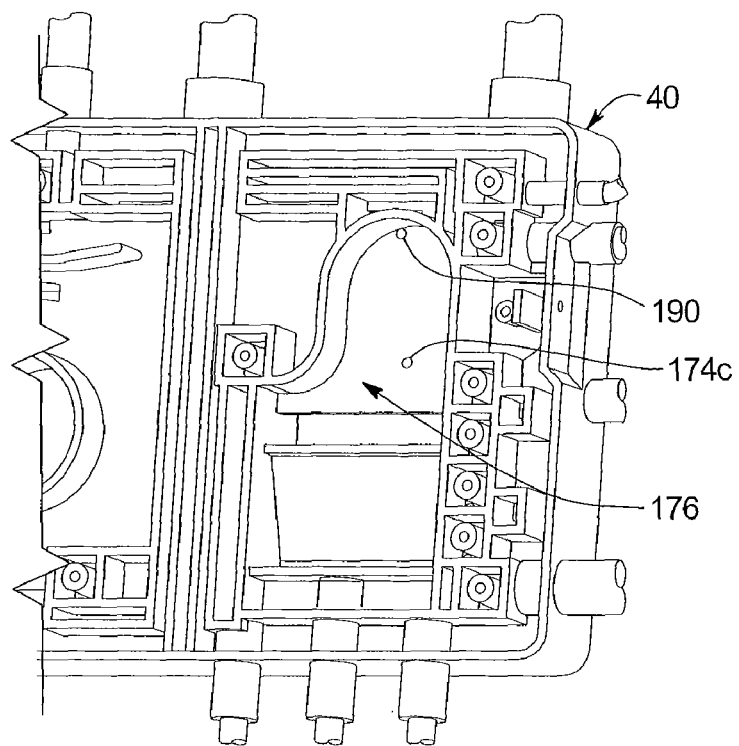
FIG. 49 illustrates one embodiment of a venous air separation chamber operable with the system of the present disclosure.

As seen in FIG. 48, the venous line 184 and arterial line 186 are connected in series during priming so that air is purged from both lines via venous line drip chamber 176 shown in FIG. 49. Standard connections 188 (FIG. 48) can be used to connect the venous line 184 and arterial line 186 in a closed loop. Gravity prevents air from being drawn from the saline bag as long as the bag contains saline. Saline flows slowly into the venous air separation chamber 176 in a "reverse" direction (from normal blood flow) during priming.

Figure 50:
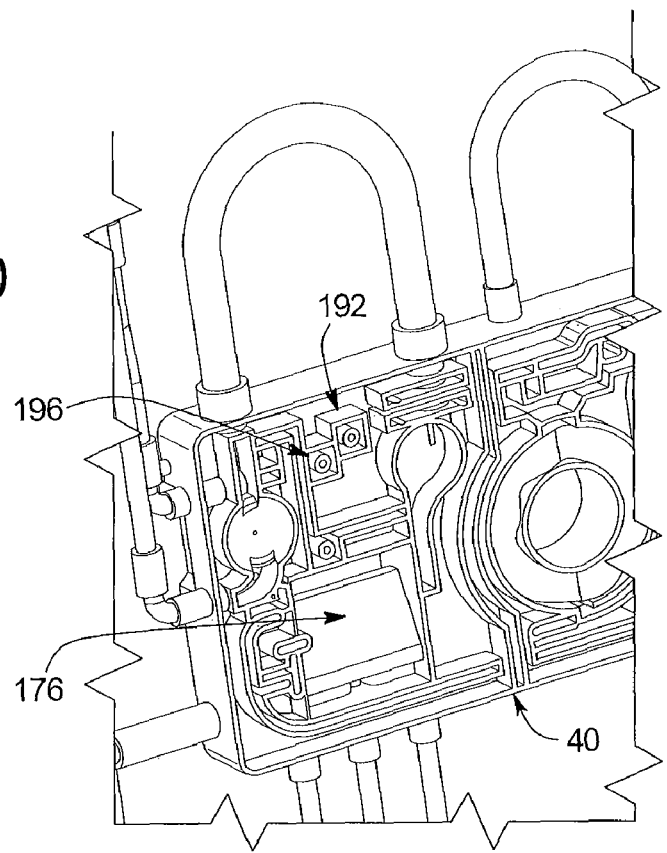
FIGS. 50 and 51 illustrate one embodiment of a venous air separation chamber valve operable with the system of the present disclosure.
Figure 51:
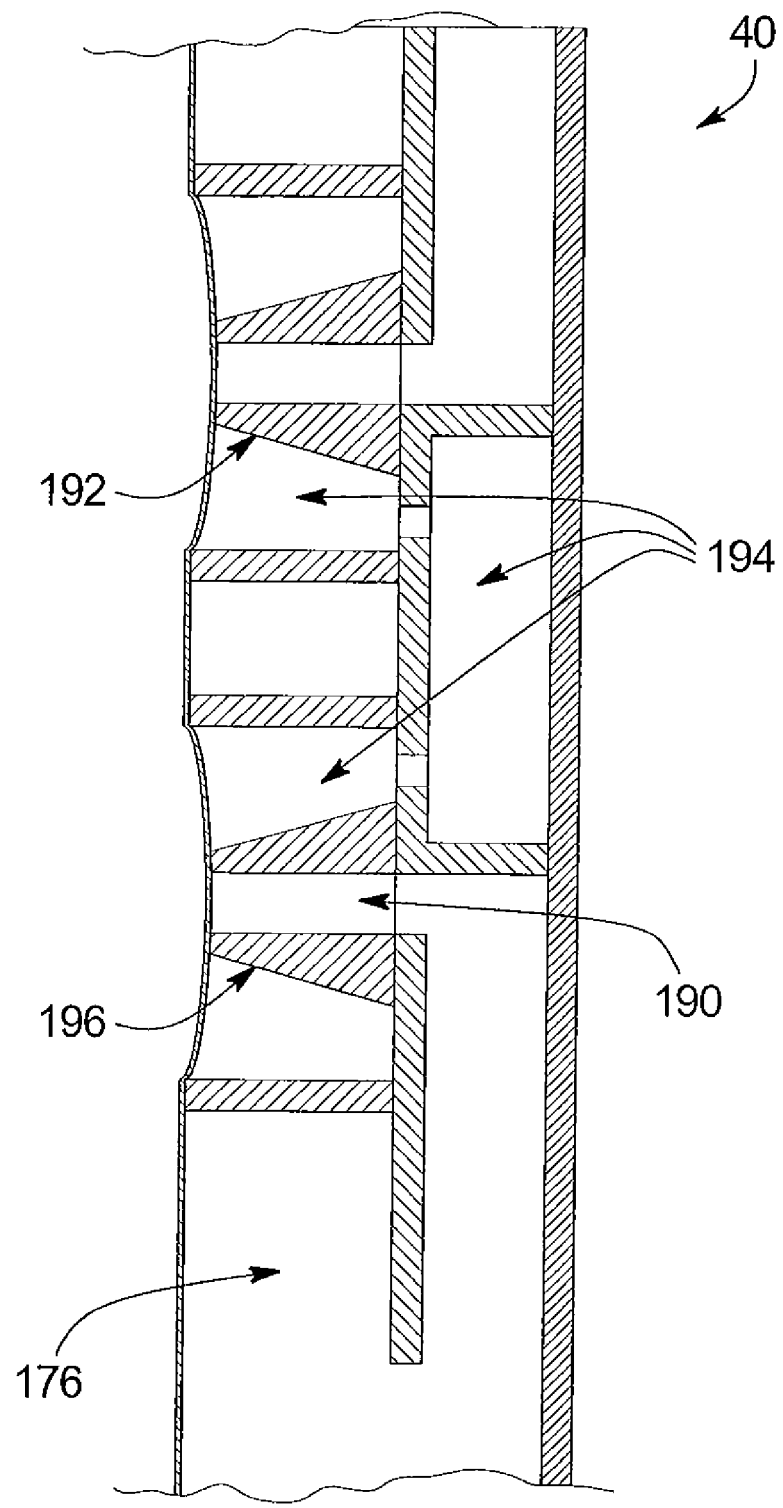

In FIG. 49, the inverted-U shaped venous air separation chamber 176 has a vent port 190 located at its top, so that air can gather there and be vented to the drain. FIG. 50 shows a valve 196 located on the opposite side of the cassette 40 from vent port 190, which is opened whenever air needs to be vented from the chamber. A second vent valve 192 also shown in FIG. 50 can be placed optionally in series with first vent valve 196 and operated sequentially so that predetermined volumetric increments of air can be vented from system 10 to a controlled vent volume 194 shown in FIG. 51. As seen in FIG. 51, port 190 connected to the center of the cassette-based diaphragm valve 196 communicates with air separation chamber 176 so that the "dead" volume needed for these apparatuses is minimized. Valve 196 seals well against the pressure present in the venous air separation chamber. Saline bags can be replaced during a therapy since they can be primed directly into the drip chamber 176 using the third saline valve 174c (FIG. 49).

Figure 52:
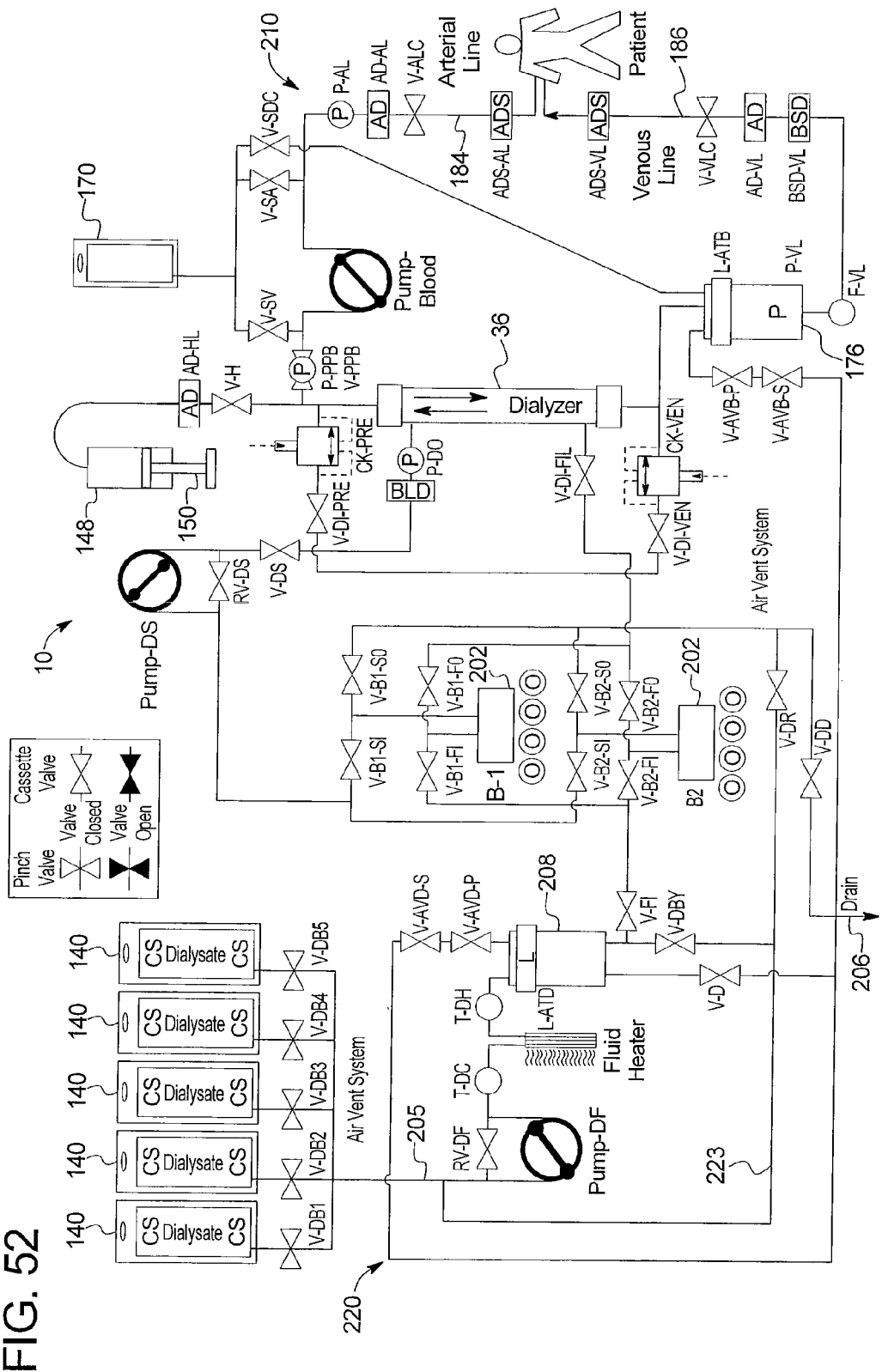
FIG. 52 is a fluid schematic illustrating one possible fluid flow regime for the HHD system of the present disclosure.

FIG. 52 is a schematic of one embodiment of a fluid management system associated with the disposable set. In general, the fluid management system includes a blood circuit 210 and a dialysate circuit 220. System 10 operates the disposable set to provide the hemodialysis therapy. Set 200 of FIGS. 53A and 53B illustrates an embodiment of a disposable set 200 operable with system 10. Disposable set 200 includes cassette 40, filter 36, pump tubes 44, supply tubes 38, balance tubes 202, arterial line 184 and venous line 186, etc., discussed herein.

Figure 54:
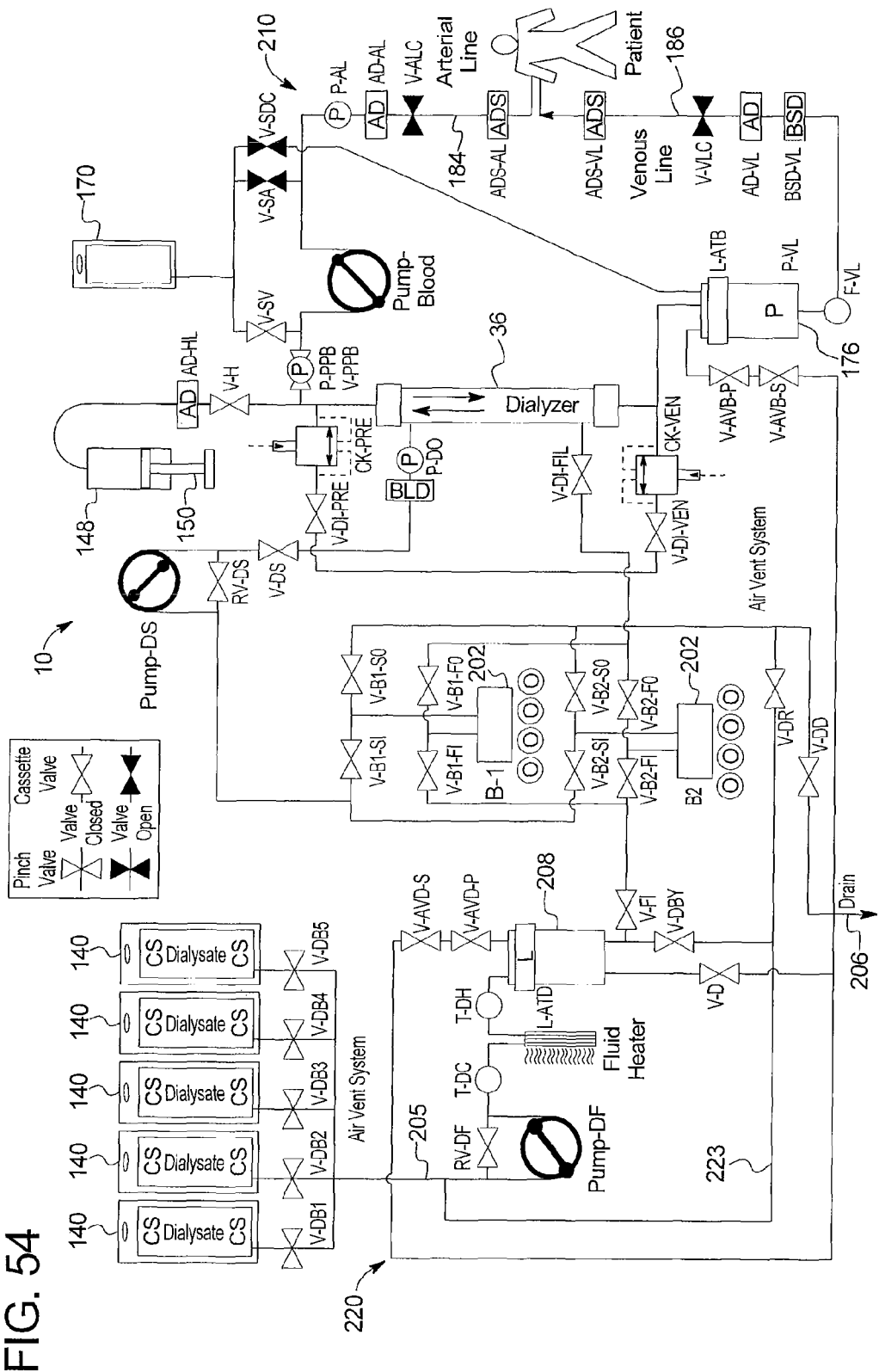
FIG. 54 is a fluid schematic illustrating one embodiment for gravity priming of the venous line, the arterial line and the air trap (drip chamber).

Once disposable set 200 has been loaded into the hemodialysis system 10, dialysate bags 140 have been connected, the saline bag 170 (FIG. 43) has been connected and the heparin syringe 148 has been loaded, system 10 primes itself automatically starting with the blood side circuit. The heparin pump plunger 150 is moved forward until heparin is detected by heparin line air detector AD-HL shown in FIG. 52. Heparin valve V-H is then closed. Next, saline is flowed from the saline bag 170 into the blood side circuit 210 as illustrated in FIG. 54, first through valve V-SA and then through valve V-SDC. A level sensor L-ATB in the AIR TRAP drip chamber detects saline flow into the drip chamber 176 and determines when to close valves V-SA and V-SDC.

Figure 55:
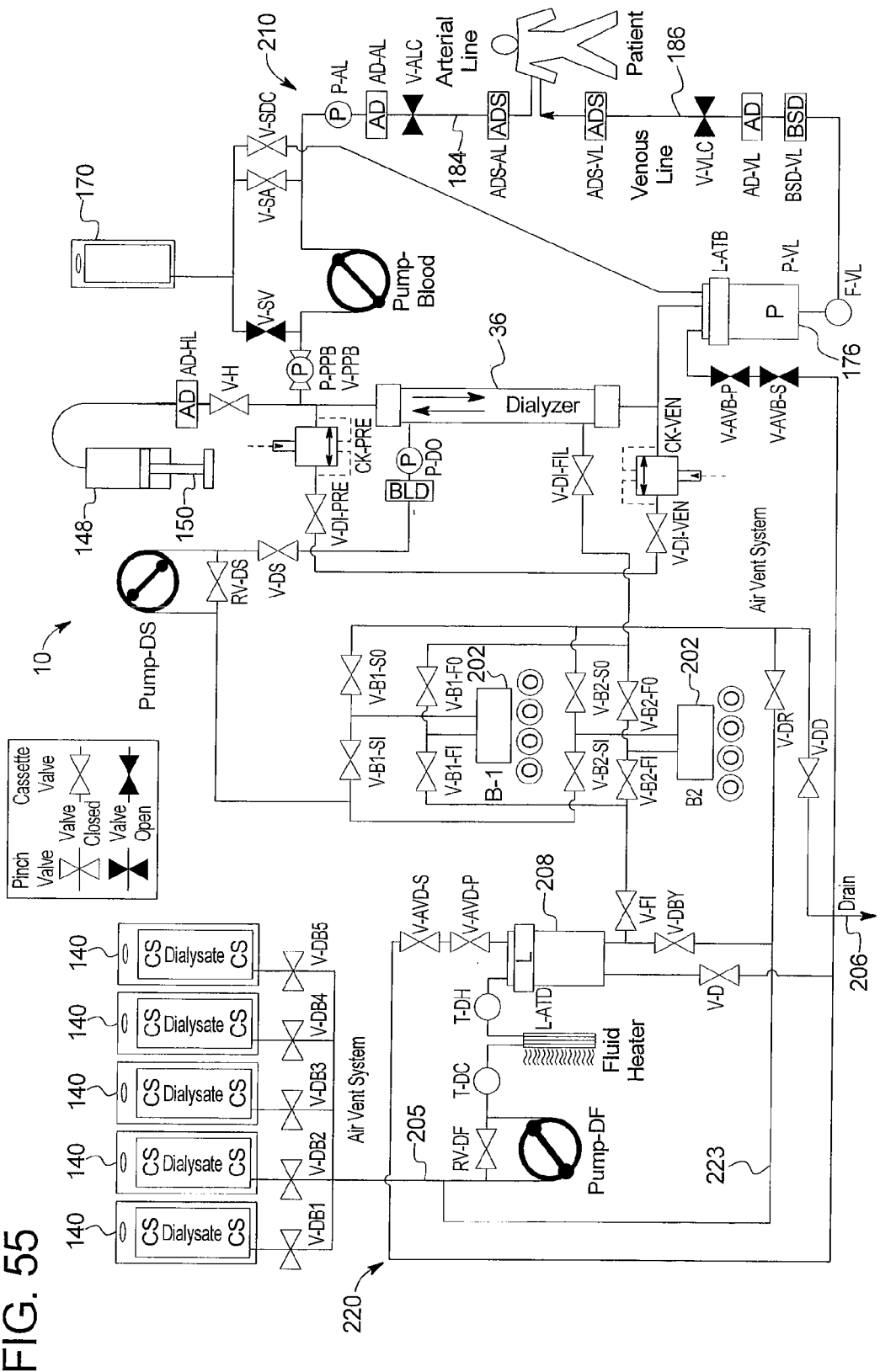
FIG. 55 is a fluid schematic illustrating one embodiment for pressurized priming of the dialyzer and purging of air from blood side circuit.

As shown in FIG. 55, the post pump blood valve V-PPB is then closed, V-SV is opened and PUMP-Blood pumps saline in a reverse flow direction. Pressure sensor P-VL and level sensor L-ATB are used to determine when to open air vent valves V-AVB-P and V-AVB-S. The blood pump pushes the saline backwards down the arterial line and into the venous line. When saline reaches the venous air separator (drip chamber 176), the air will be separated from the fluid and will be discharged into a drain line 206 through vent valves V-AVB-P and V-AVB-S until the air separation chamber 176 is flooded with saline.

Next, as seen in FIG. 55, saline is flowed up into the bottom of dialyzer 36 and up through its hollow fibers. Valve V-PPB is controllably opened so that the air that exits the top of the dialyzer 36 flows into the priming loop, becomes separated in air trap 176 and discharged to drain 206. Saline is also flowed through pours of the fibers of dialyzer 36 to fill the housing of dialyzer 36. System 10 monitors the pressure in the venous line using pressure sensor P-VL to maintain the blood side circuit 210 at a controlled pressure during priming.

Figure 56:
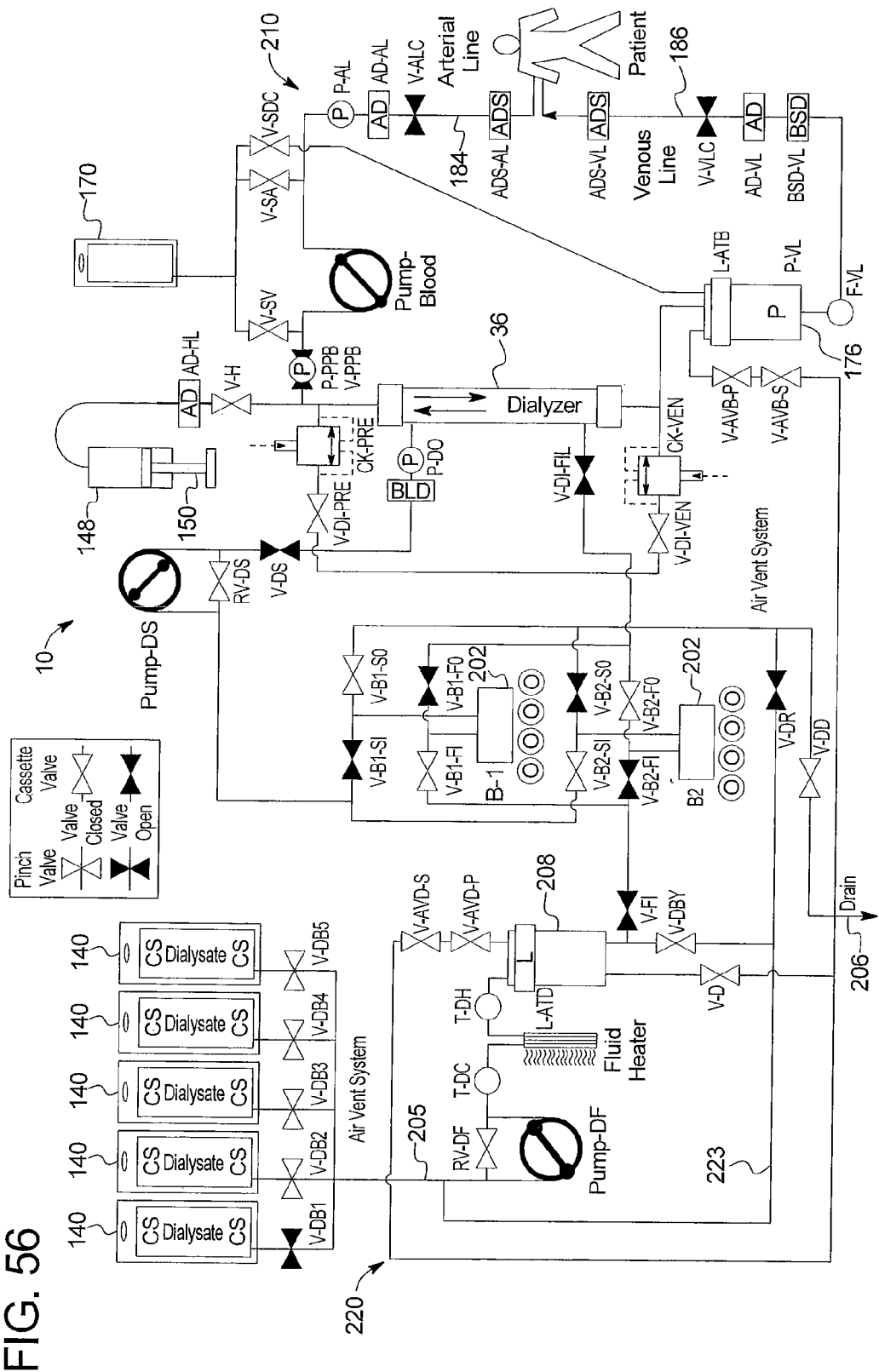
FIGS. 56 and 57 are fluid schematics illustrating one embodiment for priming the dialysate circuit.

As seen in FIG. 56, spent dialysate pump, PUMP-DS and valves V-DS, V-B1-SI, V-B1-SO and V-DD vent air from the dialyzer housing to drain 206. Valves V-DI-VEN, CK-VEN, V-DI-FIL, V-DI-PRE and CK-PRE are opened controllably to allow a predetermined volume of saline to be pushed into the dialysate circuit 220, purging air from associated dialysate lines. A second saline bag 170 can be replaced during a therapy by selecting "replace saline bag", causing the saline line to be primed automatically into the air trap 176.

As shown in FIG. 56, dialysate valve V-DB1 that is associated with the dialysate bag on the top shelf is opened so that dialysate can flow into the inlet of dialysate PUMP-DF. PUMP-DF pushes the dialysate through the inline fluid heater and into a dialysate side air trap 208. Dialysate flows out the bottom of the air trap 208, through valve V-FI and into balance tube B2, through valve V-B2-FI, pushing fluid out the other side of balance tube B2. The fluid exiting the other side of balance tube B2 flows through valve V-B2-SO and into the dialysate recirculating circuit 203 through valve V-DR. The recirculating circuit 223 tees into the supply line circuit 205 at the inlet to PUMP-DF. Pump-DS is operating at the same time drawing air, dialysate and/or saline from the blood side of the dialyzer, though the dialysate side of the dialyzer, into the remainder of the dialysate circuit. PUMP-DS pushes the fluid through valve V-B1-SI and into balance tube B1, pushing fluid out the other side of balance tube B1. The fluid exiting the other side of balance tube B1 flows through valve V-B1-FO and valve V-DI-FIL into the dialysate side of the dialyzer 36.

Figure 57:
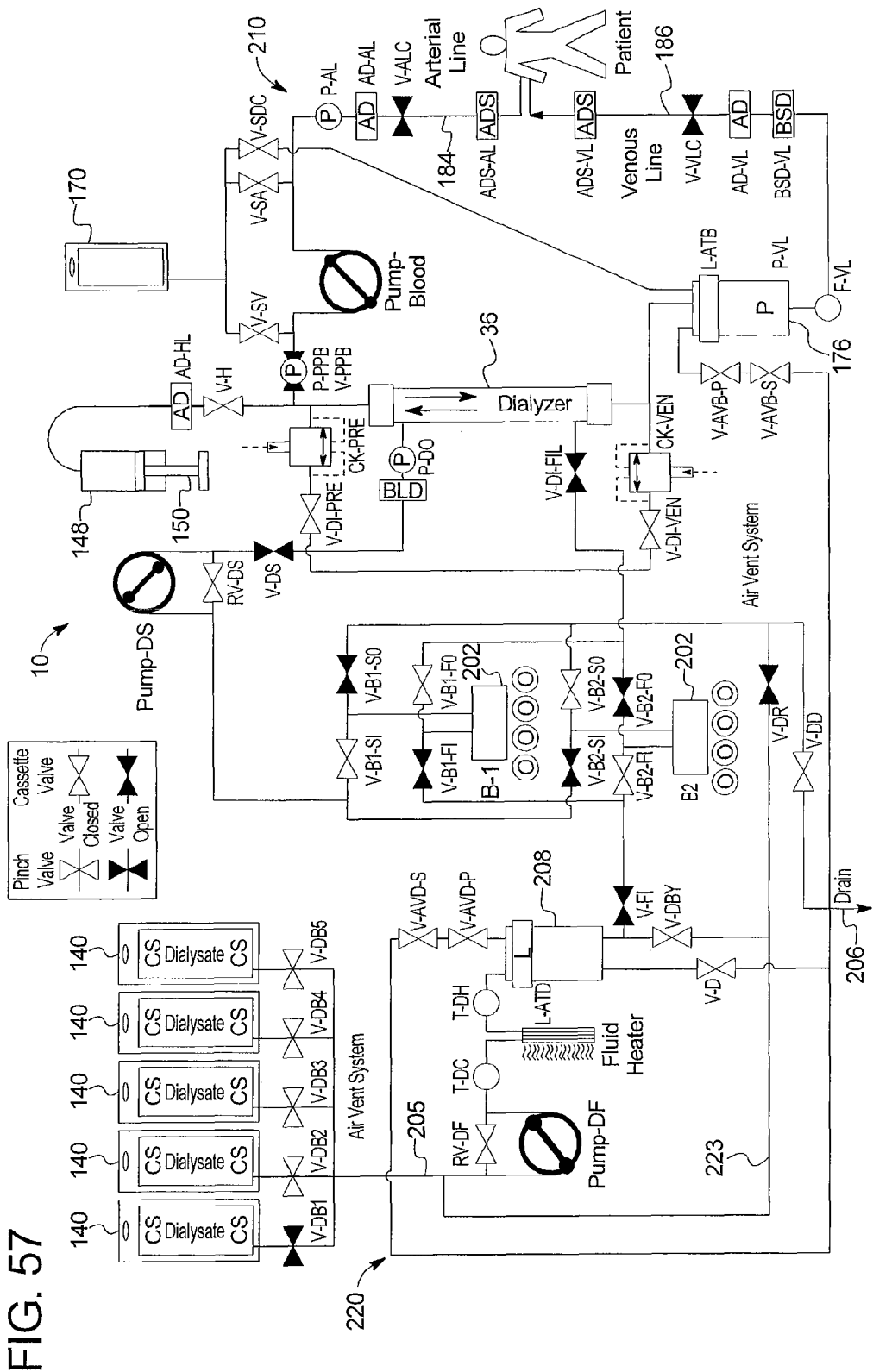

FIG. 57 is similar to FIG. 56 except the roles of balance tubes 202 B1 and B2 are reversed. As fluid enters the dialysate circuit 220, the pressure in the circuit increases, forcing air to be discharged under pressure to drain line 206 through open vent valves V-AVD-P and V-AVD-S.

Figure 58:
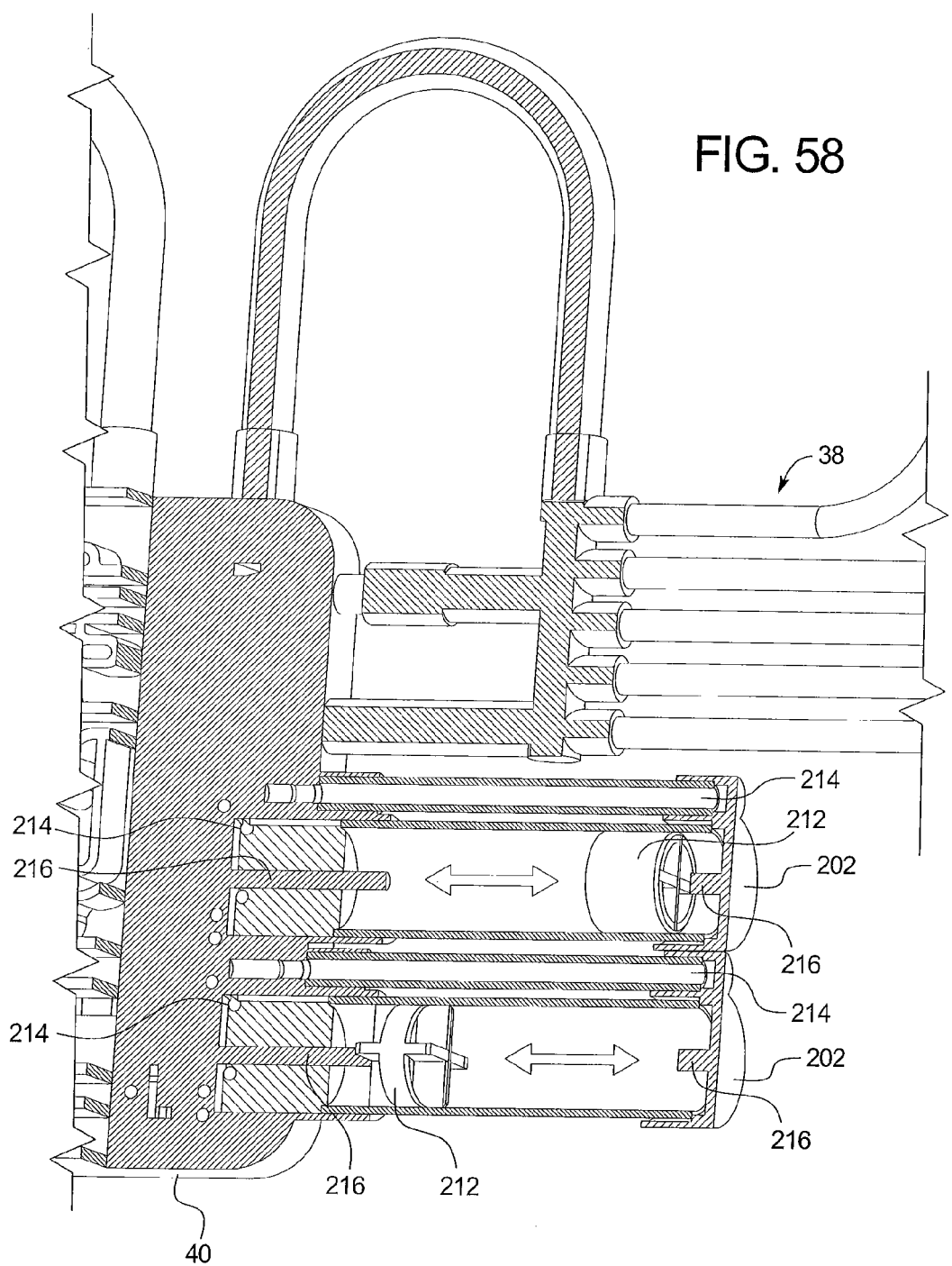
FIG. 58 is a section view of one embodiment for balance tubes having outlets at the tops of the tubes, the tubes operable with the HHD system of the present disclosure.

FIG. 58 illustrates balance tubes 202. Instrument 20 includes pairs of optical sensors (not shown) operable with balance tubes 202 to determine an end of travel of a separator 212 located within each balance tube 202. The optical sensors in one embodiment are reflective, so that an emitter and receiver of each sensor can be on the same (e.g., non-door) side of balance tube 202. The sensors alternatively include emitters and receivers located on opposite sides of balance tubes 202. Outlets 214 on both ends of both balance tubes 202 are at the balance tube tops when mounted for operation as shown if FIG. 58, so that air will pass through the balance tubes and not become trapped in the tubes as long as system 10 is level. Mechanical stops 216 limit the movement of separators 212 to that visible to the optical sensors.

Figure 59:
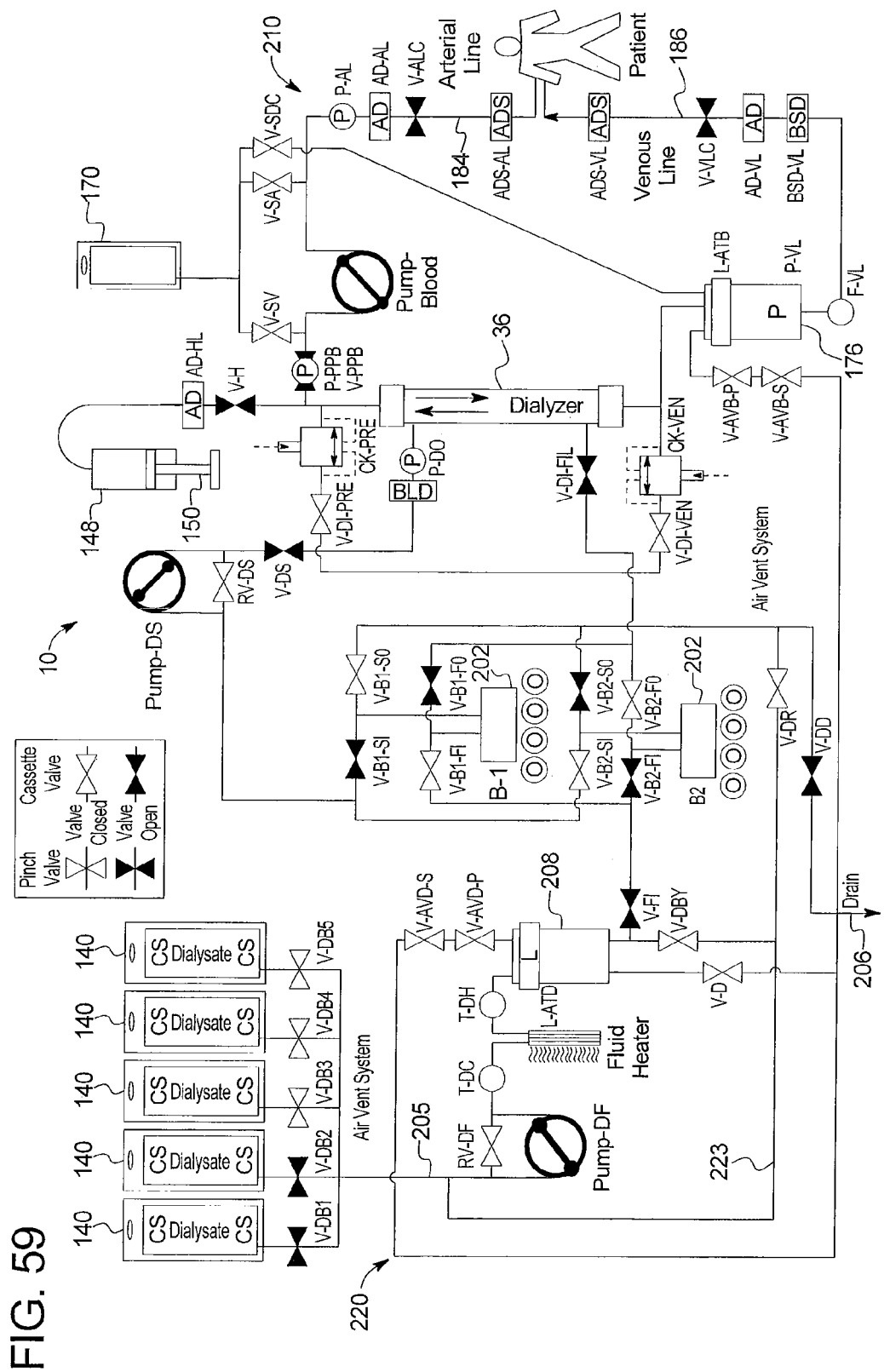
FIG. 59 is a fluid schematic illustrating the HHD system of the present disclosure performing hemodialysis.

FIG. 59 illustrates HHD system 10 performing hemodialysis. Here, fresh dialysate is pushed from balance tubes 202 to dialyzer 36 via valve V-DI-FIL, while spent dialysate is removed from dialyzer 36 via valve V-DS to balance tubes 202.

Figure 60:
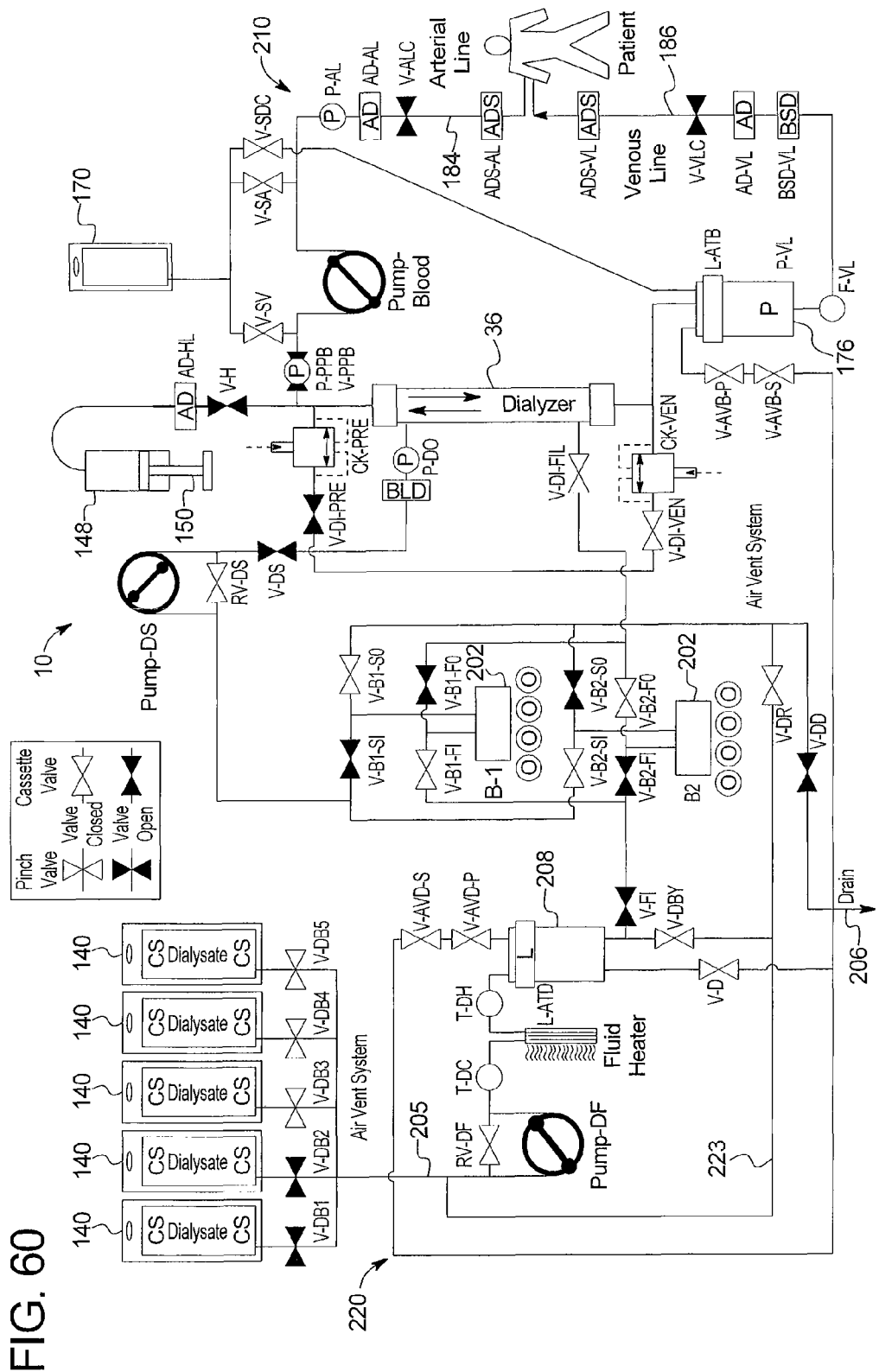
FIG. 60 is a fluid schematic illustrating the HHD system of the present disclosure performing pre-dilution hemofiltration.

FIG. 60 illustrates HHD system 10 performing pre-dilution hemofiltration. Here, fresh dialysate is pushed from balance tubes 202 to blood circuit 210 directly via valve V-DI-PRE, while spent dialysate is removed from dialyzer 36 via valve V-DS to balance tubes 202.

Figure 61:
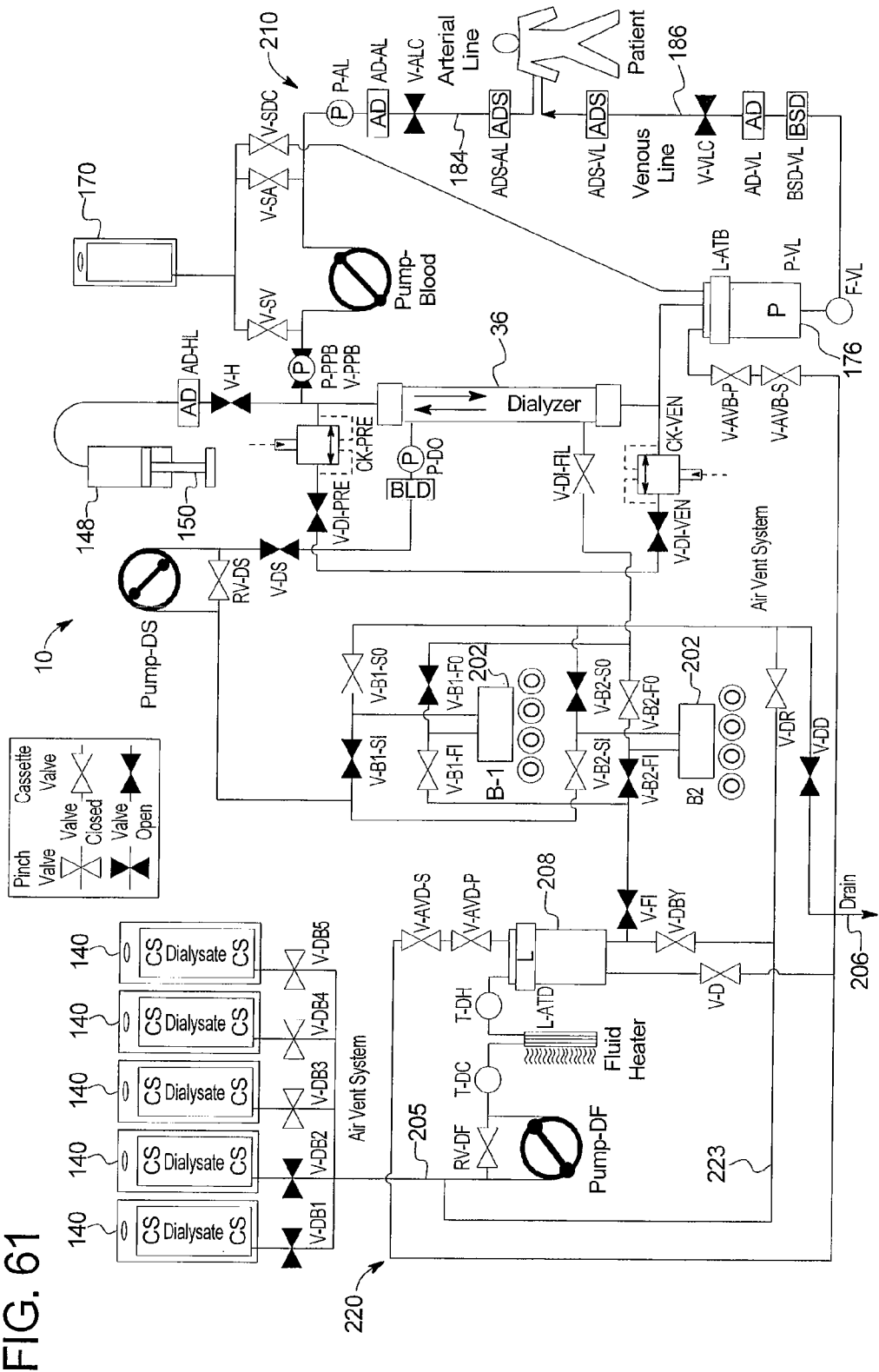
FIG. 61 is a fluid schematic illustrating the HHD system of the present disclosure performing post-dilution hemofiltration.

FIG. 61 illustrates HHD system 10 performing post-dilution hemofiltration. Here, fresh dialysate is pushed from balance tubes 202 to blood circuit 210 directly via valve V-DI-VEN, while spent dialysate is removed from dialyzer 36 via valve V-DS to balance tubes 202.

Figure 62:
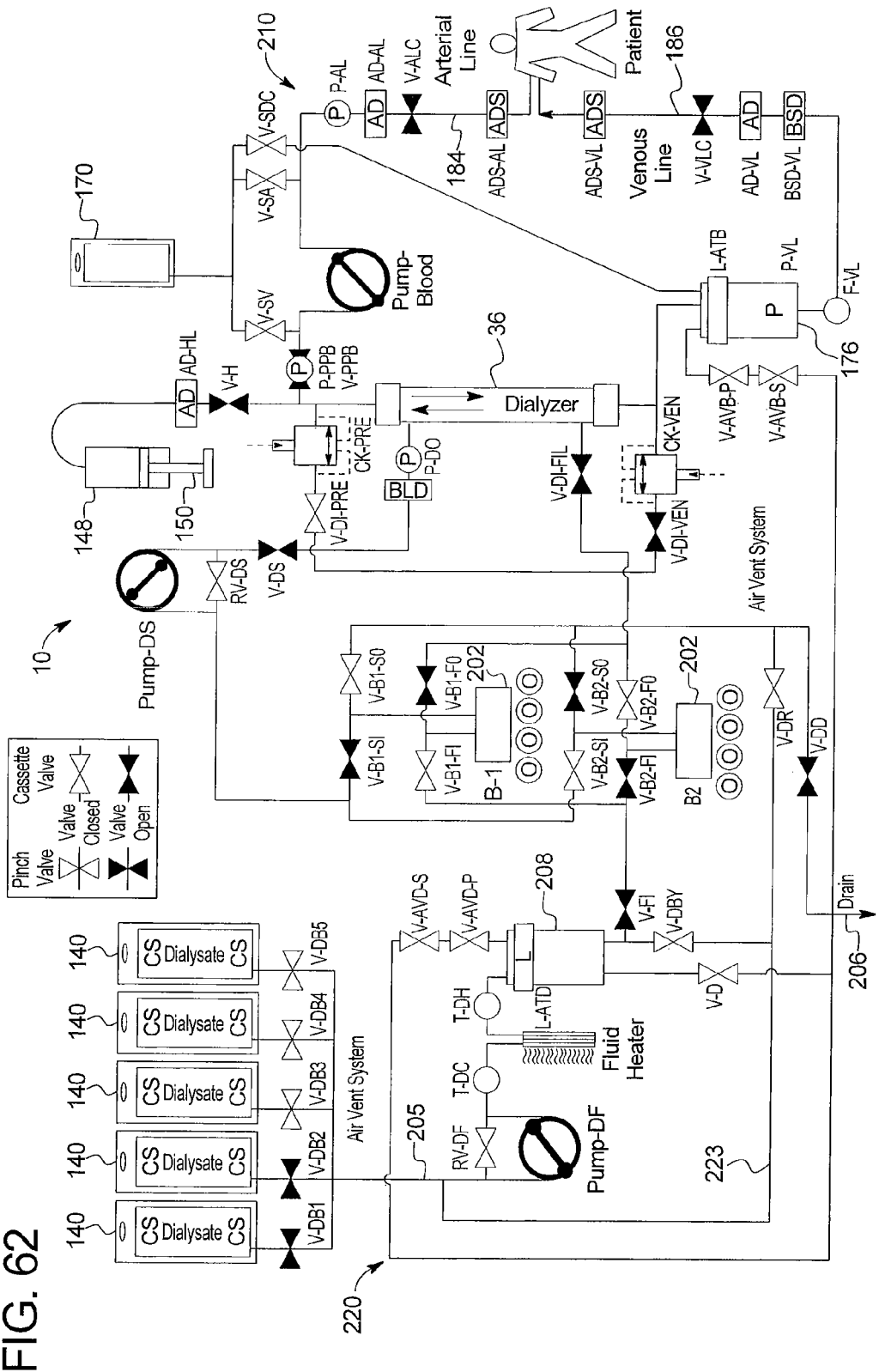
FIG. 62 is a fluid schematic illustrating the HHD system of the present disclosure performing post-dilution hemodiafiltration.

FIG. 62 illustrates HHD system 10 performing post-dilution hemo-diafiltration. Here, fresh dialysate is pushed from balance tubes 202 to (i) dialyzer 36 via valve V-DI-FIL and (ii) blood circuit 210 directly via valve V-DI-VEN, while spent dialysate is removed from dialyzer 36 via valve V-DS to balance tubes 202.

Figure 63:
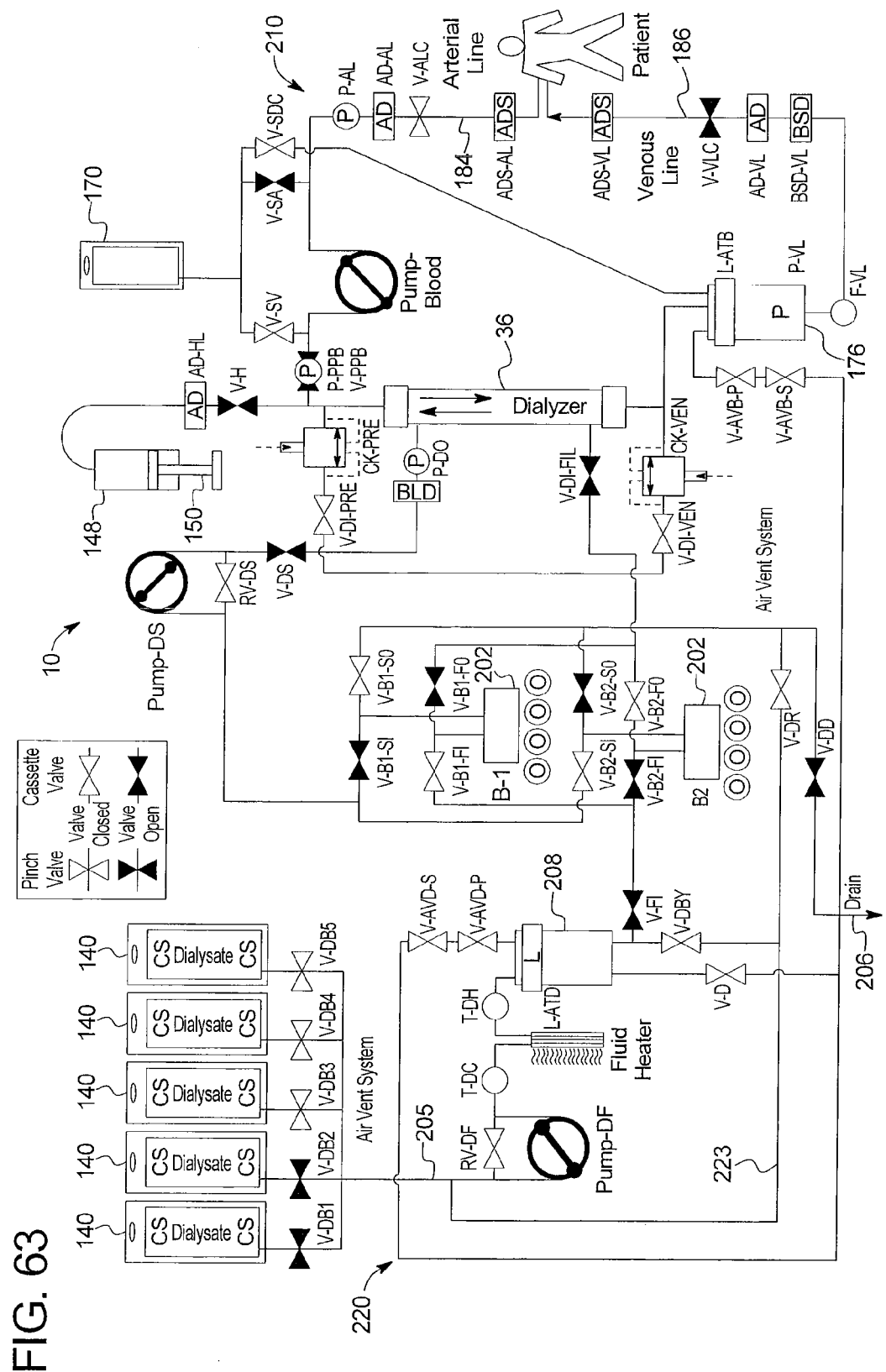
FIG. 63 is a fluid schematic illustrating one embodiment for closing an arterial line clamp, opening a saline valve and infusing saline bolus during therapy.

FIG. 63 illustrates one embodiment for closing arterial line clamp V-ALC, opening a saline valve V-SA and infusing a saline bolus into blood circuit 210 during therapy.

Figure 64:
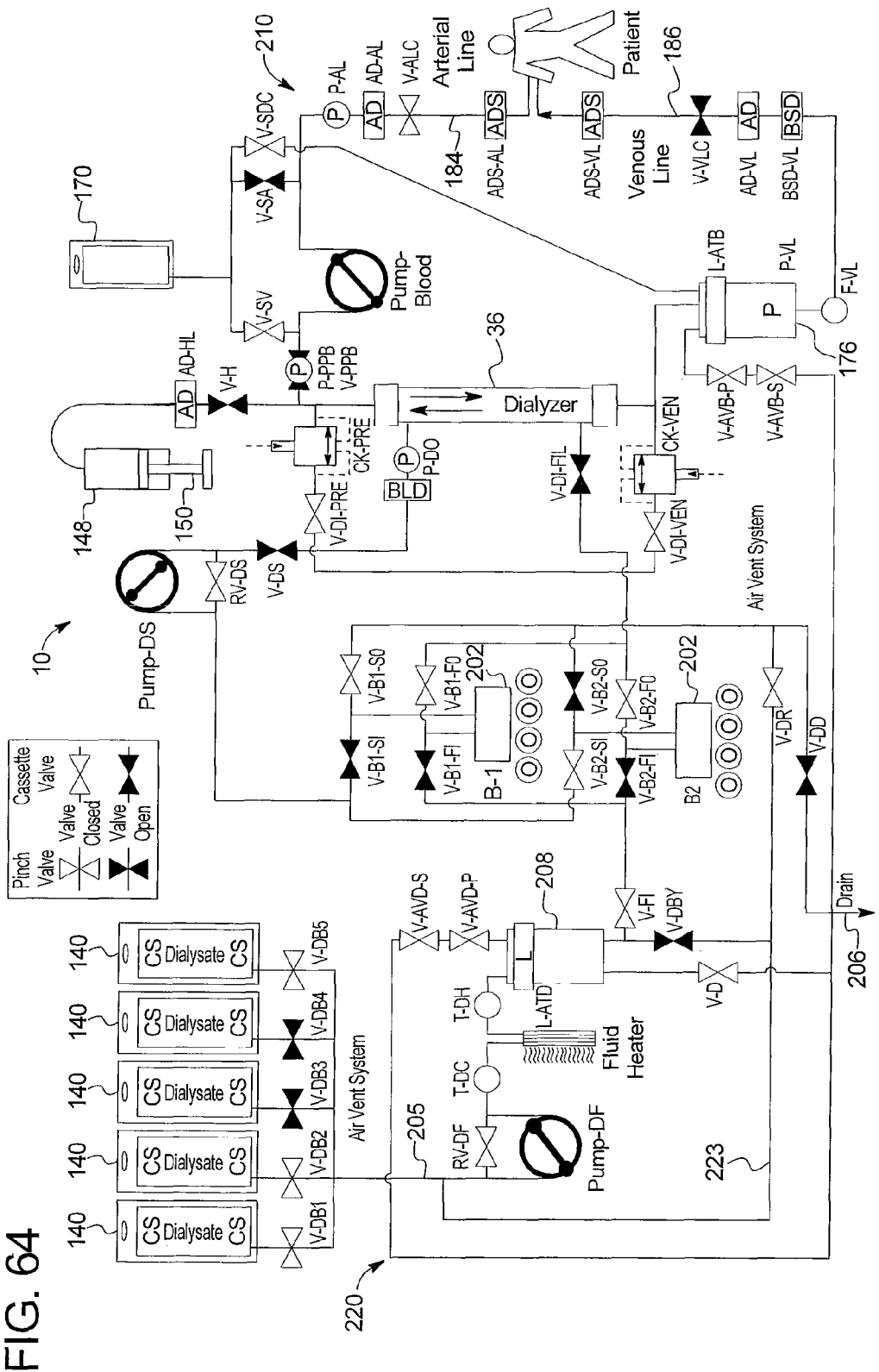
FIG. 64 is a fluid schematic illustrating one embodiment for recirculating fresh dialysate in heater circuit and balance tubes to remove ultrafiltration ("UF").

FIG. 64 illustrates one embodiment for recirculating fresh dialysate through Fluid Heater and recirculating circuit 223 and balance tubes B1 and B2 to remove UF. In FIG. 64, pump-DF pumps fluid in a loop that includes Fluid Heater since valve V-DBY is open. Valve V-FI is closed so no fresh dialysate is delivered to balance chambers 202. Pump-DS pulls spent fluid from the dialyzer 36 through valve V-DS and pushes the spent fluid through valve V-B1-SI and into the right side of balance tube B1. Fresh fluid then flows from the left side of balance tube B1 through valves V-B1-FI and V-B2-FI and into the left side of balance tube B2. Spent fluid then flows out the right side of balance tube B2 through valves V-B2-SO and V-DD and into the drain line. In this manner, a volume of spent fluid is sent to drain 206 without a corresponding volume of fresh fluid delivered from supply bags 140 to either balance chamber B1 or B2.

Figure 65:
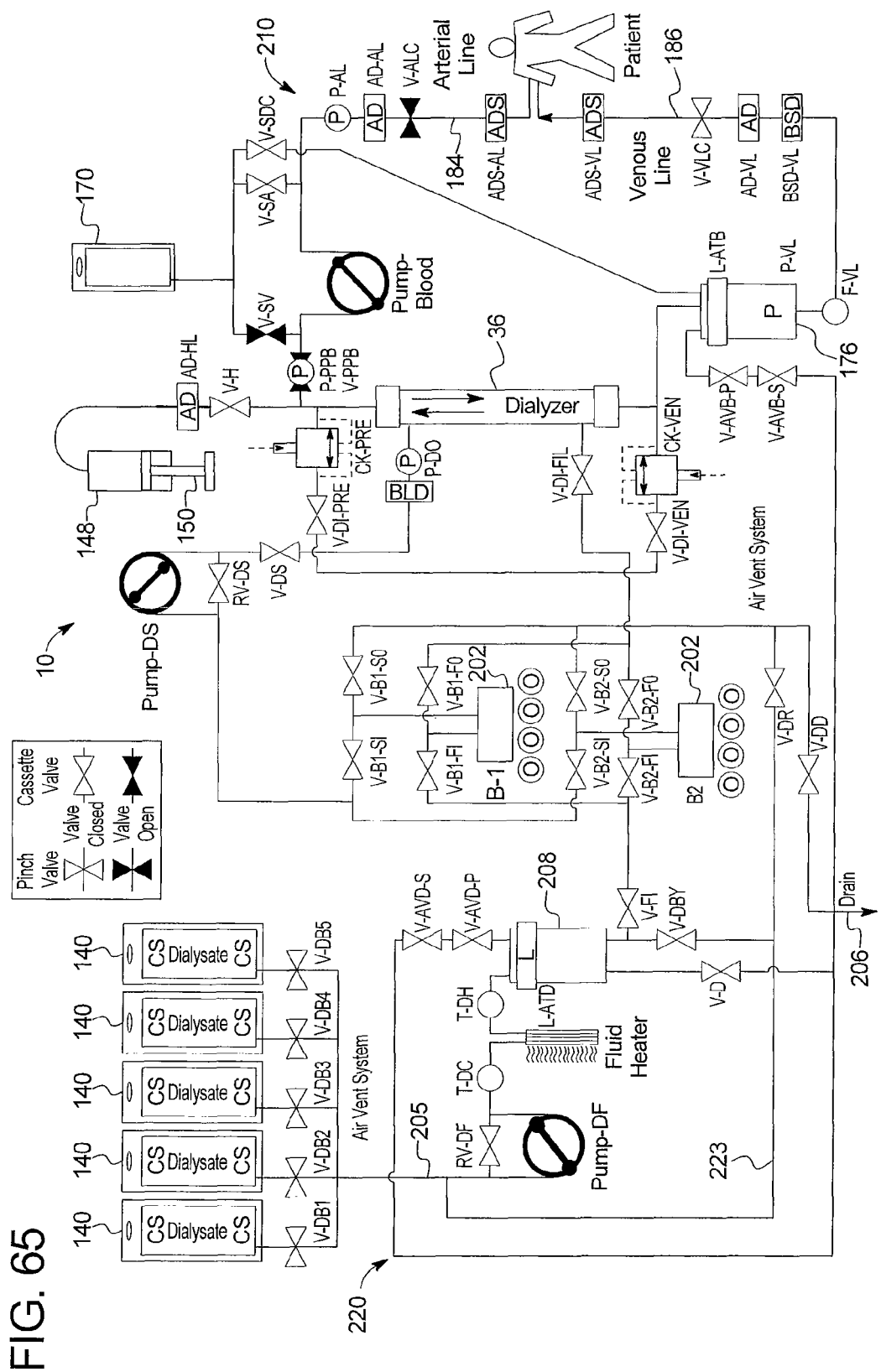
FIG. 65 is a fluid schematic illustrating one embodiment for closing a venous line clamp, opening a saline valve and rinsing back blood from the arterial line.

FIG. 65 illustrates one embodiment for closing venous line clamp V-VLC, opening a saline valve V-SA and rinsing back the arterial line 184.

Figure 66:
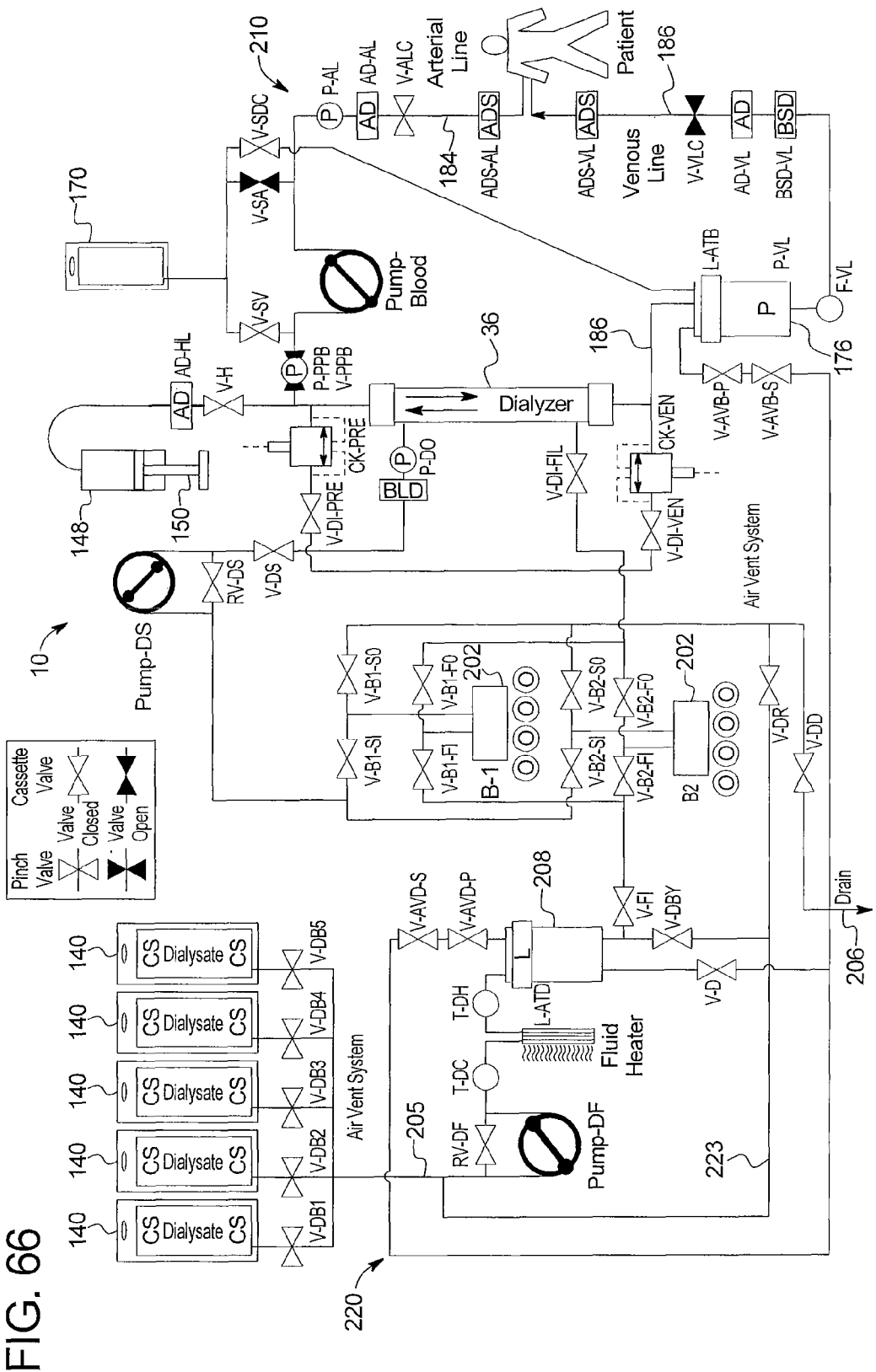
FIG. 66 is a fluid schematic illustrating one embodiment for closing an arterial line clamp, opening a saline valve and rinsing back blood from the venous line.

FIG. 66 illustrates one embodiment for closing arterial line clamp V-ALC, opening a saline valve V-SA and rinsing back the venous line 186.

Figure 67:
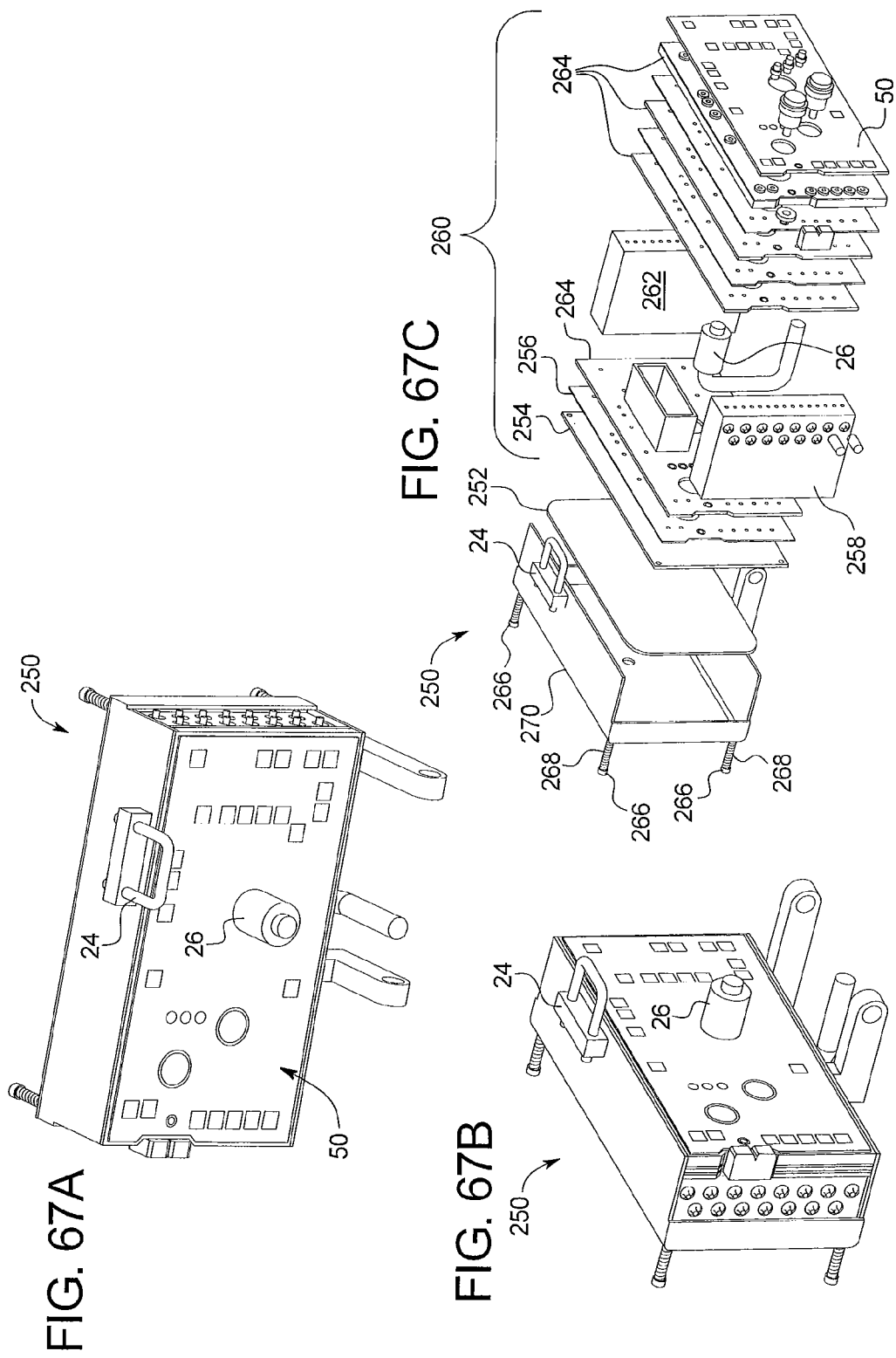
FIG. 67A is a perspective view of one embodiment of a disposable interface subassembly operable with the HHD system of the present disclosure.
FIG. 67B is another view of the disposable interface subassembly of FIG. 67A.
FIG. 67C is an exploded view of an internal module operable with the subassembly of FIGS. 67A and 67B.

FIGS. 67A to 67C illustrate a cassette interface assembly 250, which houses, among other items, cassette interface 50, door latch 24, heater 26, a bellows bladder 252 and an internal module 260. Internal module 260 is bounded by interface plate 50 and a back plate 254. Internal module 260 houses a plurality of gaskets 256, a pneumatic valve assembly 258, a pinch valve assembly 262, and a plurality of manifold plates 264.

All or most all of the valves, pressure sensors, level sensors, etc., can be removed without disassembly of subassembly 250. The inductive heater mechanism 26 and bellows bladder 252 (different from bladder 92 above) require removal of internal module 260. To this end, four screws 266, each with a spring 268, fix a housing 270 of subassembly 250 to internal module 260. Internal module 260 can be unbolted from screws 266, so that springs 268 push internal module 260 forward and out of the housing 270. Power and control connections (not shown) to subassembly 250 are also disconnected to remove internal module 260 completely.

Figure 68:
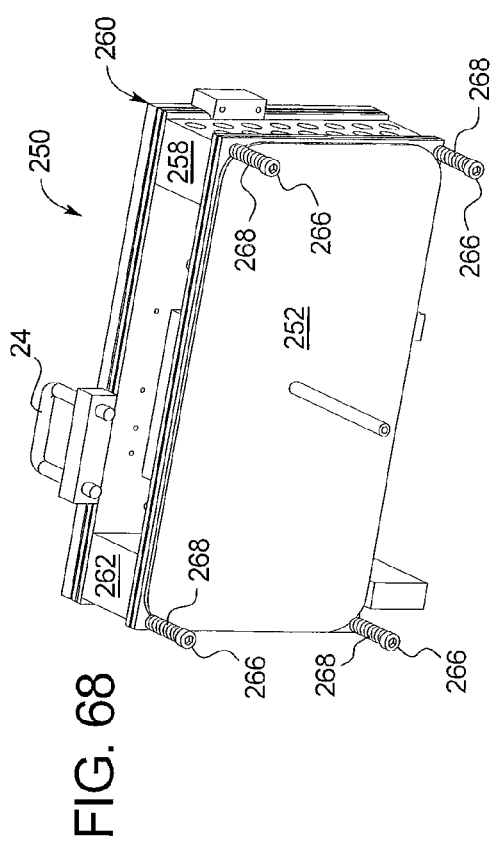
FIG. 68 is a perspective view illustrating springs at the four corners of the subassembly of FIGS. 67A and 67B that retract the internal module of FIG. 67C.
Figure 70:
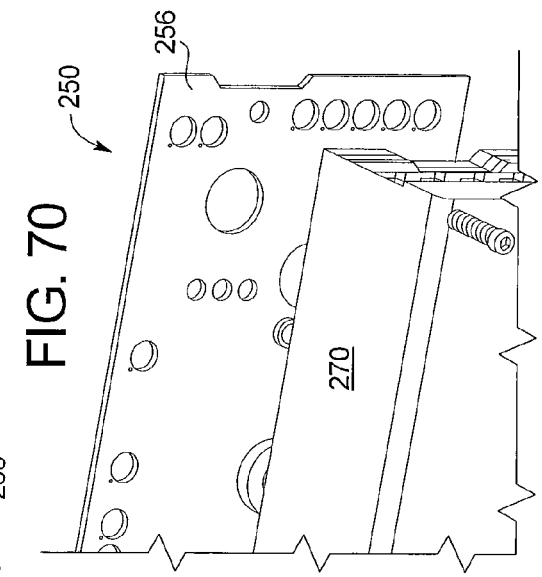
FIG. 70 is a perspective view illustrating the backside of one embodiment of a membrane gasket operable with the HHD system of the present disclosure.
Figure 69:
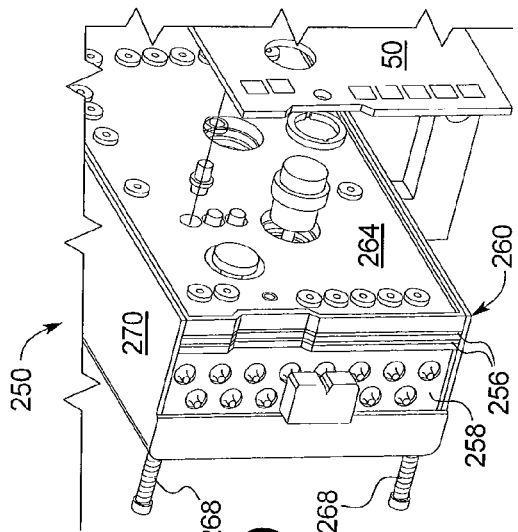
FIG. 69 is a perspective view illustrating the backside of one embodiment of a cassette interface faceplate operable with the HHD system of the present disclosure.

As seen additionally in FIGS. 68 to 70, four springs 268 on the backside of subassembly 250 retract the internal interface module 260 when bellows bladder 252 is not pressurized by pushing screens away from housing 270 and pulling interface module 260 along with the screws. When the bellows bladder 252 is pressurized, internal module 260 is pushed forward and applies pressure to cassette 40, pushing the cassette against a door gasket, which seals fluid pathways on both the front side and the rear side of the cassette 40. The membrane gaskets 256 on the internal module 260 mate up against the faceplate 50 of the interface module 250. The faceplate 50 is configured so that it can support a vacuum between the cassette sheeting and pressure sensors, liquid level sensors, etc., bringing the sensors into intimate contact with the cassette sheeting and the fluid on the other side of the sheeting. System 10 is also configured to port a vacuum between the cassette sheeting and the thin sections of the membrane gasket 256 above the valves. This vacuum can be used to detect holes, tears or slits in the cassette sheeting before, and during a therapy.

Figure 71:
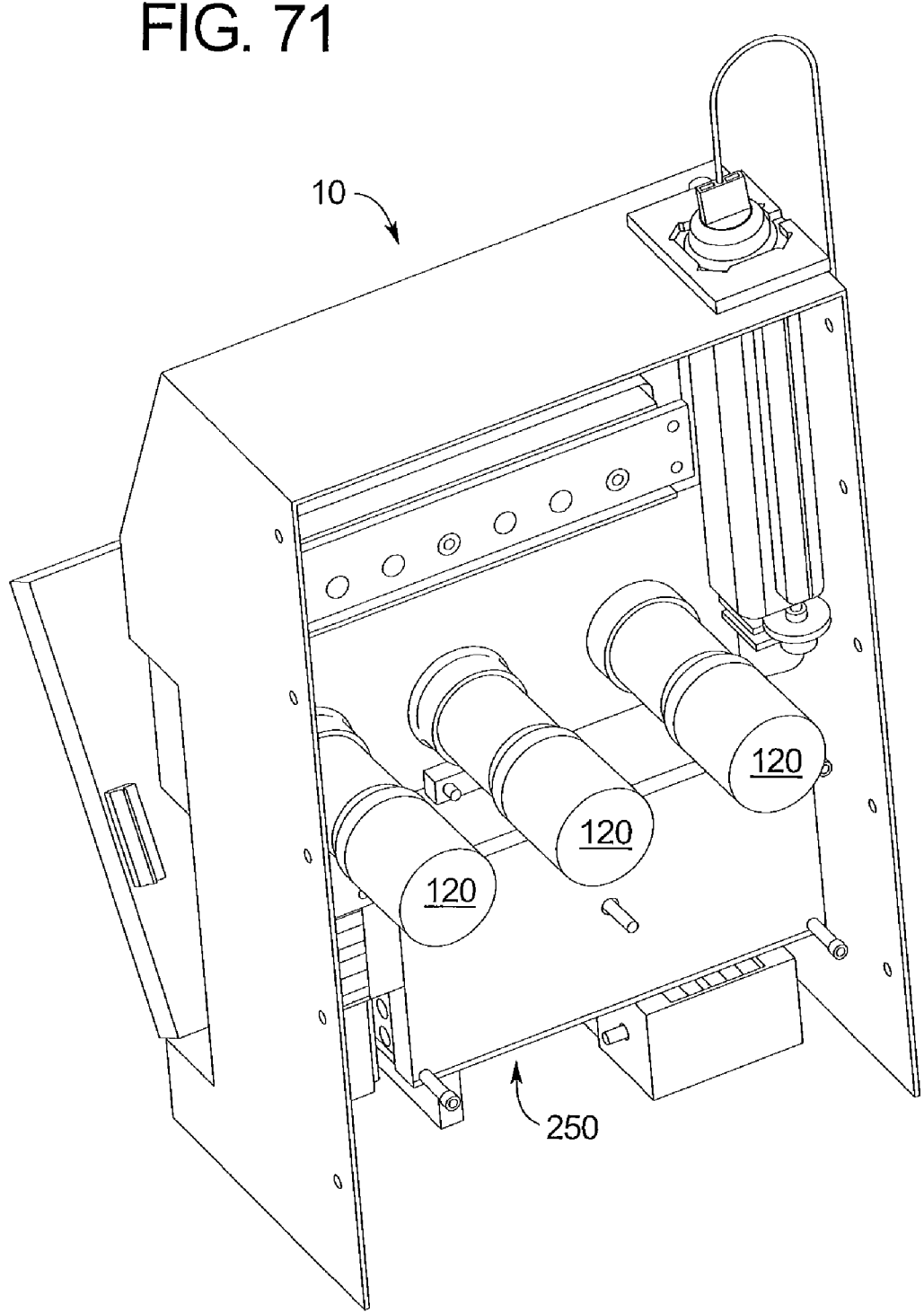
FIG. 71 is a perspective view of the internal instrument components from the backside of the hemodialysis system, showing that there is room for additional, e.g., electrical, components.

FIG. 71 is a view of the backside of system 10 with the cover removed. The open space houses interface assembly 250, hinged shelves 16, peristaltic pump motors 120 a pneumatic pump, a power supply, battery and electronics that operate the system.

Figure 72:
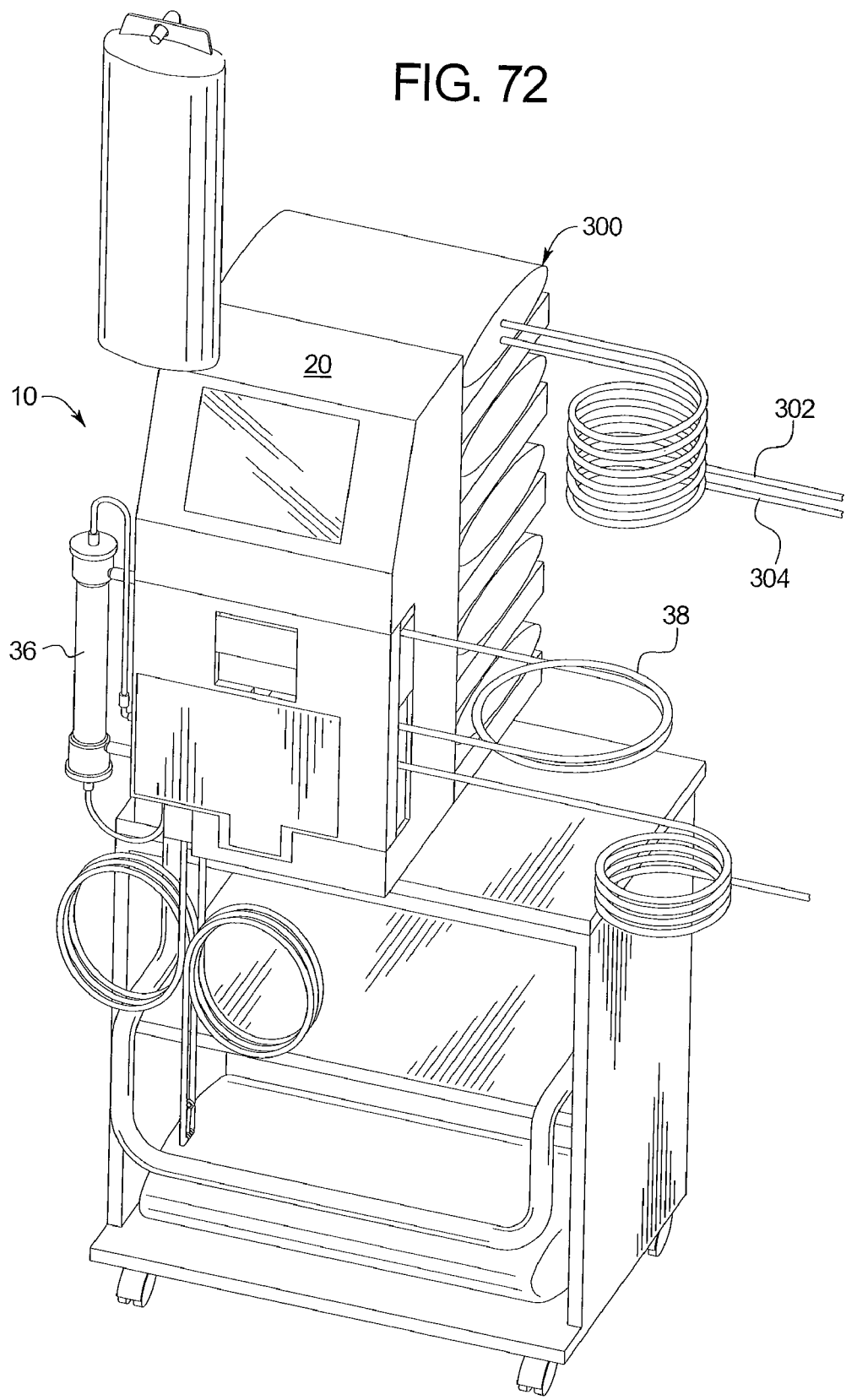
FIG. 72 is a perspective view of one embodiment of the HHD system operating in conjunction with an online dialysate generation system.

FIG. 72 illustrates system 10 operating alternatively with an online dialysate generation system 300. System 300 generates dialysate online or on-demand, eliminating bags 140, shelves 16 and multiple supply tubes 38. A single supply tube 38 feeds from generation system 300 to instrument 20. Water inlet line 302 and drain lines 304 lead to and from generation system 300, respectively.

FIGS. 73A, 73B and 74 illustrate a cassette 40 diaphragm valve chamber configuration 280, which solves an inherent problem with diaphragm valves have when attempting to seal against downstream pressure because the pressure that is trying to seal off the valve is acting on an area that is just slightly larger than an area upon which the downstream pressure is acting. The difference between the two areas is the area defined by the top of the "volcano". Also, if the downstream fluid volume is completely fixed when the diaphragm valve closes, further movement of the diaphragm is prevented after the initiation of the seal because of the incompressibility of the trapped fluid. The result is that the downstream pressure equals the valve sealing pressure. Diaphragm valve configuration 280 provides a diaphragm valve that can seal against both upstream and downstream pressure via a connection of two diaphragm valve chambers 282 and 284 placed in series. Diaphragm valve chambers 282 and 284 are connected fluidly via a compliance chamber 286, which allows sheeting seals 288 of the cassette sheeting to close around respective volcano ports 290 of both valve chambers 282 and 284.

Chamber configuration 280 in both FIGS. 73A and 73B includes a rigid middle or base wall 281 from which valve ports 290 and the valve chamber walls extend upwardly. Wall 281 defines an aperture 283 for each valve chamber 282 and 284. Fluid communicates between valve chambers 282 and 284 and compliance chamber 286 via apertures 283.

FIG. 73A shows a cross-section of two diaphragm valve chambers 282 and 284 with an integral compliance chamber 286, wherein the diaphragms can readily close seals 288 to ports 290. Here, a vacuum is applied to a lower diaphragm 289 at the compliance chamber 286. Diaphragm 289 is flexible and has a relatively large cross-sectional area to absorb the kinetic energy created by a pneumatic valve actuator applying a positive pressure Pa, such that the positive sealing pressure applied to one valve chamber 282 or 284 is much less likely to harm an existing seal of a fluidly connected upstream or downstream valve chambers. The negative pressure pulls sheeting 288 down around ports 290 and allows valve chamber 282 or 284 to be sealed against the backpressure applied by its own sealing pressure (around the outside of port 290) plus backpressure from a fluidly connected upstream or downstream valve chamber residing up through the center of port 290.

Compliance chamber 286 as seen in FIG. 73B is configured a little bit differently and uses a portion of the membrane or sheeting seals 288 of valve chambers 282 and 284 to provide a compliant material covering a relatively large cross-sectional area 292 of chamber 286. Here, a vacuum applied to sheeting 288 at chamber 286 negates the positive pressure Pc applied around the outside of ports 290 and expands the relatively large area 292 of the valve seal sheeting, pulling sheeting 288 down around the outside of port 290. The configuration of FIG. 73B is advantageous in one respect because positive and negative pressures are applied to the same side of the cassette at chamber configuration 280, such that associated pneumatics can be located on a single side of the cassette.

By changing the pressure seen at compliance chamber 286 from a positive pressure when the valve chambers 282 and 284 are open to a negative value after the valve chambers results in that only the liquid side center of the volcano port 290 is exposed to high positive pressure. The liquid annular area of valve chambers 282 and 284 on the outside of volcano ports 290 sees the applied vacuum, which allows the air sealing pressure on the outside of the cassette to seal against backpressures that would have otherwise forced it open. This allows valve chambers 282 and 284 to seals well in both upstream and downstream configurations.

In one example, suppose the total seal area of valve chambers 282 and 284 is one square inch and that the sealing area at the top of volcano port 290 is 0.1 square inch over the volcano. A positive ten psig air pressure would then apply an external force of 10 lbs to the entire valve chamber 282 or 284. A backpressure on the annular fluid side of the associated port 290 from the applied ten psig pressure plus a backpressure the backpressure up through the center of port 290 from a downstream sealed valve would exert almost the same opposite "unsealing" force of ten pound (only difference would be the small annular area of port 290 at the top, which is a function of the port wall thickness and the diameter of the tube), resulting in a potentially leaky valve chamber 282 or 284. A higher positive pressure, e.g., twenty psig, could be applied to valve chamber 282 or 284 forcing sheeting 288 to seal to port 290 against the 10 psig backpressure, however, the noise generated to create the twenty psig air pressure could objectionable to the user. There would also be no redundancy in the different valve pressures.

Back to back valve chambers 282 and 284 of FIGS. 73A and 73B, on the other hand, separated by an applied negative pressure, e.g., 5 psig vacuum, both seal independently well. The ten psig air pressure would still apply 10 lbs external force to seal both valves 282 and 284, however, the 10 psig pressure at the center of the volcano port 290 and the −5 psig pressure on the annular area around the volcano would apply a total pressure of ten psig*0.1 sq in +(−5 psig)*0.9 sq in =−3.5 lbs. The net force to close the valve would be 13.5 lbs so that valve would seal very well.

It may be possible to not use a separate vacuum and instead rely on the expansion of the flexible part of the compliance chamber 286 to absorb energy from the backpressure from one valve chamber 282 or 284 applied to the other valve chamber 282 or 284. Here, apertures 283 allow the pressurized fluid inside chambers 282 and 284 and around ports 290 to communicate with fluid inside compliance chamber 286 and expand diaphragm 289 or sheeting area 292, allowing the backpressure around ports 290 to dissipate.

Valves V-DI-PRE, CK-PRE, V-DI-VEN and CK-VEN in FIG. 52 (and other flow schematics) and valve chambers 282 and 284 of valve configuration 280 of cassette 40 shown in FIG. 74 are constructed as shown schematically in FIGS. 73A and 73B and can seal against higher pressure in either direction. That is, not only does compliance chamber 286 serve to not disrupt an existing upstream or downstream first valve chamber closure when a second valve chamber in fluid communication with the first valve chamber is opened, compliance chamber 286 also aids in the closure of a first valve chamber when a second valve chamber in communication with the first valve chamber (upstream or downstream) has been closed previously, which could otherwise create positive fluid pressure against which the closure of the first valve chamber would have to fight.

Figure 75:
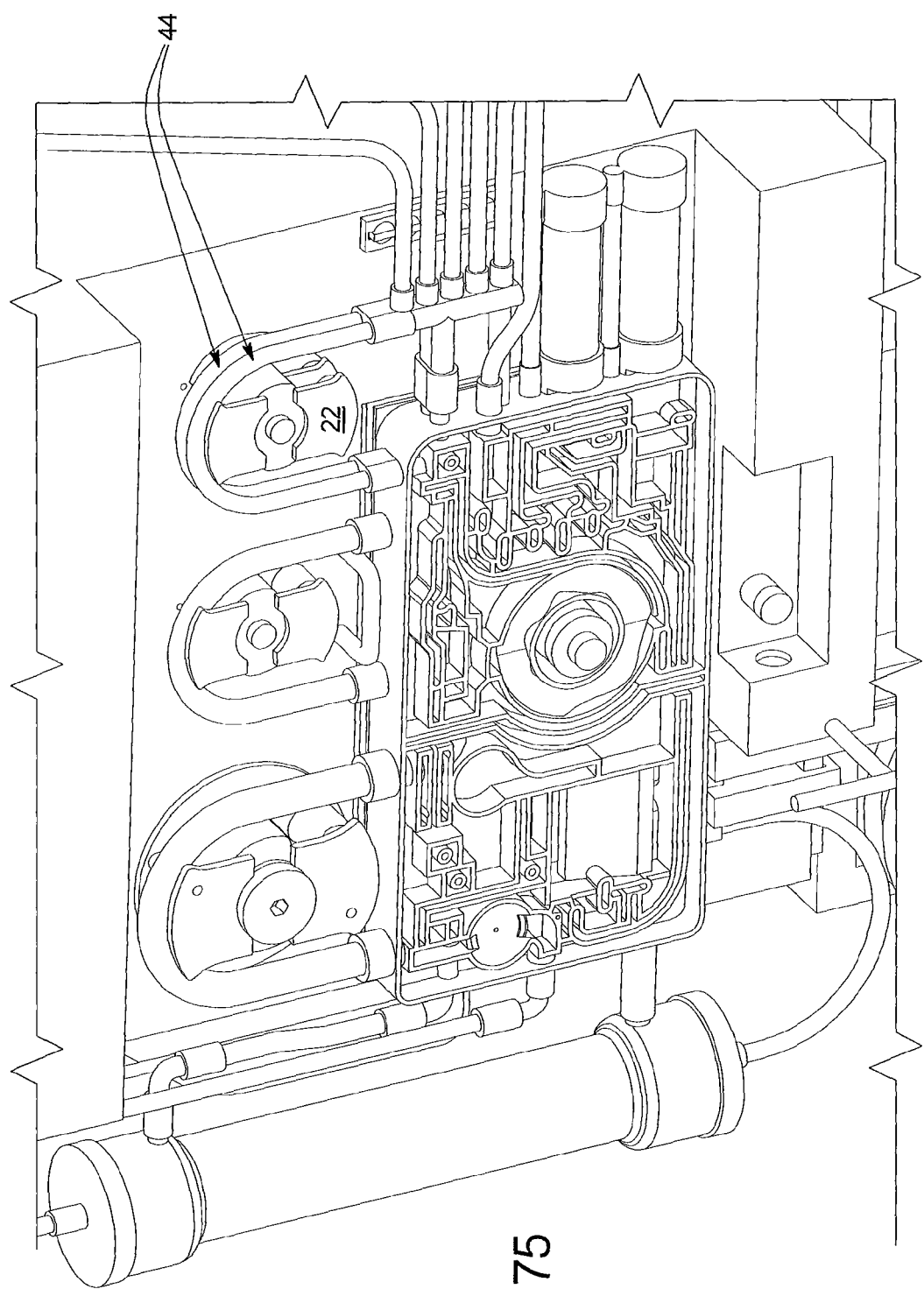
FIG. 75 illustrates one embodiment of a peristaltic pump head sized to operate with multiple supply lines for mixing different fluids of the HHD system of the present disclosure.

FIG. 75 illustrates that system 10 in one embodiment includes a wide pump head 22 that drives two dialysate pump segments 44 to mix two solutions in a ratio that is approximately equal to the ratio of the tube inside diameters squared (mix ratio=(ID1/ID2)2), assuming the wall thicknesses of tubes 44 is the same. For a 1:1 mix ratio, consecutive segments of tubing from the same roll of tubing can be taken to provide segments of the same wall thickness and good mixing accuracy. Mixing accuracy is optimized because the inlet pressure on the supply lines is controlled within about four inches of water column by the bag manager, the tubing inner diameter is controlled during the manufacture of the disposable set, the pump race diameters are the same and the pump actuator rotational speed is the same for the parallel tubing segments. System 10 also ensures that an initial supply fluid temperature of each of the different dialysis fluids in tubes 44 is within a few degrees of each other.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A hemodialysis system comprising:
   blood tubing;
   a peristaltic blood pump contacting the blood tubing to pump blood through the blood tubing;
   a dialyzer in fluid communication with the blood tubing;
   first and second peristaltic dialysate pumps;
   a dialysate heater;
   a plurality of pinch valves aligned in a row;
   a strike plate; and
   a cassette including a rigid structure, a heating portion, first and second dialysate pumping tubes, and a plurality of incoming tubes entering the rigid structure along a same side of the cassette and configured to align so as to match the row of pinch valves, the rigid structure when the cassette is mounted for operation orienting (i) the heating portion adjacent to the dialysate heater so that dialysate can be heated by the dialysate heater, (ii) the first and second dialysate pumping tubes adjacent to the first and second peristaltic dialysate pumps, and (iii) the plurality of incoming tubes adjacent to the plurality of pinch valves to enable the tubes to be individually closed by the pinch valves, and
   wherein the strike plate is located across from the incoming tubes so that each of the pinch valves is positioned to pinch one of the tubes against the strike plate.

2. The hemodialysis system of claim 1, wherein the plurality of incoming tubes extend from the cassette, the plurality of pinch valves residing outside of the cassette when the cassette is mounted for operation.

3. The hemodialysis system of claim 1, wherein the plurality of pinch valves are automatically retracted when a door of the system is opened to facilitate the loading of the cassette.

4. The hemodialysis system of claim 1, wherein the rigid structure carries the first and second dialysate pumping tubes.

5. The hemodialysis system of claim 1, wherein the plurality of incoming tubes are stacked vertically.

6. The hemodialysis system of claim 5, wherein the tubes extend horizontally entering the cassette.

7. The hemodialysis system of claim 6, wherein the strike plate is located on a hemodialysis machine.

8. The hemodialysis system of claim 1, wherein the pinch valves are located outside of the cassette.

9. The hemodialysis system of claim 1, wherein the pinch valves are automatically operated.

10. The hemodialysis system of claim 1, wherein the movement of at least two of the pinch valves is linked.

11. The hemodialysis system of claim 10, wherein the at least two pinch valves are cam driven by a common camshaft.

12. The hemodialysis system of claim 1, which includes at least one valve actuator, and wherein the cassette includes at least one valve actuation area located within the rigid structure, the at least one valve actuation area actuated by the at least one valve actuator.

13. The hemodialysis system of claim 1, which includes electrically actuated arterial and venous line clamps in addition to the plurality of pinch valves.

14. A hemodialysis system comprising:
first and second peristaltic dialysate pumps;
a dialysate heater;
a plurality of pinch valves arranged in a row;
a strike plate;
a cassette including a rigid structure, the rigid structure supporting a heating portion, first and second dialysate pumping tubes; and
a plurality of inlet tubes arranged in a row along a same side of the rigid structure and configured to align in a row so as to match the row of pinch valves, and wherein the rigid structure when the cassette is mounted for operation orients (i) the heating portion adjacent to the dialysate heater so that dialysate can be heated by the dialysate heater, (ii) the first and second dialysate pumping tubes adjacent to the first and second peristaltic dialysate pumps, (iii) the row of inlet tubes adjacent to the plurality of pinch valves to enable the inlet tubes to be individually closed by the pinch valves, and
wherein the strike plate is located across from the plurality of inlet tubes so that each of the pinch valves is positioned to pinch one of the tubes against the strike plate.

15. The hemodialysis system of claim 14, wherein the incoming tubes are each connected to a supply of dialysate.

16. The hemodialysis system of claim 14, wherein the strike plate is located on a hemodialysis machine.

17. The hemodialysis system of claim 14, wherein the rigid structure provides rigid connectors to which the first and second dialysate pumping tubes are connected.

18. The hemodialysis system of claim 14, wherein the rigid structure defines an opening to orient the heating portion adjacent to the dialysate heater so that dialysate can be heated by the dialysate heater.

* * * * *